US006277382B1

(12) United States Patent
Stojiljkovic et al.

(10) Patent No.: US 6,277,382 B1
(45) Date of Patent: *Aug. 21, 2001

(54) HEMOGLOBIN RECEPTORS FROM NEISSERIAE

(75) Inventors: Igor Stojiljkovic; Magdalene So; Vivian Hwa, all of Portland; Fred Heffron, West Linn, all of OR (US); Xavier Nassif, Paris (FR)

(73) Assignee: Oregon Health Sciences University, Portland, OR (US)

( * ) Notice: Subject to any disclaimer, the term of this patent is extended or adjusted under 35 U.S.C. 154(b) by 0 days.

(21) Appl. No.: 08/817,707

(22) PCT Filed: Oct. 17, 1995

(86) PCT No.: PCT/US95/13623

§ 371 Date: Aug. 19, 1997

§ 102(e) Date: Aug. 19, 1997

(87) PCT Pub. No.: WO96/12020

PCT Pub. Date: Apr. 25, 1996

(51) Int. Cl.[7] ................................................. A61K 39/095
(52) U.S. Cl. .................................... 424/249.1; 424/185.1; 424/190.1; 424/250.1; 530/350; 435/69.1; 536/23.1; 536/237
(58) Field of Search .......................... 530/350; 536/23.1, 536/23.7; 424/250.1, 249.1, 185.1, 190.1; 435/69.1

(56) References Cited

U.S. PATENT DOCUMENTS 4,683,195  7/1987  Mullis et al. .
4,683,202  7/1987  Mullis et al. .
5,223,409  6/1993  Ladner et al. .

OTHER PUBLICATIONS

Schryves, (1988) Mol. Microbiol. vol. 2 pp. 467–472.
Lee (1994) Microbiol. 140:1473–1480.
Jarosik et al., (1994) Infect. Immun., 62: pp. 2470–2477.
Lee and Hill, (1992) J. Gen. Microbiol., 138: 2647–2656.
Martek and Lee, (1994) Infect. Immun., 62: 700–703.
McConville and Charles, (1979) J. Microbiol., 113: 165–168.
Mickelson et al., (1982) Infect. Immun., 35: pp. 915–920.
Otto et al., (1992) Crit. Rev. Microbiol., 18: 217–233.
Koebnik et al., (1993) Trends Microbiol 6: pp. 1565–1566.
Archibald and DeVoe, (1979) FEMS Microbiol. Lett., 6, pp. 159–162.
Baggs and Neilands, (1991), Microbiol. Rev., 51, 509–518.
Braun and Hantke, (1991) in Winkelman (ed.) Handbook of Microbial Iron Chelates pp. 107–138.
Calver et al., (1976) Can. J. Microbiol., 22, 832–838.
Cornelissen et al., (1993) J. Bacteriol., 174: pp. 5788–5797.
Correia et al., (1988) J. Biol. Chem., 263: 12194–12198.
Coulton and Pang, (1983) Curr. Microbiol., 9: pp. 93–98.
Dyer et al., (1987) Infect. Immun., 55: pp. 2171–2175.
Fenno et al., (1993) Gene, 130: 81–90.
Gerlach et al., (1992) Infect. Immun., 60: 3253–3261.
Gotschlich et al., (1987) J. Exp. Med., 165: pp. 471–482.
Heller et al., (1988) Gene, 64: pp. 147–153.
Henderson and Payne, (1994) J. Bacteriol, 176: pp. 3269–3277.
Hnatowich et al., (1983) Science, 220: pp. 613–615.
Holbien et al., (1981) Infect. Immun., 34: 120–125.
Kellog et al., (1963) J. Bacteriol., 85: 1274–1279.
Knight et al., (1992) Mol. Microbiol., 6: pp. 1565–1573.
Lundrigan & Kadner, (1986) J. Biol. Chem., 261: pp. 10797–10801.
Meares et al., (1984) Anal. Biochem., 142: 68–78.
Nassif et al., (1993) Mol. Microbiol., 6: pp. 719–725.
Pettersson et al., (1994) J. Bacteriol., 176: pp. 1764–1766.
Pettersson et al., (1993) Infect. Immun., 61: 4724–4733.
Postle, (1990) Mol. Microbiol., 133: pp. 891–898.
Riboli et al., (1991) Microb. Pathogen., 10: pp. 393–403.
Saiki et al., (1988) Science, 230: 1350–1354.
Schoffler and Braun, Molec. Gen. Genet., 217: pp. 378–383.
Schryvers and Morris, (1988) Infect. Immun., 56: pp. 1144–1149.
Schryvers and Morris, (1988) Mol. Microbiol., 2: 281–288.
Schryvers et al., (1989) Infect. Immun., 57(8): pp. 2425–2439.
Stoebner and Payne, (1988) Infec. Immun., 56: pp. 2891–2895.
Struyve et al., (1991) J. Mol. Biol., 218: 141–148.
Walters, (1993) *Pharmaceutical Biotechnology*, pp. 165–174.
Weinberg. (1984) Physiological Rev., 64: pp. 65–102.
West and Sparling, (1985) Infect. Immun., 47: pp. 288–294.
Rudinger, (Jun. 1976), Peptide Hormones, pp. 1–7.

(List continued on next page.)

*Primary Examiner*—Jennifer Graser
(74) *Attorney, Agent, or Firm*—McDonnell Boehnen Hulbert & Berghoff

(57) ABSTRACT

The present invention relates to novel bacterial hemoglobin receptor proteins and genes that encode such proteins. The invention is directed toward the isolation, characterization, diagnostic and therapeutic use of bacterial hemoglobin receptor proteins, nucleic acids encoding such proteins, recombinant expression constructs comprising such nucleic acids and cells transformed therewith, and antibodies and epitopes of such hemoglobin receptor proteins. The invention relates particularly to hemoglobin receptor proteins and genes encoding such proteins from Neisseria species, especially *N. meningitidis* and serotypes thereof, and *N. gonorrhoeae*. Methods for the diagnostic and therapeutic use of the proteins, epitopes, antibodies and nucleic acids of the invention are also provided, including the use of proteins, epitopes, antibodies and nucleic acids of the invention for the production of vaccines effective in providing immunization of human against infection by pathogenic bacteria of Neisseria species.

5 Claims, 47 Drawing Sheets

OTHER PUBLICATIONS

Bittner et al., (1995), Abstract of the General Meeting of the American Society for Microbiology, vol. 95, pp. 227.
Stojiljkovic et al, (1995) Mol. Microbiol., 15: pp. 531–541.
Lewis et al., J. Bacteriol Mar. 1995 177(5): 1299–1306.
Cruse et al. *Atlas of Immunology*, 1999 p. 61.*
Lewis et al., J. Bacteriol. Mar. 1995, 177 (5): 1299–1306.*
Schryvers et al. Infect. Immun. Aug. 1989. 57(8): 2425–2429.*
J. Gen. Microbiol. 1992–138: 2647–2656.*
Bittner et al. ASM Gen. Meeting. 95$^{th}$ Gen. Meeting B–356.*
Stojljkovic et al. Molec. Microbiol. 1995. 15(3): 531–541.*

* cited by examiner

FIG. 2A

```
         10                                                                60
         |                                                                 |
AGAACTAGTGGATCCAATTTGGGCGCGGCGTTTTTGTTCAAACACGCCCAAAAACTCGAT
         BamHI
                                              110
                                               |
TACAACGGGCGAACACGGCGCGCCGCCACCTCGCTCCCGCATCCCCGACGGGCCGGCAAACA
                                              160
                                               |
CTGGCGCGCCTTCGTCGAGCATCTGAACGCTTTGAACCTGACTCCCGAAGCCGAAGCGGA
                                              210
                                               |
AGCCATTCAAGGCGCGCGAAGCCCTTTGCATTCTACAAAGTCGTGTTGCGCGAAACCTT
                                              260
                                               |
CGGCTTGGCAGCCGATGCCGAAGCCCCCGAAGGTATGATGCCCGCACAGGCACTAAAAAAT
                                                              360
                                                               |
AATCGAACCAAATAAACAAGGTCTCCGGCATAGCTGTTTGCAGGGACCTTTAATTACACGG
                                           -10
CGCGGGCTTTGTTTACATGGATTACTGTCTTATTAAATATTAATGATTATCATAAAATCTA
                                           Fur-box                  410
                                                                     |
TTATTCGCTAACCGATGGATGAACAATCCATACACATCTTGAGTTGATAATATGAAACCATT
                                                  SD         MetLysProLe
```

FIG. 2B

```
         510
ACAAATGCTCCCTATCGCCGCGGCTGGTCGGCAGTATTTCGGCAATCCGGTCTTTGCGGC
uGlnMetLeuProIleAlaAlaLeuValGlySerIlePheGlyAsnProValPheAlaAl
                          560
AGATGAAGCTGCAACTGAAACCACACCCGTTAAGGCAGAGGTAAAAGCAGTGCGCGTTAA
aAspGluAlaAlaThrGluThrThrProValLysAlaGluValLysAlaValArgValLy
         610                                           660
AGGCCAGCGCAATGCGCCTGTGGAACGCGTCAACCTTAACCGTATCAAACAAGA
sGlyGlnArgAsnAlaProAlaValAlaGluArgValAsnLeuAsnArgIleLysGlnGl
                                                      710
AATGATACGCGACAACAAAGACTTGGTGCGCTATTCCACCGATGTCGGCTTGAGCGACAG
uMetIleArgAspAsnLysAspLeuValArgTyrSerThrAspValGlyLeuSerAspSe
                          760
CGGCCCGCCATCAAAAAAGGCTTTGCTGTTCGCGGCGTGGAAGGCAACCGTGTCGGCGTGAG
rGlyArgHisGlnLysGlyPheAlaValArgGlyValGlyAsnArgValGlyValSe
         810
CATAGACGGCGTAAACCTGCCTGATTCCGAAGAAAAACTCGCTGTACGCCCGTTATGGCAA
rIleAspGlyValAsnLeuProAspSerGluGluLysLeuTyrAlaArgTyrGlyAs
                                     860
CTTCAACAGCTCGCGTCTGTCTATCGACCCCGAACTCGTGCCAACATCGACATCGTAAA
nPheAsnSerSerArgLeuSerIleAspProGluLeuValAlaArgAsnIleAspIleValLy
```

FIG. 2C

```
910                                                                                         960
 |                                                                                           |
AGGGGCGGACTCTTTCAATACCGGCAGCGGCCTTGGGCGCCGTGTGAATTACCAAAC
sGlyAlaAspSerPheAsnThrGlySerGlyAlaLeuGlyAlaValAsnTyrGlnTh
                                                                                          1010

CCTGCAAGGACGTGACTTACTGTTGCCTGAACGGCAGTTCGGCGTGATGAAAAACGG
rLeuGlnGlyArgAspLeuLeuProGluArgGlnPheGlyValMetMetLysAsnGl
                                      1060

TTACAGCACGCGTAACCGTGAATGGACACAAATACCCTCGGTTTCGGCGTGAGCAACGACCG
yTyrSerThrArgAsnArgGluTrpThrAsnThrLeuGlyPheGlyValSerAsnAspAr
                            1110

CGTGGATGCCGCTTTGCTGTATTCGCAACGGCGGCCATGAAACTGAAAGCGCGGGCAA
gValAspAlaAlaLeuLeuTyrSerGlnArgArgArgHisGluThrGluSerAlaGlyLy
                     1160

GCGTGGTTATCCGGTAGAGGGTGCTGGTAGCGGAGCGAATATCCGTGGTTCTGCCGCGG
sArgGlyTyrProValGluGlyAlaGlySerGlyAlaAsnIleArgGlySerAlaArgGl
             1210                                                                          1260

TATTCCTGATCCGTCCCAACACAAATACCACAGCTTCTTTGGGTAAGATTGCTTATCAAAT
yIleProAspProSerGlnHisLysTyrHisSerPheLeuGlyLysIleAlaTyrGlnIl
                                                                       1310

CAACGACAACCACCGCATCGGCGCATCGCTCAACGGTCAGCAGGGGCATAATTACACGGT
eAsnAspAsnHisArgIleGlyAlaSerLeuAsnGlyGlnGlnGlyHisAsnTyrThrVa
```

FIG. 2D

```
                                             1360
TGAAGAGTCTTACAACCTGCTTGCTTCTTATTGGCGTGAAGCTGACGATGTCAACAGACG
 GluGluSerLeuGlnProAlaCysPheLeuLeuGlyValSerLeuThrMetSerThrAspAr
 (note: reading as shown) GluSerLeuTyrAsnLeuLeuAlaSerTyrTrpArgGluAlaAspAspValAsnArgAr
                                             1410
GCGTAACCAACCTCTTTTACGAATGGACGCCCGGAATCCGACCGGTTGTCTATGGTAAA
 gArgAsnThrAsnLeuPheTyrGluTrpThrProGluSerAspArgLeuSerMetValLy
                                             1460
AGCGGGATGTCGATTATCAAAAACCAAAGTATCTGCGGTCAACTACAAAGGTTCGTTCCC
 sAlaAspValAspTyrGlnLysThrLysValSerAlaValAsnTyrLysGlySerPhePr
                                             1510                          1560
GATAGAGGATTCTTCCACCTTGACACGTAACTACAATCAAAAGGACTTGGATGAAATCTA
 oIleGluAspSerSerThrLeuThrArgAsnTyrAsnGlnLysAspLeuAspGluIleTy
                                             1610
CAACCGCAGTATGGATACCCGCTTCAAACGCATTACCCTGCGTTTGGACAGCCATCCGTT
 rAsnArgSerMetAspThrArgPheLysArgIleThrLeuArgLeuAspSerHisProLe
                                             1660
GCAACTCGGGGGGGGGCGACACCCGTCGTTTAAAACTTTCGCCAGCCGCCGTGATTT
 uGlnLeuGlyGlyGlyArgHisArgIleThrPheLysThrPheAlaSerArgArgAspPh
                                             1710
TGAAAACCTAAAACCGCGACGATTATTACTTCAGCGGCCGTGTTCGAACCACCAGCAG
 eGluAsnLeuAsnArgAsnArgAspAspTyrTyrPheSerGlyArgValValArgThrThrSerSe
```

FIG. 2E

```
TATCCAGCATCCGGGTGAAAACCACCAACTACGGTTTCTCACTGTCTCTGACCAAATTCAATG
rIleGlnHisProValLysThrThrAsnTyrGlyPheSerLeuSerAspGlnIleGlnTr
        1810                                                1860

GAACGACGTGTTCAGTAGCCGGCGCAGGTATCCGTTACGATCATACCAAAATGACGCCCTCA
pAsnAspValPheSerSerArgArgAlaGlyIleArgTyrAspHisThrLysMETThrProGl
                        1860                            1910

GGAATTGAATGCCGAGTGTCATGCTTGTGACAAAACACCGCCAGCCAACACTTATAA
nGluLeuAsnAlaGluCysHisAlaCysAspLysThrProProAlaAlaAsnThrTyrLy
                1910                              1960

AGGCTGGAGCGGGTTTGTCGGCTTGGCGGCGCAACTGAATCAGGCTTGGCCGTGTCGGTTA
sGlyTrpSerGlyPheValGlyLeuAlaAlaGluLeuAsnGlnAlaTrpArgValGlyTy
                1960                              2010

CGACATTACTTCCGGCTACCGTGTCCCCAATGCGTCCGAAGTGTATTTCACTTACAACCA
rAspIleThrSerGlyTyrArgValProAsnAlaSerGluValTyrPheThrTyrAsnHi
                2010                              2060

CGGTTCGGGTAATTGGCTGCCCAATCCCAAACCTGAAAGCCGAGCGCACGACCACCACAC
sGlySerGlyAsnTrpLeuProAsnLeuLysAlaGluArgThrThrThrHisTh
                2060                              2110

CCTCTCTCTGCAAGGCCGCAGCGAAAAAGGTACTTTGGATGCCAACCTGTATCAAAGCAA
rLeuSerLeuGlnGlyArgSerGluLysGlyThrLeuAspAlaAsnLeuTyrGlnSerAs
                2110                              2160
```

FIG. 2F

```
TTACCGCAATTTCCTGTCTCTGAAGAGCAGAAGCTGACCACCAGCGGCGATGTCAGCTGTAC
 nTyrArgAsnPheLeuSerLeuLysGluGlnLysLeuThrThrSerGlyAspValSerCysTh
                                              2260
                           2210

TCAGATGAATTACTACTACGGTATGTGTAGCAATCCTTATTCCGAAAAACTGGAATGGCA
 rGlnMetAsnTyrTyrTyrGlyMetCysSerAsnProTyrSerGluLysLeuGluTrpGl
                    2310

GATGCAAAATATCGACAAGGCCAGAATCCGCGTATCGAGCTGACGGGCCGTCTGAATGT
 nMetGlnAsnIleAspLysAlaArgIleArgGlyIleGluLeuThrGlyArgLeuAsnVa
          2360

GGACAAAGTAGCGTCTTTTGTTCCTGAGGGCTGGAAACTGTTCGGCTCGCTGGGTTATGC
 lAspLysValAlaSerPheValProGluGlyTrpLysLeuPheGlySerLeuGlyTyrAl
                                                     2460

GAAAAGCAAACTGTCGGGCGACAACAGCCTGTCTCCACCCAGCCGTTGAAAGTGATTGC
 aLysSerLysLeuSerGlyAspAsnSerLeuSerThrGlnProLeuLysValIleAl

CGGTATCGACTATGAAAGTCCGAGCGAAAATGGGGCGTGTTCTCCCGCCTGACCTATCT
 aGlyIleAspTyrGluSerProSerGluLysTrpGlyValPheSerArgLeuThrTyrLe
                                                  2510
                    2560

GGGCGCGAAAAGGTCAAAGACGCGCAATACACCGTTTATGAAAACAAGGGCTGGGGTAC
 uGlyAlaLysLysValLysAspAlaGlnTyrThrValTyrGluAsnLysGlyTrpGlyTh
```

FIG. 2G

```
         2610
GCCTTTGCAGAAAAAGGTAAAAGATTACCCGTGGCTGAACAAGTCGGCTTATGTGTTCGA
 rProLeuGlnLysLysValLysAspTyrProTrpLeuAsnLysSerAlaTyrValPheAs
                    2660

TATGTACGGCTTCTACAAACCGGTGAAAAACCTGACTTTGCGTGCAGGCGTATATAATGT
 pMetTyrGlyPheTyrLysProValLysAsnLeuThrLeuArgAlaGlyValTyrAsnVa
  2710                                                   2760

GTTCAACCGCAAATACACCACCACTTGGGATTCCCTGCGCGGCCTGTATAGCTACAGCAC
 lPheAsnArgLysTyrThrThrThrTrpAspSerLeuArgGlyLeuTyrSerThrThrTh
                                                    2810

CAACTCGGTCGACCGCGATGGCAAAGGCTTAGACCGCTACCGCGCCCCAAGCCGTAATTA
 rAsnSerValAspArgAspGlyLysGlyLeuAspArgTyrArgAlaProSerArgAsnTy
                              2860

CGCCCGTATCGCTGGAATGGAAGTTTTAATCTGGTATTATTGAATTAATCGCCTTGTTGAA
 rAlaValSerLeuGluTrpLysPheSTOP
                           2910

AATTAAAGCCCGTCCGAATTGTGTTCAAGAACTCATTCGGACGGTTTTACCGAATCTGTG
                    2960

TGTGGGTTTATAGTGGATTAACAAAAATCAGGAGACAAGGGCGACGAAGCCGAGACAGTACA
```

FIG. 2H

```
3010
GATAGTACGGAACCGATTCACTTGGTGAGACCCTTTGCAAAATTCCTTTCCCTCCCGACAG
                                    ------> IS1106        3060
                                                    3110
CCGAAACCCAAACACAGGTTTTCGGCTGTTTTCGCCCCAAATACCTCCTAATTCTACCCA
                                                3160
AATACCCCCTTAATCCTCCCCGATACCCCGATAATCAGGCATCCCGGCGCCTTTAGGCGGCA
                    3210
GCGGGGCGCACTTAACCTGTTGGCGGCTTTCAAAAGGTTCAAACACATCGCCCTTCAGGTGC
            3260
CTTTGCGCACTCACTTTAATCAGTCCGAAATAGGCCCGCCCGGCATAGCAGAACTTACGG
3310
TGCAGCGTACCGAAGCTT
          HindIII
```

FIG. 4A

```
TBP1M  MQQQHLFRLNILCLSLMTALPVYA---ENVQAEQAQEKQLDTIOVKAKKQ    47
LBPA   MNKKHGFQLTLTALAVAAAFPSYAANPETAAPDAAQTQSLKEVTVRAAKV    50
HMBR   MKPLQMLPIAALVGSIFGN-PVFAADBAATETTPVKAE-----VKAVR     43
                 *                                  *      *

TBP1M  KTRRDNEVTGLGKLVKSSDTLSKEQVLNIRDLTRYDPGIAVVEQGRGASS    97
LBPA   -GRRSKEATGLGKIAKTSETLNKEQVLGIRDLTRYDPGVAVVEQGNGASG    99
HMBR   KGQRNA-PAAVERV--NLNRIKQEMIRDNKDLVRYSTDVGLSDSGRHQK-    89
          *        *             *  *   * **  **    *

TBP1M  GYSIRGMDKNRVSLTVDGVSQIQSYTAQAALGGTRTAGSSGAINEIEYEN   147
LBPA   GYSIRGVDKNRVAVSVDGVAQIQAFTVQGSLSGYGGRGGSGAINEIEYEN   149
HMBR   GFAVRGVEGNRVGVSIDGVNLPDS--EENSLYARYGNFNSSRLS-IDPEL   136
        *  **  * **  * ** *        *                 *  *

TBP1M  VKAVEISKGSNSSEYGNGALAGSVAFQTKTAADIIGEGKQWGIQSKTAYS   197
LBPA   ISTVEIDKGAGSSDHGSGALGGAVAFRTKEAADLISDGKSWGIQAKTAYG   199
HMBR   VRNIDIVKGADSFNTGSGALGGGVYNQTLQGRDLLLPERQFGVMMKNGYS   186
          **    *      *    *  *                       *

TBP1M  GKDHALTQSLALAGRSGGAEALLIYTKRRGREIHAHKDAGKGVQ-SFNRL   246
LBPA   SKNRQFMKSLGAGFSKDGWEGLLIRTBRQGRETHPHGDIADGVAYGINRL   249
HMBR   TRNREWTNTLGFGVSNDRVDAALLYSQRRGHETESAG-----------   223
          *           *     * *      ***
```

FIG. 4B

```
TBP1M  PICRFGNNTYT-DCTPRNIGGNGYYAAVQDNVRLGRWADVGAGIRYDYRS              601
LBPA   SVCGYIETLRSRKCVPRKINGSNIHISLNDRFSIGKYFDFSLGGRYDRKN              635
HMBR   ------SSIQHPVKTTNYGFSLSDQIQWNDVFSSRAGIRYDHTK                    460
                                  *                    * ***

TBP1M  THSED------KSVSTGTHRNLSWNAGVVLKP--FTWMDLTYRASTGF                641
LBPA   FTTSE------ELVRSGRYVDRSWNSGIVFKP--NRHFSLSYRASSGF                675
HMBR   MTPQELNAECHACDKTPPAANTYKGWSGFVGLAAQLNQAWRVGYDITSGY              510
           *                                             *

TBP1M  RLPSFAEMYGWRA----GESLKTLDLKPEKSFNREAGIVFKGDFGNLEAS              687
LBPA   RTPSFQELFGIDIYHDYPKGWQRPALKSEKAANREIGLQWKGDFGFLEIS              725
HMBR   RVPNASEVY-FTYNHGSGNWLPNPNLKAERTTHTLSLQGRSEKGTLDAN               559
       * *                                       *    *

TBP1M  YFNNAYRDLIAFGYET---RTQNGQTSASGDPGYR------------                 719
LBPA   SFRNRYTDMIAVADHKTKLPNQAGQLTEIDIRDYY------------                 760
HMBR   LYQSNYRNFLS---EEQKLTT-SGDVSCTQMNYYYGMCSNPYSEKLEWQM              605
                                *

TBP1M  -NAQNARIAGINILGKIDWHGVWGGLPDG--LYSTLAYNRIKVKDADIRA              766
LBPA   -NAQNMSLQGVNILGKIDWNGVYGKLPEG--LYTTLAYNRIKPKSVSNRP              807
HMBR   QNIDKARIRGIELTGRLNVDKVASFVPEGWKLFGSLGYAKSKLSG----               650
            * *         *         *    *   * *
```

FIG. 4C

```
TBP1M  DRTFVTSYLFDAVQPSRYVLGLGYDHPDGIWGINTMFTYSKAKSVDE---     813
LBPA   GLSL-RSYALDAVQPSRYVLGFGYDQPEGKWGANIMLTYSKGKNPDE---     853
HMBR   DNSLLST-----QPLKVIAGIDYESPSEKWGVFSRLTYLGAKKVKDAQY      694
              *              .          **        *

TBP1M  -LLGSQALLNGNANAKKAASRRTRPWYVTDVSGYYNIKKHLTLRAGVYNL     862
LBPA   -L----AYLAGDQK-RYSTKRASSSWSTADVSAYLNLKKRLTLRAAIYNI     897
HMBR   TVYENKGWGTPLQKKVKDYPWLNKSAYVFDMYGFYKPVKNLTLRAGVYNV     744
              .              *          . *    . ** *. * *.

TBP1M  LNYRYVTWBNVRQ--TAGGAVNQHKNVGVYNRYAAPGRNYTFSLEMKF       908
LBPA   GNYRYVTWESLRQ--TAESTANRHGGDSNYGRYAAPGRNFSLALEMKF       943
HMBR   FNRKYTTWDSLRGLYSYSTTNSVDRDGKGLDRYRAPSRNYAVSLEWKF       792
        *  ***          .               **  .**  *  ***
```

```
ATG AAA CCA TTA CAA ATG CCC CCT ATC GCC GCG CTG CTC GGC AGT ATT        48
Met Lys Pro Leu Gln Met Pro Pro Ile Ala Ala Leu Leu Gly Ser Ile
 1               5                  10                  15

TTC GGC AAT CCG GTC TTT GCG GCA GAT GAA GCT GCA ACT GAA ACC ACA        96
Phe Gly Asn Pro Val Phe Ala Ala Asp Glu Ala Ala Thr Glu Thr Thr
             20                  25                  30

CCC GTT AAG GCA GAG GTA AAA GCA GTG CGC GTT AAA GCA ACT CAG CGC AAT   144
Pro Val Lys Ala Glu Val Lys Ala Val Arg Val Lys Gly Gln Arg Asn
         35                  40                  45

GCG CCT GCG GCT GTG GAA CGC GTC AAC CTT AAC CGT ATC AAA CAA GAA       192
Ala Pro Ala Ala Val Glu Arg Val Asn Leu Asn Arg Ile Lys Gln Glu
     50                  55                  60

ATG ATA CGC GAC AAT AAA GAC TTG GTG CGC TAT TCC ACC GAT GTC GGC       240
Met Ile Arg Asp Asn Lys Asp Leu Val Arg Tyr Ser Thr Asp Val Gly
 65                  70                  75                  80

TTG AGC GAC AGG AGC CGT CAT CAA AAA GGC TTT GCC ATT CGC GGC GTG       288
Leu Ser Asp Arg Ser Arg His Gln Lys Gly Phe Ala Ile Arg Gly Val
             85                  90                  95
```

FIG. 7B

```
GAA GGC GAC CGT GTC GGC GTT AGT ATT GAC GGC GTA AAC CTG CCT GAT    336
Glu Gly Asp Arg Val Gly Val Ser Ile Asp Gly Val Asn Leu Pro Asp
            100                 105                 110

TCC GAA GAA AAC TCG CTG TAC GCC CGT TAT GGC AAC TTC AAC AGC TCG    384
Ser Glu Glu Asn Ser Leu Tyr Ala Arg Tyr Gly Asn Phe Asn Ser Ser
        115                 120                 125

CGT CTG TCT ATC GAC CCC GAA CTC GTG CGC AAC ATC GAC ATC GTA AAA    432
Arg Leu Ser Ile Asp Pro Glu Leu Val Arg Asn Ile Asp Ile Val Lys
    130                 135                 140

GGG GCG GAC TCT TTC AAT ACC GGC AGC GGC GCC TTG GGC GGC GGT GTG    480
Gly Ala Asp Ser Phe Asn Thr Gly Ser Gly Ala Leu Gly Gly Gly Val
145                 150                 155                 160

AAT TAC CAA ACC CTG CAA GGA CGT GAC TTA CTG TTG CCT GAA CGG CAG    528
Asn Tyr Gln Thr Leu Gln Gly Arg Asp Leu Leu Leu Pro Glu Arg Gln
            165                 170                 175

TTC GGC GTG ATG ATG AAA AAC GGT TAC AGC ACG CGT AAC CGT GAA TGG    576
Phe Gly Val Met Met Lys Asn Gly Tyr Ser Thr Arg Asn Arg Glu Trp
        180                 185                 190
```

FIG. 7C

```
ACA AAT ACC CTC GGT TTC GGC GTG AGC AAC GAC CGC GTG GAT GCC GCT      624
Thr Asn Thr Leu Gly Phe Gly Val Ser Asn Asp Arg Val Asp Ala Ala
            195                 200                 205

TTG CTG TAT TCG CAA CGG CGC GGC CAT GAA ACT GAA AGC GCG GGC AAG      672
Leu Leu Tyr Ser Gln Arg Arg Gly His Glu Thr Glu Ser Ala Gly Lys
        210                 215                 220

CGT GGT TAT CCG GTA GAG GGT GCT GGT AGC GGA GCG AAT ATC CGT GGT      720
Arg Gly Tyr Pro Val Glu Gly Ala Gly Ser Gly Ala Asn Ile Arg Gly
    225                 230                 235                 240

TCT GCG CGC GGT ATT CCT GAT CCG TCC CAA CAC AAA TAC CAC AGC TTC      768
Ser Ala Arg Gly Ile Pro Asp Pro Ser Gln His Lys Tyr His Ser Phe
                245                 250                 255

TTG GGT AAG ATT GCT TAT CAA ATC AAC GAC AAC CAC CGC ATC GGC GCA      816
Leu Gly Lys Ile Ala Tyr Gln Ile Asn Asp Asn His Arg Ile Gly Ala
            260                 265                 270

TCG CTC AAC GGT CAG CAG GGG CAT AAT TAC ACG GTT GAA GAG TCT TAC      864
Ser Leu Asn Gly Gln Gln Gly His Asn Tyr Thr Val Glu Glu Ser Tyr
        275                 280                 285
```

FIG. 7D

```
AAC CTG CTT GCT TCT TAT TGG CGT GAA GCT GAT GTC AAC AGA CGG      912
Asn Leu Leu Ala Ser Tyr Trp Arg Glu Ala Asp Val Asn Arg Arg
    290                 295                 300

CGT AAC ACC AAC CTC TTT TAC GAA TGG ACG CCG GAA TCC GAC CGG TTG  960
Arg Asn Thr Asn Leu Phe Tyr Glu Trp Thr Pro Glu Ser Asp Arg Leu
305                 310                 315                 320

TCT ATG GTA AAA GCG GAT GTC GAT TAT CAA AAA ACC AAA GTA TCT GCG 1008
Ser Met Val Lys Ala Asp Val Asp Tyr Gln Lys Thr Lys Val Ser Ala
    325                 330                 335

GTC AAC TAC AAA GGT TCG TTC CCG ACG AAT TAC ACC ACA TGG GAA ACC 1056
Val Asn Tyr Lys Gly Ser Phe Pro Thr Asn Tyr Thr Thr Trp Glu Thr
340                 345                 350

GAG TAC CAT AAA AAG GAA GTT GGC GAA ATC TAT AAC CGC AGC ATG GAT 1104
Glu Tyr His Lys Lys Glu Val Gly Glu Ile Tyr Asn Arg Ser Met Asp
    355                 360                 365

ACA ACC TTC AAA CGT ATT ACG CTG CGT ATG GAC AGC CAT CCG TTG CAA 1152
Thr Thr Phe Lys Arg Ile Thr Leu Arg Met Asp Ser His Pro Leu Gln
370                 375                 380
```

FIG. 7E

```
CTC GGG GGG CGA CAC CGC CTG TCG TTC AAA ACC TTT GCC GGG CAG    1200
Leu Gly Gly Gly Arg His Arg Leu Ser Phe Lys Thr Phe Ala Gly Gln
385                 390                 395                 400

CGT GAT TTT GAA AAC TTA AAC CGC GAT TAC TAC TTC AGC GGC CGT    1248
Arg Asp Phe Glu Asn Leu Asn Arg Asp Tyr Tyr Phe Ser Gly Arg
        405                 410                 415

GTT GTT CGA ACC AAC AGT ATC CAG CAT CCG GTG AAA ACC AAC        1296
Val Val Arg Thr Asn Ser Ile Gln His Pro Val Lys Thr Asn
420                 425                 430

TAC GGT TTC TCG CTG TCC GAC CAA ATC CAA TGG AAC GAC GTG TTC AGT 1344
Tyr Gly Phe Ser Leu Ser Asp Gln Ile Gln Trp Asn Asp Val Phe Ser
435                 440                 445

AGC CGC GCA GGT ATC CGT TAC GAC CAC ACC AAA ATG ACG CCT CAG GAA 1392
Ser Arg Ala Gly Ile Arg Tyr Asp His Thr Lys Met Thr Pro Gln Glu
450                 455                 460

TTG AAT GCC GAC TGT CAT GCT TGT GAC AAA ACA CCG CCT GCA GCC AAC 1440
Leu Asn Ala Asp Cys His Ala Cys Asp Lys Thr Pro Pro Ala Ala Asn
465                 470                 475                 480
```

FIG. 7F

```
ACT TAT AAA GGC TGG AGC GGA TTT GTC GGC TTG GCG CAG CTG AGC    1488
Thr Tyr Lys Gly Trp Ser Gly Phe Val Gly Leu Ala Gln Leu Ser
            485                 490                 495

CAA ACA TGG CGT TTG GGT TAC GAT GTG ACC TCA GGT TTC CGC GTG CCG    1536
Gln Thr Trp Arg Leu Gly Tyr Asp Val Thr Ser Gly Phe Arg Val Pro
            500                 505                 510

AAT GCG TCT GAA GTG TAT TTC ACT TAC AAC CAC GGT TCG GGC ACT TGG    1584
Asn Ala Ser Glu Val Tyr Phe Thr Tyr Asn His Gly Ser Gly Thr Trp
            515                 520                 525

AAG CCT AAT CCT AAT TTG AAG GCA GAA CGC AGC ACC CAC ACC CTG    1632
Lys Pro Asn Pro Asn Leu Lys Ala Glu Arg Ser Thr His Thr Leu
            530                 535                 540

TCC TTG CAG GGG CGC GGC GAC AAA GGG ACA CTG GAT GCC AAC CTG TAT    1680
Ser Leu Gln Gly Arg Gly Asp Lys Gly Thr Leu Asp Ala Asn Leu Tyr
            545                 550                 555                 560

CAA AGC AAT TAC CGA AAC TTC CTG TCG GAA GAG CAG AAT CTG ACT GTC    1728
Gln Ser Asn Tyr Arg Asn Phe Leu Ser Glu Glu Gln Asn Leu Thr Val
            565                 570                 575
```

FIG. 7G

| | | | | | | | | | |
|---|---|---|---|---|---|---|---|---|---|
| AGC | GGC | ACA | CCC | GGC | TGT | ACT | GAG | GAT | GCT | TAC | TAT | AGA | TGC |
| Ser | Gly | Thr | Pro | Gly | Cys | Thr | Glu | Asp | Ala | Tyr | Tyr | Arg | Cys | 1776
| | | 580 | | | | | 585 | | | | 590 | | |

AGC GGC ACA CCC GGC TGT ACT GAG GAT GCT TAC TAT AGA TGC  1776
Ser Gly Thr Pro Gly Cys Thr Glu Asp Ala Tyr Tyr Arg Cys
          580                 585                 590

AGC GAC CCC TAC AAA GAA AAA CTG GAT TGG CAG ATG AAA AAT ATC GAC  1824
Ser Asp Pro Tyr Lys Glu Lys Leu Asp Trp Gln Met Lys Asn Ile Asp
              595                 600                 605

AAG GCC AGA ATC CGC GGT ATC GAG TTG ACA GGC CGT CTG AAT GTG GAC  1872
Lys Ala Arg Ile Arg Gly Ile Glu Leu Thr Gly Arg Leu Asn Val Asp
              610                 615                 620

AAA GTA GCG TCT TTT GTT CCT GAG GGT TGG AAA CTG TTC GGC TCG CTG  1920
Lys Val Ala Ser Phe Val Pro Glu Gly Trp Lys Leu Phe Gly Ser Leu
              625                 630                 635                 640

GGT TAT GCG AAA AGC AAA CTG TCG GGC GAC AAC AGC CTG CTG TCC ACA  1968
Gly Tyr Ala Lys Ser Lys Leu Ser Gly Asp Asn Ser Leu Leu Ser Thr
              645                 650                 655

CAG CCG CTG AAA GTG ATT GCC GGT ATC GAC TAT GAA AGT CCG AGC GAA  2016
Gln Pro Leu Lys Val Ile Ala Gly Ile Asp Tyr Glu Ser Pro Ser Glu
              660                 665                 670

FIG. 7H

```
AAA TGG GGC GTA TTC TCC CGC CTG ACC TAT CTA GGC GCG AAA AAG GTC    2064
Lys Trp Gly Val Phe Ser Arg Leu Thr Tyr Leu Gly Ala Lys Lys Val
675                 680                 685

AAA GAC GCG CAA TAC ACC GTT TAT GAA AAC AAG GGC TGG GGT ACG CCT    2112
Lys Asp Ala Gln Tyr Thr Val Tyr Glu Asn Lys Gly Trp Gly Thr Pro
690                 695                 700

TTG CAG AAA AAG GTA AAA GAT TAC CCG TGG CTG AAC AAG TCG GCT TAT    2160
Leu Gln Lys Lys Val Lys Asp Tyr Pro Trp Leu Asn Lys Ser Ala Tyr
705                 710                 715                 720

GTG TTT GAT ATG TAC GGC TTC TAC AAA CCG GCT AAA AAC CTG ACT TTG    2208
Val Phe Asp Met Tyr Gly Phe Tyr Lys Pro Ala Lys Asn Leu Thr Leu
                725                 730                 735

CGT GCA GGC GTG TAC AAC CTG TTC AAC CGC AAA TAC ACC ACT TGG GAT    2256
Arg Ala Gly Val Tyr Asn Leu Phe Asn Arg Lys Tyr Thr Thr Trp Asp
            740                 745                 750

TCC CTG CGC GGT TTA TAT AGC TAC AGC ACC AAT GCG GTC GAC CGC        2204
Ser Leu Arg Gly Leu Tyr Ser Tyr Ser Thr Asn Ala val Asp Arg
        755                 760                 765
```

GAT GGC AAA GGC TTA GAC CGC TAC CGC GCC CCA GGC CGC AAT TAC GCC
Asp Gly Lys Gly Leu Asp Arg Tyr Arg Ala Pro Gly Arg Asn Tyr Ala
770                     775                 780                              2352

GTA TCG CTG GAA TGG AAG TTT TAA
Val Ser Leu Glu Trp Lys Phe *
785                     790                                                    2375

```
ATG AAA CCA TTA CAA ATG CTC CCT ATC GCC GCG CTG GTC GGC AGT ATT     48
Met Lys Pro Leu Gln Met Leu Pro Ile Ala Ala Leu Val Gly Ser Ile
 1               5                  10                  15

TTC GGC AAT CCG GTC TTT GCG GCA GAT GAA GCT GCA ACT GAA ACC ACA     96
Phe Gly Asn Pro Val Phe Ala Ala Asp Glu Ala Ala Thr Glu Thr Thr
            20                  25                  30

CCC GTT AAG GCA GAG GTA AAA GCA GTG CGC GTT AAA GGC CAG CGC AAT    144
Pro Val Lys Ala Glu Val Lys Ala Val Arg Val Lys Gly Gln Arg Asn
        35                  40                  45

GCG CCT GCG GCT GTG GAA CGC GTC AAC CTT AAC CGT ATC AAA CAA GAA    192
Ala Pro Ala Ala Val Glu Arg Val Asn Leu Asn Arg Ile Lys Gln Glu
 50                  55                  60

ATG ATA CGC GAC AAC AAA GAC TTG GTG CGC TAT TCC ACC GAT GTC GGC    240
Met Ile Arg Asp Asn Lys Asp Leu Val Arg Tyr Ser Thr Asp Val Gly
 65                  70                  75                  80

TTG AGC GAC AGC GGC CGC CAT CAA AAA GGC TTT GCT GTT CGC GGC GTG    288
Leu Ser Asp Ser Gly Arg His Gln Lys Gly Phe Ala Val Arg Gly Val
            85                  90                  95
```

FIG. 8B

```
GAA GGC AAC CGT GTC GGC GTG AGC ATA GAC GGC GTA AAC CTG CCT GAT          336
Glu Gly Asn Arg Val Gly Val Ser Ile Asp Gly Val Asn Leu Pro Asp
            100                 105                 110

TCC GAA GAA AAC TCG CTG TAC GCC CGT TAT GGC AAC TTC AAC AGC TCG          384
Ser Glu Glu Asn Ser Leu Tyr Ala Arg Tyr Gly Asn Phe Asn Ser Ser
            115                 120                 125

CGT CTG TCT ATC GAC CCC GAA CTC GTG CGC AAC ATC GAC ATC GTA AAA          432
Arg Leu Ser Ile Asp Pro Glu Leu Val Arg Asn Ile Asp Ile Val Lys
    130                 135                 140

GGG GCG GAC TCT TTC AAT ACC GGC AGC GGC GCC TTG GGC GGT GTG              480
Gly Ala Asp Ser Phe Asn Thr Gly Ser Gly Ala Leu Gly Gly Gly Val
145                 150                 155                 160

AAT TAC CAA ACC CTG CAA GGA CGT GAC TTA CTG TTG CCT GAA CGG CAG          528
Asn Tyr Gln Thr Leu Gln Gly Arg Asp Leu Leu Leu Pro Glu Arg Gln
            165                 170                 175

TTC GGC GTG ATG ATG AAA AAC GGT TAC AGC ACG CGT AAC CGT GAA TGG          576
Phe Gly Val Met Met Lys Asn Gly Tyr Ser Thr Arg Asn Arg Glu Trp
            180                 185                 190
```

FIG. 8C

```
ACA AAT ACC CTC GGT TTC GGC GTG AGC AAC GAC CGC GTG GAT GCC GCT    624
Thr Asn Thr Leu Gly Phe Gly Val Ser Asn Asp Arg Val Asp Ala Ala
195                         200                 205

TTG CTG TAT TCG CAA CGG CGC GGC CAT GAA ACT GAA AGC GCG GGC AAG    672
Leu Leu Tyr Ser Gln Arg Arg Gly His Glu Thr Glu Ser Ala Gly Lys
210                         215                 220

CGT GGT TAT CCG GTA GAG GGT GCT GGT AGC GGA GCG AAT ATC CGT GGT    720
Arg Gly Tyr Pro Val Glu Gly Ala Gly Ser Gly Ala Asn Ile Arg Gly
225                         230                 235             240

TCT GCG CGC GGT ATT CCT GAT CCG TCC CAA CAC AAA TAC CAC AGC TTC    768
Ser Ala Arg Gly Ile Pro Asp Pro Ser Gln His Lys Tyr His Ser Phe
            245                         250                 255

TTG GGT AAG ATT GCT TAT CAA ATC AAC GAC AAC CAC CGC ATC GGC GCA    816
Leu Gly Lys Ile Ala Tyr Gln Ile Asn Asp Asn His Arg Ile Gly Ala
        260                         265                 270

TCG CTC AAC GGT CAG CAG GGG CAT AAT TAC ACG GTT GAA GAG TCT TAC    864
Ser Leu Asn Gly Gln Gln Gly His Asn Tyr Thr Val Glu Glu Ser Tyr
275                         280                 285
```

FIG. 8D

```
AAC CTG CTT GCT TCT TAT TGG CGT GAA GCT GAC GAT GTC AAC AGA CGG      911
Asn Leu Leu Ala Ser Tyr Trp Arg Glu Ala Asp Asp Val Asn Arg Arg
290                     295                 300

CGT AAC ACC AAC CTC TTT TAC GAA TGG ACG CCG GAA TCC GAC CGG TTG      960
Arg Asn Thr Asn Leu Phe Tyr Glu Trp Thr Pro Glu Ser Asp Arg Leu
305                     310                 315                 320

TCT ATG GTA AAA GCG GAT GTC GAT TAT CAA AAA ACC AAA GTA TCT GCG     1008
Ser Met Val Lys Ala Asp Val Asp Tyr Gln Lys Thr Lys Val Ser Ala
325                     330                 335

GTC AAC TAC AAA GGT TCG TTC CCG ATA GAG GAT TCT TCC ACC TTG ACA     1056
Val Asn Tyr Lys Gly Ser Phe Pro Ile Glu Asp Ser Ser Thr Leu Thr
340                     345                 350

CGT AAC TAC AAT CAA AAG GAC TTG GAT GAA ATC TAC AAC CGC AGT ATG     1104
Arg Asn Tyr Asn Gln Lys Asp Leu Asp Glu Ile Tyr Asn Arg Ser Met
355                     360                 365

GAT ACC CGC TTC AAA CGC ATT ACC CTG CGT TTG GAC AGC CAT CCG TTG     1152
Asp Thr Arg Phe Lys Arg Ile Thr Leu Arg Leu Asp Ser His Pro Leu
370                     375                 380
```

FIG. 8E

```
CAA CTC GGG GGG CGA CAC CGC CTG TCG TTT AAA ACT TTC GCC AGC    1200
Gln Leu Gly Gly Arg His Arg Leu Ser Phe Lys Thr Phe Ala Ser
385                 390                 395                 400

CGC CGT GAT TTT GAA AAC CTA AAC CGC GAC GAT TAT TAC TTC AGC GGC    1248
Arg Arg Asp Phe Glu Asn Leu Asn Arg Asp Asp Tyr Tyr Phe Ser Gly
            405                 410                 415

CGT GTT GTT CGA ACC ACC AGC AGT ATC CAG CAT CCG GTG AAA ACC ACC    1296
Arg Val Val Arg Thr Thr Ser Ser Ile Gln His Pro Val Lys Thr Thr
        420                 425                 430

AAC TAC GGT TTC TCA CTG TCT GAC CAA ATT CAA TGG AAC GAC GTG TTC    1344
Asn Tyr Gly Phe Ser Leu Ser Asp Gln Ile Gln Trp Asn Asp Val Phe
        435                 440                 445

AGT AGC CGC GCA GGT ATC CGT TAC GAT CAT ACC AAA ATG ACG CCT CAG    1392
Ser Ser Arg Ala Gly Ile Arg Tyr Asp His Thr Lys Met Thr Pro Gln
        450                 455                 460

GAA TTG AAT GCC GAG TGT CAT GCT TGT GAC AAA ACA CCG CCT GCA GCC    1440
Glu Leu Asn Ala Glu Cys His Ala Cys Asp Lys Thr Pro Pro Ala Ala
465                 470                 475                 480
```

FIG. 8F

```
AAC ACT TAT AAA GGC TGG AGC GGT TTT GTC GGC TTG GCG GCG CAA CTG       1488
Asn Thr Tyr Lys Gly Trp Ser Gly Phe Val Gly Leu Ala Ala Gln Leu
                485                     490                 495

AAT CAG GCT TGG CGT GTC GGT TAC GAC ATT ACT TCC GGC TAC CGT GTC       1536
Asn Gln Ala Trp Arg Val Gly Tyr Asp Ile Thr Ser Gly Tyr Arg Val
            500                     505                 510

CCC AAT GCG TCC GAA GTG TAT TTC ACT TAC AAC CAC GGT TCG GGT AAT       1584
Pro Asn Ala Ser Glu Val Tyr Phe Thr Tyr Asn His Gly Ser Gly Asn
        515                     520                 525

TGG CTG CCC AAT CCC AAC CTG AAA GCC GAG CGC ACG ACC ACC CAC ACC       1632
Trp Leu Pro Asn Pro Asn Leu Lys Ala Glu Arg Thr Thr Thr His Thr
    530                     535                 540

CTC TCT CTG CAA GGC CGC AGC GAA AAA GGT ACT TTG GAT GCC AAC CTG       1680
Leu Ser Leu Gln Gly Arg Ser Glu Lys Gly Thr Leu Asp Ala Asn Leu
545                     550                 555                 560

TAT CAA AGC AAT TAC CGC AAT TTC CTG TCT GAA GAG CAG AAG CTG ACC       1728
Tyr Gln Ser Asn Tyr Arg Asn Phe Leu Ser Glu Glu Gln Lys Leu Thr
                565                     570                 575
```

FIG. 8G

```
ACC AGC GGC GAT GTC AGC TGT ACT CAG ATG AAT TAC TAC GGT ATG     1776
Thr Ser Gly Asp Val Ser Cys Thr Gln Met Asn Tyr Tyr Gly Met
            580                 585                 590

TGT AGC AAT CCT TAT TCC GAA AAA CTG GAA TGG CAG ATG CAA AAT ATC 1824
Cys Ser Asn Pro Tyr Ser Glu Lys Leu Glu Trp Gln Met Gln Asn Ile
            595                 600                 605

GAC AAG GCC AGA ATC CGC GGT ATC GAG CTG ACG GGC CGT CTG AAT GTG 1872
Asp Lys Ala Arg Ile Arg Gly Ile Glu Leu Thr Gly Arg Leu Asn Val
            610                 615                 620

GAC AAA GTA GCG TCT TTT GTT CCT GAG GGC TGG AAA CTG TTC GGC TCG 1920
Asp Lys Val Ala Ser Phe Val Pro Glu Gly Trp Lys Leu Phe Gly Ser
            625                 630                 635                 640

CTG GGT TAT GCG AAA AGC AAA CTG TCG GGC GAC AAC AGC CTG CTG TCC 1968
Leu Gly Tyr Ala Lys Ser Lys Leu Ser Gly Asp Asn Ser Leu Leu Ser
            645                 650                 655

ACC CAG CCG TTG AAA GTG ATT GCC GGT ATC GAC TAT GAA AGT CCG AGC 2016
Thr Gln Pro Leu Lys Val Ile Ala Gly Ile Asp Tyr Glu Ser Pro Ser
            660                 665                 670
```

FIG. 8H

```
GAA AAA TGG GGC GTG TTC TCC CGC CTG ACC TAT CTG GGC GCG AAA AAG    2064
Glu Lys Trp Gly Val Phe Ser Arg Leu Thr Tyr Leu Gly Ala Lys Lys
            675                 680                 685

GTC AAA GAC GCG CAA TAC ACC GTT TAT GAA AAC AAG GGC TGG GGT ACG    2112
Val Lys Asp Ala Gln Tyr Thr Val Tyr Glu Asn Lys Gly Trp Gly Thr
            690                 695                 700

CCT TTG CAG AAA AAG GTA AAA GAT TAC CCG TGG CTG AAC AAG TCG GCT    2160
Pro Leu Gln Lys Lys Val Lys Asp Tyr Pro Trp Leu Asn Lys Ser Ala
        705                 710                 715             720

TAT GTG TTC GAT ATG TAC GGC TTC TAC AAA CCG GTG AAA AAC CTG ACT    2208
Tyr Val Phe Asp Met Tyr Gly Phe Tyr Lys Pro Val Lys Asn Leu Thr
            725                 730                 735

TTG CGT GCA GGC GTA TAT AAT GTG TTC AAC CGC AAA TAC ACC ACT TGG    2256
Leu Arg Ala Gly Val Tyr Asn Val Phe Asn Arg Lys Tyr Thr Thr Trp
            740                 745                 750

GAT TCC CTG CGC GGC CTG TAT AGC TAC AGC ACC AAC TCG GTC GAC        2304
Asp Ser Leu Arg Gly Leu Tyr Ser Tyr Ser Thr Asn Ser Val Asp
            755                 760                 765
```

FIG. 8I

```
                                                                              2352
CGC GAT GGC AAA GGC TTA GAC CGC TAC CGC GCC CCA AGC CGT AAT TAC
Arg Asp Gly Lys Gly Leu Asp Arg Tyr Arg Ala Pro Ser Arg Asn Tyr
770                 775                 780
                                                                              2379
GCC GTA TCG CTG GAA TGG AAG TTT TAA
Ala Val Ser Leu Glu Trp Lys Phe *
785                 790
```

FIG. 9A

```
ATG AAA CCA TTA CAC ATG CTT CCT ATT GCC GCG CTG GTC GGC AGT ATT          48
Met Lys Pro Leu His Met Leu Pro Ile Ala Ala Leu Val Gly Ser Ile
 1               5                  10                  15

TTC GGC AAT CCG GTC TTG GCA GCG GAT GAA GCT GCA ACC GAA ACC ACA          96
Phe Gly Asn Pro Val Leu Ala Ala Asp Glu Ala Ala Thr Glu Thr Thr
            20                  25                  30

CCC GTT AAA GCA GAG ATA AAA GAA ATT AAA GAC CAG CTT AAT         144
Pro Val Lys Ala Glu Ile Lys Val Arg Val Lys Asp Gln Leu Asn
        35                  40                  45

GCG CCT GCA ACC GTG GAA CGT GTC AAC CTC GGC CGC ATT CAA CAG GAA         192
Ala Pro Ala Thr Val Glu Arg Val Asn Leu Gly Arg Ile Gln Gln Glu
    50                  55                  60

ATG ATA CGC GAC AAC AAA GAC TTG GTG CGT TAC TCC ACC GAC GTC GGC         240
Met Ile Arg Asp Asn Lys Asp Leu Val Arg Tyr Ser Thr Asp Val Gly
65                  70                  75                  80

TTG AGC GAT AGC GGC CGC CAT CAA AAA GGC TTT GCT GTG CGC GGC GTG         288
Leu Ser Asp Ser Gly Arg His Gln Lys Gly Phe Ala Val Arg Gly Val
        85                  90                  95
```

FIG. 9B

```
GAA GGC AAC CGT GTC GGT GTC AGC ATT GAC GGC GTG AGC CTG CCT GAT    336
Glu Gly Asn Arg Val Gly Val Ser Ile Asp Gly Val Ser Leu Pro Asp
        100                 105                 110

TCG GAA GAA AAC TCA CTG TAT GCA CGT TAT GGC AAC TTC AAC AGC TCG    384
Ser Glu Glu Asn Ser Leu Tyr Ala Arg Tyr Gly Asn Phe Asn Ser Ser
    115                 120                 125

CGC CTG TCT ATC GkC CCC GAA CTC GTG CGC AAC ATC GAA ATC GCG AAG    432
Arg Leu Ser Ile Asp Pro Glu Leu Val Arg Asn Ile Glu Ile Ala Lys
130                 135                 140

GGC GCT GAC TCT TTC AAT ACC GGT AGC GGC TTG GCA TTG GGT GGC GTG    480
Gly Ala Asp Ser Phe Asn Thr Gly Ser Gly Ala Leu Gly Gly Val
145                 150                 155                 160

AAT TAC CAA ACC CTG CAA GGA CAT GAT TTG CTG TTG GAC GAC AGG CAA    528
Asn Tyr Gln Thr Leu Gln Gly His Asp Leu Leu Leu Asp Asp Arg Gln
        165                 170                 175

TTC GGC GTG ATG ATG AAA AAC GGT TAC AGC AGC CGC AAC CGC GAA TGG    576
Phe Gly Val Met Met Lys Asn Gly Tyr Ser Ser Arg Asn Arg Glu Trp
    180                 185                 190
```

FIG. 9C

```
ACA AAT ACA CTC GGT TTC GGT GTG AGC AAC GAC CGC GTG GAT GCC GCT                    624
Thr Asn Thr Leu Gly Phe Gly Val Ser Asn Asp Arg Val Asp Ala Ala
            195                     200                 205

TTG CTG TAT TCG CAA CGT CGC GGT CAT GAG ACC GAA AGC GCG GGC GAG                    672
Leu Leu Tyr Ser Gln Arg Arg Gly His Glu Thr Glu Ser Ala Gly Glu
        210                     215                 220

CGT GGC TAT CCG GTA GAG GGT GCT GGC AGC GGA GCA ATT ATC CGT GGT                    720
Arg Gly Tyr Pro Val Glu Gly Ala Gly Ser Gly Ala Ile Ile Arg Gly
225                     230                     235                 240

TCG TCA CGC GGT ATC CCT GAT CCG TCC AAA CAC AAA TAC CAC AAC TTC                    768
Ser Ser Arg Gly Ile Pro Asp Pro Ser Lys His Lys Tyr His Asn Phe
                245                     250                     255

TTG GGT AAG ATT GCT TAT CAA ATC AAC GAC AAG CAC CGC ATC GGC CCA                    816
Leu Gly Lys Ile Ala Tyr Gln Ile Asn Asp Lys His Arg Ile Gly Pro
            260                     265                     270

TCG TTT AAC GGC CAG CAG GGG CAT AAT TAC ACG ATT GAA GAG TCT TAT                    864
Ser Phe Asn Gly Gln Gln Gly His Asn Tyr Thr Ile Glu Glu Ser Tyr
        275                     280                     285
```

FIG. 9D

```
AAC CTG ACC GCT TCT TCC TGG CGC GAA GCC GAT GAC GTA AAC AGA CGG         912
Asn Leu Thr Ala Ser Ser Trp Arg Glu Ala Asp Asp Val Asn Arg Arg
            290                 295                 300

CGC AAT GCC AAC CTC TTT TAC GAA TGG ACG CCT GAT TCA AAT TGG CTG         960
Arg Asn Ala Asn Leu Phe Tyr Glu Trp Thr Pro Asp Ser Asn Trp Leu
        305                 310                 315                 320

TCG TCT TTG AAG GCG GAC TTC GAT TAT CAG ACA ACC AAA GTG GCG GCG        1008
Ser Ser Leu Lys Ala Asp Phe Asp Tyr Gln Thr Thr Lys Val Ala Ala
            325                 330                 335

GTT AAC AAC AAA GGC TCG TTC CCG ACG GAT TAT TCC ACC TGG ACG CGC        1056
Val Asn Asn Lys Gly Ser Phe Pro Thr Asp Tyr Ser Thr Trp Thr Arg
        340                 345                 350

AAC TAT AAT CAG AAG GAT TTG GAG AAT ATA TAC AAC CGC AGC ATG GAC        1104
Asn Tyr Asn Gln Lys Asp Leu Glu Asn Ile Tyr Asn Arg Ser Met Asp
            355                 360                 365

ACC CGA TTC AAA CGT TTT ACT TTG CGT ATG GAC AGC CAA CCG TTG CAA        1152
Thr Arg Phe Lys Arg Phe Thr Leu Arg Met Asp Ser Gln Pro Leu Gln
        370                 375                 380
```

FIG. 9E

```
CTG GGC CAA CAT CGC TTG TCG CTT AAA ACT TTC GCC AGT CGG CGT          1200
Leu Gly Gln His Arg Leu Ser Leu Lys Thr Phe Ala Ser Arg Arg
385                 390                 395                 400

GAG TTT GAA AAC TTA AAC CGC GAC GAT TAT TAC TTC AGC GAA AGA GTA      1248
Glu Phe Glu Asn Leu Asn Arg Asp Asp Tyr Tyr Phe Ser Glu Arg Val
        405                 410                 415

TCC CGT ACT AGC TCG ATT CAA CAC CCC GTG AAA ACC ACT AAT TAT          1296
Ser Arg Thr Ser Ser Ile Gln His Pro Val Lys Thr Thr Asn Tyr
420                 425                 430

GGT TTC TCA CTG TCT GAT CAA ATC CAA TGG AAC GAC GTG TTC AGC AGC      1344
Gly Phe Ser Leu Ser Asp Gln Ile Gln Trp Asn Asp Val Phe Ser Ser
    435                 440                 445

CGT GCA GAT ATC CGT TAC GAT CAT ACC AAA ATG ACG CCT CAG GAA TTG      1392
Arg Ala Asp Ile Arg Tyr Asp His Thr Lys Met Thr Pro Gln Glu Leu
450                 455                 460

AAT GCC GAG TGT CAT GCT TGT GAC AAA ACA CCG CCT GCA GCC AAT ACT      1440
Asn Ala Glu Cys His Ala Cys Asp Lys Thr Pro Pro Ala Ala Asn Thr
465                 470                 475                 480
```

FIG. 9F

| | | | | | | | | | | | | | | | | |
|---|---|---|---|---|---|---|---|---|---|---|---|---|---|---|---|---|
| TAT | AAA | GGC | TGG | AGC | GGA | TTT | GTC | GGT | TTG | GCG | GCG | CAA | CTG | AAT | CAG | 1488 |
| Tyr | Lys | Gly | Trp | Ser | Gly | Phe | Val | Gly | Leu | Ala | Ala | Gln | Leu | Asn | Gln | |
| | | | 485 | | | | | 490 | | | | | 495 | | | |
| GCT | TGG | CAT | GTC | GGT | TAC | GAC | ATT | ACT | TCC | GGC | TAC | CGT | GTC | CCC | AAT | 1536 |
| Ala | Trp | His | Val | Gly | Tyr | Asp | Ile | Thr | Ser | Gly | Tyr | Arg | Val | Pro | Asn | |
| | | 500 | | | | | 505 | | | | | 510 | | | | |
| GCG | TCC | GAA | GTG | TAT | TTC | ACT | TAC | AAC | CAC | GGT | TCG | GGT | AAT | TGG | CTG | 1584 |
| Ala | Ser | Glu | Val | Tyr | Phe | Thr | Tyr | Asn | His | Gly | Ser | Gly | Asn | Trp | Leu | |
| | 515 | | | | | 520 | | | | | 525 | | | | | |
| CCC | AAT | CCC | AAC | CTG | AAA | GCC | GAG | CGC | AGC | ACC | ACC | CAC | ACC | CTG | TCT | 1632 |
| Pro | Asn | Pro | Asn | Leu | Lys | Ala | Glu | Arg | Ser | Thr | Thr | His | Thr | Leu | Ser | |
| 530 | | | | | 535 | | | | | 540 | | | | | | |
| CTG | CAA | GGC | CGC | AGC | GAA | AAA | GGT | ACT | TTG | GAT | GCC | AAC | CTG | TAT | CAA | 1680 |
| Leu | Gln | Gly | Arg | Ser | Glu | Lys | Gly | Thr | Leu | Asp | Ala | Asn | Leu | Tyr | Gln | |
| 545 | | | | | 550 | | | | | 555 | | | | | 560 | |
| AAC | AAT | TAC | CGC | AAC | TTC | TTG | TCT | GAA | GAG | CAG | AAG | CTG | ACC | ACC | AGC | 1728 |
| Asn | Asn | Tyr | Arg | Asn | Phe | Leu | Ser | Glu | Glu | Gln | Lys | Leu | Thr | Thr | Ser | |
| | | | | 565 | | | | | 570 | | | | | 575 | | |

FIG. 9G

```
GGC GAT GTC GGC TGT ACT CAG ATG AAT TAC TAC TAC GGT ATG TGT AGC    1776
Gly Asp Val Gly Cys Thr Gln Met Asn Tyr Tyr Tyr Gly Met Cys Ser
            580                 585                 590

AAT CCT TAT TCC GAA AAA CCG GAA ATG CAA AAT ATC GAT AAG            1824
Asn Pro Tyr Ser Glu Lys Pro Glu Met Gln Asn Ile Asp Lys
            595                 600                 605

GCC CGA ATC CGT GGT CTT GAG GAG CTG ACA GGC CGT CTG AAT GTG ACA AAA    1872
Ala Arg Ile Arg Gly Leu Glu Leu Thr Gly Arg Leu Asn Val Thr Lys
            610                 615                 620

GTA GCG TCT TTT GTT CCT GAG GGC TGG AAA TTG TTC GGC TCG CTG GGT    1920
Val Ala Ser Phe Val Pro Glu Gly Trp Lys Leu Phe Gly Ser Leu Gly
            625                 630                 635                 640

TAT GCG AAA AGC AAA CTG TCG GGC GAC AAC AGC CTG CTG TCC ACA CAG    1968
Tyr Ala Lys Ser Lys Leu Ser Gly Asp Asn Ser Leu Leu Ser Thr Gln
            645                 650                 655

CCG CCG AAA GTG ATT GCC GGT GTC GAC TAC GAA AGC CCG AGC GAA AAA    2016
Pro Pro Lys Val Ile Ala Gly Val Asp Tyr Glu Ser Pro Ser Glu Lys
            660                 665                 670
```

FIG. 9H

```
TGG GGT GTG TTC TCC CGC CTG ACT TAT CTG GGT GCG AAA AAG GCC AAA      2064
Trp Gly Val Phe Ser Arg Leu Thr Tyr Leu Gly Ala Lys Lys Ala Lys
            675                 680                 685

GAC GCG CAA TAC ACC GTT TAT GAA AAC AAG GGC CGG GGT ACG CCT TTG      2112
Asp Ala Gln Tyr Thr Val Tyr Glu Asn Lys Gly Arg Gly Thr Pro Leu
        690                 695                 700

CAG AAA AAG GTA AAA GAT TAC GAC TAC CCG TGG CTG AAC AAG TCG GCT TAT GTG  2160
Gln Lys Lys Val Lys Asp Tyr Asp Tyr Pro Trp Leu Asn Lys Ser Ala Tyr Val
705                 710                 715                 720

TTT GAT ATG TAC GGC TTC TAC AAA CTG GCT AAA AAC CTG ACT TTG CGT      2208
Phe Asp Met Tyr Gly Phe Tyr Lys Leu Ala Lys Asn Leu Thr Leu Arg
        725                 730                 735

GCA GGC GTA TAT AAT GTG TTC AAC CGC AAA TAC ACC ACT TGG GAT TCC      2256
Ala Gly Val Tyr Asn Val Phe Asn Arg Lys Tyr Thr Thr Trp Asp Ser
            740                 745                 750

CTG CGC GGT TTG TAT AGC TAC AGC ACC AAC ACC AAC GCG GTC GAC CGA GAT  2304
Leu Arg Gly Leu Tyr Ser Tyr Ser Thr Asn Thr Asn Ala Val Asp Arg Asp
        755                 760                 765
```

FIG. 9I

```
                                                            2352              2378
GGC AAA GGC TTA GAC CGC GCC TAC CGC GCC TCA GGC CGT AAT TAC GCC GTA
Gly Lys Gly Leu Asp Arg Ala Tyr Arg Ala Ser Gly Arg Asn Tyr Ala Val
770                 775                 780

TCG CTG GAT TGG AAG TTT TGA ATTCC
Ser Leu Asp Trp Lys Phe  *
785                 790
```

FIG. 11A

```
HMBRA     MKPLQMLPIAALVGSIFGNPVLAADEAATETTPVKAEIKAVRVKGQRNAP      50
HMBRB     MKPLQMPPIAALLGSIFGNPVFAXDEAATETTPVKAEVKAVRVKGQRNAP      50
HMBRC     MKPLQMLPIAALVGSIFGNPVFAADEAATETTPVKAEVKAVRVKGQRNAP      50
HMBRMS11  MKPLHMLPIAALVGSIFGNPVLAADEAATETTPVKAEIKEVRVKDQLNAP      50
          ****.* ******.*****.* ********** ** ***:*** **:***

HMBRA     AAVERVNLNRIKQEMIRDNKDLVRYSTDVGLSDSGRHQKGFAVRGVEGNR     100
HMBRB     AAVERVNLNRIKQEMIRDNKDLVRYSTDVGLSDRSRHQKGFAIRGVEGDR     100
HMBRC     AAVERVNLNRIKQEMIRDNKDLVRYSTDVGLSDSGRHQKGFAVRGVEGNR     100
HMBRMS11  ATVERVNLGRIQQEMIRDNKDLVRYSTDVGLSDSGRHQKGFAVRGVEGNR     100
          *:****** **:******************** .*******:*****:*

HMBRA     VGVSIDGVNLPDSEENSLYARYGNFNSSRLSIDPELVRNIEIVKGADSFN     150
HMBRB     VGVSIDGVNLPDSEENSLYARYGNFNSSRLSIDPELVRNIDIVKGADSFN     150
HMBRC     VGVSIDGVNLPDSEENSLYARYGNFNSSRLSIDPELVRNIDIVKGADSFN     150
HMBRMS11  VGVSIDGVSLPDSEENSLYARYGNFNSSRLSIDPELVRNIEIAKGADSFN     150
          ********.******************************:* ******

HMBRA     TGSGALGGGVNYQTLQGRDLLLDDRQFGVMMKNGYSTRNREWTNTLGFGV     200
HMBRB     TGSGALGGGVNYQTLQGRDLLLPERQFGVMMKNGYSTRNREWTNTLGFGV     200
HMBRC     TGSGALGGGVNYQTLQGRDLLLPERQFGVMMKNGYSTRNREWTNTLGFGV     200
HMBRMS11  TGSGALGGGVNYQTLQGHDLLLDDRQFGVMMKNGYSSRNREWTNTLGFGV     200
          *****************.****  ***********:************
```

FIG. 11B

```
HMBRA    SNDRVDAALLYSQRRGHETESAGNRGYPVEGAGKETNIRGSARGIPDPSK    250
HMBRB    SNDRVDAALLYSQRRGHETESAGKRGYPVEGAGSGANIRGSARGIPDPSQ    250
HMBRC    SNDRVDAALLYSQRRGHETESAGKRGYPVEGAGSGANIRGSARGIPDPSQ    250
HMBRMS11 SNDRVDAALLYSQRRGHETESAGERGYPVEGAGSGAIIRGSSRGIPDPSK    250
         ***************.****************.********* *********.

HMBRA    HKYHNFLGKIAYQINDNHRIGASLNGQQGHNYTVEESYNLTASSWREADD    300
HMBRB    HKYHSFLGKIAYQINDNHRIGASLNGQQGHNYTVEESYNLLASYWREADD    300
HMBRC    HKYHSFLGKIAYQINDNHRIGASLNGQQGHNYTVEESYNLLASYWREADD    300
HMBRMS11 HKYHNFLGKIAYQINDKHRIGPSFNGQQGHNYTIEESYNLTASSWREADD    300
         ****.***********.****.*.*********.******.**.******

HMBRA    VNRRRNANLFYEWMPDSNWLSSLKADFDYQKTKVAAIN-KGSFPT-NYTT    348
HMBRB    VNRRRNTNLFYEWTPESDRLSMVKADVDYQKTKVSAVNYKGSFPT-NYTT    349
HMBRC    VNRRRNTNLFYEWTPESDRLSMVKADVDYQKTKVSAVNYKGSFPIEDSST    350
HMBRMS11 VNRRRNANLFYEWTPDSNWLSSLKADFDYQTTKVAAVNNKGSFPTD-YST    349
         ******:*******.*:*:.*.::***.****::**:*.: .****  **

HMBRA    WETEYHKKEVGEIYNRSMDTRFKRFTLRLDSHPLQLGGGRHRLSFKTFAS    398
HMBRB    WETEYHKKEVGEIYNRSMDTTFKRITLRLMDSHPLQLGGGRHRLSFKTFAG    399
HMBRC    LTRNYQKDLDEIYNRSMDTRFKRITLRLDSHPLQLGGGRHRLSFKTFAS    400
HMBRMS11 WTRNYQKDLENIYNRSMDTRFKRFTLRMDSQPLQLGG-RHRLSLKTFAS    398
         : :.::*:: .*********.***:***:**:***** ****.****.
```

FIG. 11C

```
HMBRA     RRDFENLNRDDYYFSGRVVRTTSSIQHPVKTTNYGFSLSDQIQWNDVFSS  448
HMBRB     QRDFENLNRDDYYFSGRVVRTTNSIQHPVKTTNYGFSLSDQIQWNDVFSS  449
HMBRC     RRDFENLNRDDYYFSGRVVRTTSSIQHPVKTTNYGFSLSDQIQWNDVFSS  450
HMBRMS11  RREFENLNRDDYYFSERVSRTTSSIQHPVKTTNYGFSLSDQIQWNDVFSS  448
          .*.*************.**.***.**************************

HMBRA     RAGIRYDHTKMTPQELNAECHACDKTPPAANTYKGWSGFVGLAAQLNQAW  498
HMBRB     RAGIRYDHTKMTPQELNADCHACDKTPPAANTYKGWSGFVGLAAQLSQTW  499
HMBRC     RAGIRYDHTKMTPQELNAECHACDKTPPAANTYKGWSGFVGLAAQLNQAW  500
HMBRMS11  RADIRYDHTKMTPQELNADCHACDKTPPAANTYKGWSGFVGLAAQLNQAW  498
          **.***************.*******************************.*.*

HMBRA     RVGYDITSGYRVPNASEVYFETYNHGSGNWLPNPNLKAERSTTHTLSLQGR  548
HMBRB     RVGYDVTSGFRVPNASEVYFETYNHGSGTWKPNPNLKAERSTTHTLSLQGR  549
HMBRC     RVGYDITSGYRVPNASEVYFETYNHGSGNWLPNPNLKAERTTTHTLSLQGR  550
HMBRMS11  HVGYDITSGYRVPNASEVYFETYNHGSGNWLPNPNLKAERSTTHTLSLQGR  548
          .****.***.****************.*.*********..*********

HMBRA     SEKGMLDANLYQSNYRNFLSEEQKLTTSGTPGCTEENAYYSICSDPYKEK  598
HMBRB     GDKGTLDANLYQSNYRNFLSEEQNLTVSGTPGCTEEDAYYYRCSDPYKEK  599
HMBRC     SEKGTLDANLYQSNYRNFLSEEQKLTTSGDVSCTQMNYYGMCSNPYSEK   600
HMBRMS11  SEKGTLDANLYQNNYRNFLSEEQNLTTSGDVGCTQMNYYYGMCSNPYSEK  598
          .***.*******.*********.**.**  *     **  *.**** **
```

FIG. 11D

```
HMBRA     LDWQMKNIDKARIRGIELTGRLNVDKVASFVPEGWKLFGSLGYAKSKLSG  648
HMBRB     LDWQMKNIDKARIRGIELTGRLNVDKVASFVPEGWKLFGSLGYAKSKLSG  649
HMBRC     LDWQMQNIDKARIRGLELTGRLNVDKVASFVPEGWKLFGSLGYAKSKLSG  650
HMBRMS11  PEWQMQNIDKARIRGLELTGRLNVTKVASFVPEGWKLFGSLGYAKSKLSG  648
          .***.*.*********.**********.*********************

HMBRA     DNSLLSTQPLKVIAGIDYESPSEKWGVFSRLTYLGAKKVKDAQYTVYENK  698
HMBRB     DNSLLSTQPLKVIAGIDYESPSEKWGVFSRLTYLGAKKVKDAQYTVYENK  699
HMBRC     DNSLLSTQPLKVIAGIDYESPSEKWGVFSRLTYLGAKKVKDAQYTVYENK  700
HMBRMS11  DNSLLSTQPPKVIAGVDYESPSEKWGVFSRLTYLGAKKAKDAQYTVYENK  698
          *********.****.**************.*******.***********

HMBRA     GWGTPLQKKVKDYPWLNKSAYVFDMYGFYKPVKNLTLRAGVYNLFNRKYT  748
HMBRB     GWGTPLQKKVKDYPWLNKSAYVFDMYGFYKPAKNLTLRAGVYNLFNRKYT  749
HMBRC     GWGTPLQKKVKDYPWLNKSAYVFDMYGFYKPVKNLTLRAGVYNVFNRKYT  750
HMBRMS11  GRGTPLQKKVKDYPWLNKSAYVFDMYGFYKLAKNLTLRAGVYNVFNRKYT  748
          *.****************************  .*********** ****

HMBRA     TWDSLRGLYSYSTTNAVDRDGKGLDRYRAPGRNYAVSLEWKF  790
HMBRB     TWDSLRGLYSYSTTNAVDRDGKGLDRYRAPGRNYAVSLEWKF  791
HMBRC     TWDSLRGLYSYSTTNSVDRDGKGLDRYRAPSRNYAVSLEWKF  792
HMBRMS11  TWDSLRGLYSYSTTNAVDRDGKGLDRYRASGRNYAVSLDWKF  790
          ***************.************ .******.***
```

HEMOGLOBIN RECEPTORS FROM NEISSERIAE

This application is a U.S. National Phase application filed under 35 U.S.C. §371 of International Application No. PCT/US95/13623, filed Oct. 17, 1995, which claims priority to U.S. Ser. No. 08/537,361, filed Oct. 2, 1995 and U.S. Ser. No. 08/326,670, filed Oct. 18, 1994 now U.S. Pat. No. 5,698,438, issued Dec. 16, 1997.

This invention was made with government support under National Institute of Health grants R01 AM32493 and R01 AM22933. The U.S. government has certain rights to this invention.

BACKGROUND OF THE INVENTION

1. Field of the Invention

This invention relates to hemoglobin receptor genes and the proteins encoded therefrom of certain bacterial species, particularly species of Neisseria bacteria. More particularly, this invention relates to hemoglobin receptor genes, polypeptides and peptides useful for preparing vaccines and antibodies against Neisseria, and methods and means for producing such peptides and polypeptides in vitro. Also provided are diagnostic and therapeutic methods and reagents useful in detecting and treating Neisseria infection and methods for developing novel and effective anti-Neisseria agents.

2. Background of the Invention

The Neisseriae comprise a genus of bacteria that includes two gram-negative species of pyogenic cocci pathogenic for humans: *Neisseria meningitidis* and *Neisseria gonorrhoeae*. *N. meningitidis* is a major cause of bacterial meningitis in humans, especially children. The disease characteristically proceeds from asymptomatic carriage of the bacterium in the nasopharynx to invasion of the bloodstream and cerebrospinal fluid in susceptible individuals.

*N. meningitidis* is one of the leading causes of bacterial meningitis in children and healthy adults in the world. The severity of the disease is evidenced by the ability of meningococci to cause the death of previously healthy individuals in less than 24 hours. *N. meningitidis* has a polysaccharide capsule whose diversity of component antigenic polysaccharide molecules has resulted in the classification of ten different serogroups. Of these, group A strains are the classic epidemic strains; group B and C are generally endemic strains, but C occasionally causes an epidemic outbreak. All known group A strains have the same protein antigens on their outer membranes, while group B strains have a dozen serotypes or groupings based on the presence of principal outer membrane protein antigens (as opposed to polysaccharides).

Survival of a pathogen such as *N. meningitidis* in a host depends on its ability to overcome a battery of host defense mechanisms. One nonspecific host defense mechanism against microbial intruders is to limit the availability of iron in tissues (Weinberg, 1984, *Physiological. Rev.* 64: 65–102), because iron is a necessary nutrient for most microbial pathogens. The vast majority of iron in the human adult is located intracellularly in the form of hemoglobin (76%) or ferritin (23%). The remainder can be found extracellularly bound to host iron-binding proteins such as transferrin and lactoferrin (Otto et al., 1992, *Crit. Rev. Microbiol.* 18: 217–233).

Pathogenic bacteria have adapted to this iron-limiting environment by developing highly specific and effective iron assimilation systems. A large number of these bacteria secrete siderophores, small, non-protein iron chelators which, due to their extremely high affinity for iron (III), scavenge trace amounts of iron(III) from the environment and shuttle the iron back to the bacterial cell (Baggs and Neilands, 1987, *Microbiol. Rev.* 51: 509–518; Braun and Hantke, 1991, in Winkelmann (ed.), *Handbook of Microbial Iron Chelates*, CRC Press: Boca Raton, Fla., pp. 107–138.).

Alternatively, some bacterial pathogens, like Neisseriae species (Archilbald and DeVoe, 1979, *FEMS Microbiol. Lett.* 6: 159–162; Mickelson et al., 1982, *Infect. Immun.* 35: 915–920; Dyer et al., 1987, *Infect. Immun.* 55: 2171–2175), *Haemophilus influenzae* (Coulton and Pang, 1983, *Curr. Microbiol.* 9: 93–98; Schryvers, 1988, *Mol. Microbiol.* 2: 467472; Jarosik et al., 1994, *Infect. Immun.* 62: 24702477), *Vibrio cholerae* (Stoebner and Payne, 1988, *Infect. Immun.* 56:2891–2895; Henderson and Payne, 1994, *J. Bacteriol.* 176: 3269–3277), Yersiniae (Stojiljkovic and Hantke, 1992, *EMBO J.* 11: 4359–4367) and *Actinobacillus pleuropneumoniae* (Gerlach et al., 1992, *Infect. Immun.* 60: 3253–3261) have evolved more sophisticated mechanisms to sequester iron from the host. These pathogens can directly bind host's iron-binding proteins such as lactoferrin, transferrin, and heme-containing compounds, and use them as sole sources of iron.

The importance of iron in the virulence of *N. meningitidis* was demonstrated by in vivo studies using mice as the animal model system (Calver et al., 1976, *Can. J. Microbiol.* 22: 832–838; Holbien et al., 1981, *Infect. Immun.* 34: 120–125). Specific iron-regulated outer membrane receptors have been shown to be involved in the binding and the utilization of lactoferrin- and transferrin-iron in Neisseriae (Schryvers and Morris, 1988, *Infect. Immun.* 56: 1144–1149 and *Mol. Microbiol.* 2:281–288; Legrain et al., 1993, *Gene* 130: 81–90; Pettersson et al., 1993, *Infect. Immun.* 61: 47244733 and 1994, *J. Bacteriol.* 176: 1764–1766). These receptors share significant amino acid similarity and, most probably, also the mechanism of iron internalization, with receptors for siderophores and vitamin B12 of other Gram-negative bacteria (Cornelissen et al., 1993, *J. Bacteriol.* 174: 5788–5797). In contrast, the mechanism by which Neisseriae utilize hemoglobin- and hemin-iron as well as the components involved have so far not been described.

Recently, several proteins with hemoglobin-binding and/or hemin-binding activities have been identified in total membranes of iron-limited *N. meningitidis* and *N. gonorrhoeae*.

Lee and Hill, 1992, *J. gen. Microbiol.* 138: 2647–2656 disclose the specific hemoglobin binding by isolated outer membranes of *N. meningitidis*.

Martek and Lee, 1994, *Infect. Immun.* 62: 700–703 disclosed that acquisition of heme iron by *N. meningitidis* does not involve meningococcal transferrin-binding proteins.

Lee, 1994, *Microbiol.* 140: 1473–1480 describes the biochemical isolation and characterization of hemin binding proteins from *N. meningitidis*.

The precise role of these proteins in hemin and/or hemoglobin utilization remains unclear at present, although these proteins are likely to be components of a hemin-utilization system in *N. meningitidis*.

The dependence on host iron stores for Neisseria growth is a potentially useful route towards the development of novel and effective therapeutic intervention strategies. Historically, infections of both *N. meningitidis* and *N. gonorrhoeae* were treated chemoprophylactically with sulfonamide drugs. However, with the development of sulfonamide-resistant strains came the necessity of using alternative modes of therapy such as antibiotic treatment. More recently, the drug treatment of choice includes the administration of high grade penicillin. However, the success of antimicrobial treatment is decreased if therapy is not initiated early after infection.

Gonococcal infection has also been treated with penicillin, ampicillin, or amoxicillin, tetracycline hydrochloride, and spectinomycin. Unfortunately, because the incidence of infections due to penicillinase-producing bacteria has increased, several new, more expensive β-lactam antibiotics have been used in treatment. Despite the fact that existing antibiotics have decreased the serious consequences of gonorrhea, their use has not lowered the incidence of the infection in the general population.

Prevention of meningococcal disease has been attempted by chemoprophylaxis and immunoprophylaxis. At present, rifampin and minocycline are used, but only for humans in close contact with an infected person as this treatment has a number of disadvantages. The only commercially available vaccine against meningococcal meningitis has as its major component the bacterial polysaccharide capsule. In adults this vaccine protects against serogroups A, C, Y and W135. It is not effective against serogroup B, and is ineffective in children against serogroup C. Thus far, immunoprophylatic preventive treatment has not been available for *N. gonorrhoeae*.

Thus, what is needed are better preventative therapies for meningococcal meningitis and gonorrhea including more effective, longer lasting vaccines which protect across all of the serogroups of *N. meningitidis* and all the serotypes of *N. gonorrhoeae*. In addition, better methods are need to treat meningococcal and gonococcal infection.

SUMMARY OF THE INVENTION

The present invention relates to the cloning, expression and functional characterization of genes encoding bacterial hemoglobin receptor proteins. Specifically, the invention relates to genes encoding hemoglobin receptor proteins from Neisseria species, in particular *N. meningitidis* and *N. gonorrhoeae*. The invention comprises species of nucleic acids having a nucleotide sequence encoding novel bacterial hemoglobin receptor proteins. Also provided by this invention is the deduced amino acid sequence of the cognate hemoglobin receptor proteins of these bacterial genes.

The invention provides nucleic acids, nucleic acid hybridization probes, recombinant expression constructs capable of expressing the hemoglobin receptor protein of the invention in cultures of transformed cells, preferably bacterial cells, and such cultures of transformed bacterial cells that express the hemoglobin receptor proteins of the invention. The invention also provides gene knockout vectors for inactivating the hemoglobin receptor protein gene in cells, particularly cells of Neisseria species, via, for example, homologous recombination and other mechanisms, and cultures of such hemoglobin receptor protein null mutant cells.

The invention also provides homogeneous preparations of the bacterial hemoglobin receptor proteins of the invention, as well as antibodies against and epitopes of the hemoglobin receptor protein. Methods for characterizing this receptor protein and methods for using the protein in the development of agents having pharmacological uses related to this receptor, particularly bactericidal and bacteriostatic uses, are also provided by the invention.

In other embodiments of this invention are provided diagnostic methods and reagents encompassing the use of the anti-Neisseria hemoglobin receptor protein antibodies of the invention. Still further embodiments provided herein include therapeutic methods and reagents encompassing the use of the anti-Neisseria hemoglobin receptor protein antibodies of the invention. Even more embodiments include diagnostic methods and reagents encompassing the use of the Neisseria hemoglobin receptor protein-encoding nucleic acids of the invention, as sensitive probes for the presence of Neisseria infection using nucleic acid hybridization techniques and/or in vitro amplification methodologies. Yet additional embodiments of the invention include therapeutic methods and reagents encompassing the use of the Neisseria hemoglobin receptor protein-encoding nucleic acids of the invention, comprising recombinant expression constructs engineered to produce antisense transcripts of the Neisseria hemoglobin receptor gene and fragments thereof, as well as recombinant knockout vectors of the invention. The invention also provides the Neisseria hemoglobin receptor protein and epitopes thereof as components of vaccines for the development of non-disease associated immunity to pathological infection with bacteria of Neisseria species.

In a first aspect, the invention provides a nucleic acid having a nucleotide sequence encoding a bacterial hemoglobin receptor protein gene. In a preferred embodiment, the bacterial hemoglobin receptor protein gene is isolated from bacteria of Neisseria species. In a particularly preferred embodiment, the hemoglobin receptor protein gene is isolated from *Neisseria meningitidis*, serotype C. In a particular example of this embodiment, the nucleic acid comprises a 3.3 kilobase (kb) BamHI/HindIII fragment of *N. meningitidis* genomic DNA. In this embodiment, the nucleotide sequence comprises an open reading frame of 2376 nucleotides of *N. meningitidis* genomic DNA encoding 792 amino acids comprising the hemoglobin receptor gene. In this embodiment of the invention, the nucleotide sequence of the *N. meningitidis* hemoglobin receptor gene is the sequence depicted in FIGS. 2A–2H (SEQ ID No:1). It will be understood that the *N. meningitidis* gene as disclosed herein is defined, insofar as is necessary, by the amino acid sequence of the protein encoded therein, said amino acid sequence being represented in FIGS. 2A–2H (SEQ. ID No.:2). Thus, it will be understood that the particular nucleotide sequence depicted in FIGS. 2A–2H (SEQ. ID. No.:1) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding *N. meningitidis* hemoglobin receptor protein disclosed herein.

In another particularly preferred embodiment of this aspect of the invention, the hemoglobin receptor protein gene is isolated from *Neisseria meningitidis*, serotype B. In a particular example of this embodiment, the nucleic acid comprises a 2376 basepair (bp) polymerase chain reaction-amplified fragment of *N. meningitidis*, serotype B genomic DNA. In this embodiment, the nucleotide sequence comprises an open reading frame of 2373 nucleotides of *N. meningitidis* genomic DNA encoding 791 amino acids comprising the hemoglobin receptor gene. In this embodiment of the invention, the nucleotide sequence of the *N. meningitidis* hemoglobin receptor gene is the sequence depicted in FIGS. 7A–7I (SEQ ID No:3). It will be understood that the *N.*

*meningitidis* gene as disclosed herein is defined, insofar as is necessary, by the amino acid sequence of the protein encoded therein, said amino acid sequence being represented in FIGS. 7A–7I (SEQ. ID No.:4). Thus, it will be understood that the particular nucleotide sequence depicted in FIGS. 7A–7I (SEQ. ID. No.:3) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding *N. meningitidis* hemoglobin receptor protein disclosed herein.

In another particularly preferred embodiment of this aspect of the invention, the hemoglobin receptor protein gene is isolated from *Neisseria meningitidis*, serotype A. In a particular example of this embodiment, the nucleic acid comprises a 2373 basepair (bp) polymerase chain reaction-amplified fragment of *N. meningitidis*, serotype A genomic DNA. In this embodiment, the nucleotide sequence comprises an open reading frame of 2370 nucleotides of *N. meningitidis* genomic DNA encoding 790 amino acids comprising the hemoglobin receptor gene. In this embodiment of the invention, the nucleotide sequence of the *N. meningitidis* hemoglobin receptor gene is the sequence depicted in FIGS. 8A–8I (SEQ ID No:5). It will be understood that the *N. meningitidis* gene as disclosed herein is defined, insofar as is necessary, by the amino acid sequence of the protein encoded therein, said amino acid sequence being represented in FIGS. 8A–8I (SEQ. ID No.:6). Thus, it will be understood that the particular nucleotide sequence depicted in FIGS. 8A–8I (SEQ. ID. No.:5) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding *N. meningitidis* hemoglobin receptor protein disclosed herein.

In yet other preferred embodiments, the invention provides nucleic acid encoding a hemoglobin receptor protein gene isolated from *Neisseria gonorrhoeae*. In a particular example of this embodiment, the nucleic acid comprises a 2378 basepair (bp) polymerase chain reaction-amplified fragment of *N. gonorrhoeae* genomic DNA. In this embodiment, the nucleotide sequence comprises an open reading frame of 2370 nucleotides of *N. gonorrhoeae* genomic DNA encoding 790 amino acids comprising the hemoglobin receptor gene. In this embodiment of the invention, the nucleotide sequence of the *N. gonorrhoeae* hemoglobin receptor gene is the sequence depicted in FIGS. 9A–9I (SEQ ID No:7). It will be understood that the *N. gonorrhoeae* gene as disclosed herein is defined, insofar as is necessary, by the amino acid sequence of the protein encoded therein, said amino acid sequence being represented in FIGS. 9A–9I (SEQ. ID No.:8). Thus, it will be understood that the particular nucleotide sequence depicted in FIGS. 9A–9I (SEQ. ID. No.:7) is but one of a number of equivalent nucleotide sequences that encode the hemoglobin receptor protein, due to the degeneracy of the genetic code, and that all such alternative, equivalent nucleotide sequences are hereby explicitly encompassed within the disclosed nucleotide sequences of the invention. Also included herein are any mutant or allelic variations of this nucleotide sequence, either naturally occurring or the product of in vitro chemical or genetic modification. Each such variant will be understood to have essentially the same nucleotide sequence as the nucleotide sequence of the corresponding *N. gonorrhoeae* hemoglobin receptor protein disclosed herein.

The invention also provides bacterial hemoglobin receptor proteins. In a preferred embodiment, the bacterial hemoglobin receptor protein is isolated from bacteria of Neisseria species. In a particularly preferred embodiment, the hemoglobin receptor protein is isolated from *Neisseria meningitidis*. In a particular example of this embodiment, the protein is derived from *N. meningitidis*, serotype C and comprises an amino acid sequence of 792 amino acids. In this embodiment of the invention, the amino acid sequence of the *N. meningitidis*, serotype C hemoglobin receptor protein is the sequence depicted in FIGS. 2A–2H (SEQ ID No:2). In another example of this embodiment, the protein is derived from *N. meningitidis*, serotype B and comprises an amino acid sequence of 791 amino acids. In this embodiment of the invention, the amino acid sequence of the *N. meningitidis*, serotype B hemoglobin receptor protein is the sequence depicted in FIGS. 7A–7I (SEQ ID No:4). In yet another example of this embodiment, the protein is derived from *N. meningitidis*, serotype A and comprises an amino acid sequence of 790 amino acids. In this embodiment of the invention, the amino acid sequence of the *N. meningitidis*, serotype A hemoglobin receptor protein is the sequence depicted in FIG. 8A–8I (SEQ ID No:6). The invention also provides hemoglobin receptor protein derived from *N. gonorrhoeae*.In this embodiment of the invention, the protein comprises an amino acid sequence of 790 amino acids, and the amino acid sequence of the *N. gonorrhoeae* hemoglobin receptor protein is the sequence depicted in FIGS. 9A–9I (SEQ ID No:8). Also explicitly encompassed within the scope of this invention are related bacterial hemoglobin receptor proteins, particularly such proteins isolated from Neisseria species, having essentially the same amino acid sequence and substantially the same biological properties as the hemoglobin receptor protein encoded by the *N. meningitidis* and *N. gonorrhoeae* nucleotide sequences described herein.

In another aspect, the invention provides a homogeneous preparation of an approximately 85.5 kiloDalton (kD) bacterial hemoglobin receptor protein or derivative thereof, said size being understood to be the size of the protein before any post-translational modifications thereof. Also provided is a 90 kD embodiment of the receptor as determined by sodium dodecyl sulfate/polyacrylamide gel electrophoresis under reducing conditions. In a preferred embodiment, the bacterial hemoglobin receptor protein is isolated from bacteria of Neisseria species. In a particularly preferred embodiment, the hemoglobin receptor protein is isolated from *Neisseria meningitidis*. In one embodiment of this aspect of the invention, the protein is isolated from *N. meningitidis*, serotype C and the amino acid sequence of the bacterial hemoglobin receptor protein or derivative thereof preferably is the amino acid sequence of the hemoglobin receptor protein shown in FIGS. 2A–2H (SEQ ID No:2). In a second embodiment of this aspect of the invention, the protein is isolated from *N. meningitidis*, serotype B and the amino acid sequence of the bacterial hemoglobin receptor protein or derivative thereof preferably is the amino acid sequence of the hemoglobin receptor protein shown in FIGS. 7A–7I (SEQ ID No:4). In a third embodiment of this aspect of the invention, the protein is isolated from *N. meningitidis*, serotype A and the amino acid sequence of the bacterial hemoglobin receptor protein or derivative thereof preferably is the amino acid sequence of the hemoglobin receptor protein shown in FIGS. 8A–8I (SEQ ID No:6). The invention also provides a homogeneous preparation of a bacterial hemoglobin receptor protein isolated from *N. gonorrhoeae*. In a preferred embodiment, the amino acid sequence of the bacterial hemoglobin receptor protein or derivative thereof preferably is the amino acid sequence of the hemoglobin receptor protein shown in FIGS. 9A–9I (SEQ ID No:8).

This invention provides nucleotide probes derived from the nucleotide sequences herein provided. The invention includes probes isolated from either complementary DNA (cDNA) copies of bacterial messenger RNA (mRNA) or bacterial genomic DNA (gDNA), as well as probes made synthetically or by in vitro amplification methods using the sequence information provided herein. The invention specifically includes but is not limited to oligonucleotide, nick-translated, random primed, or in vitro amplified probes made using cDNA or genomic clones embodying the invention, and oligonucleotide and other synthetic probes synthesized chemically using the nucleotide sequence information of cDNA or genomic clone embodiments of the invention.

It is a further object of this invention to provide such nucleic acid hybridization probes to detect the presence of bacteria of Neisseria species, particularly *N. meningitidis* and *N. gonorrhoeae*, in a biological sample in the diagnosis of a Neisseria infection in a human. Such a biological sample preferably includes blood, urine, semen, mucus, cerebrospinal fluid, peritoneal fluid and ascites fluids, as well as cell scrapings from the epithelium of the mouth, urethra, anus and rectum, and other organs.

The present invention also includes peptides encoded by the nucleotide sequences comprising the nucleic acid embodiments of the invention. The invention includes either naturally occurring or synthetic peptides which may be used as antigens for the production of hemoglobin receptor protein-specific antibodies. The invention also comprises such antibodies, preferably monoclonal antibodies, and cells and cultures of cells producing such antibodies.

Thus, the invention also provides antibodies against and epitopes of bacterial hemoglobin receptor proteins of the invention. It is an object of the present invention to provide antibodies that are immunologically reactive to the bacterial hemoglobin receptor proteins of the invention. It is a particular object to provide monoclonal antibodies against these bacterial hemoglobin receptor proteins. In a preferred embodiment, antibodies provided are raised against bacterial hemoglobin receptor protein isolated from bacteria of Neisseria species. In a particularly preferred embodiment, such antibodies are specific for the hemoglobin receptor protein isolated from *N. meningitidis* serotypes A, B or C. In additional particularly preferred embodiment, such antibodies are specific for the hemoglobin receptor protein isolated from *Neisseria gonorrhoeae*.

Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with purified hemoglobin receptor protein or a cell expressing antigens or epitopes of bacterial hemoglobin receptor proteins of the invention. The present invention also provides hybridoma cell lines that produce such antibodies, and can be injected into a living mouse to provide an ascites fluid from the mouse that is comprised of such antibodies. In a preferred embodiment, antibodies provided are raised against bacterial hemoglobin receptor protein isolated from bacteria of Neisseria species. In a particularly preferred embodiment, such antibodies are specific for the hemoglobin receptor protein isolated from *Neisseria meningitidis*, serotypes A, B or C. In additional particularly preferred embodiment, such antibodies are specific for the hemoglobin receptor protein isolated from *Neisseria gonorrhoeae*.

It is a further object of the invention to provide immunologically-active epitopes of the bacterial hemoglobin receptor proteins of the invention. Chimeric antibodies immunologically reactive against the bacterial hemoglobin receptor proteins of the invention are also within the scope of this invention. In a preferred embodiment, antibodies and epitopes provided are raised against or derived from bacterial hemoglobin receptor protein isolated from bacteria of Neisseria species. In a particularly preferred embodiment, such antibodies and epitopes are specific for the hemoglobin receptor protein isolated from *Neisseria meningitidis*, serotypes A, B or C. In additional particularly preferred embodiment, such antibodies and epitopes are specific for the hemoglobin receptor protein isolated from *Neisseria gonorrhoeae*.

The present invention provides recombinant expression constructs comprising a nucleic acid encoding a bacterial hemoglobin receptor protein wherein the construct is capable of expressing the encoded hemoglobin receptor protein in cultures of cells transformed with the construct. Preferred embodiments of such constructs comprise the *N. meningitidis*, serotype C hemoglobin receptor gene depicted in FIGS. 2A–2H (SEQ ID No.:1), such constructs being capable of expressing the bacterial hemoglobin receptor protein encoded therein in cells transformed with the construct. Additional preferred embodiments of such constructs comprise the *N. meningitidis*, serotype B hemoglobin receptor gene depicted in FIGS. 7A–7I (SEQ ID No.:3), such constructs being capable of expressing the bacterial hemoglobin receptor protein encoded therein in cells transformed with the construct. Further additional preferred embodiments of such constructs comprise the *N. meningitidis*, serotype A hemoglobin receptor gene depicted in FIGS. 8A–8I (SEQ ID No.:5), such constructs being capable of expressing the bacterial hemoglobin receptor protein encoded therein in cells transformed with the construct. The invention also provides recombinant expression constructs encoding a hemoglobin receptor protein gene isolated from *N. gonorrhoeae*. In a particularly preferred embodiment, such constructs comprise the *N. gonorrhoeae* hemoglobin receptor gene depicted in FIGS. 9A–9I (SEQ ID No.:7), the constructs being capable of expressing the bacterial hemoglobin receptor protein encoded therein in cells transformed with the construct.

The invention also provides cultures of cells, preferably bacterial cells, having been transformed with the recombinant expression constructs of the invention, each such cultures being capable of and in fact expressing the bacterial hemoglobin receptor protein encoded in the transforming construct.

The present invention also includes within its scope protein preparations of prokaryotic cell membranes containing the bacterial hemoglobin receptor protein of the invention, derived from cultures of prokaryotic cells transformed with the recombinant expression constructs of the invention.

The invention also provides diagnostic reagents and methods for using such reagents for detecting the existence of an infection in a human, with bacteria of a Neisseria species. In preferred embodiments, such diagnostic reagents comprise antibodies that are immunologically reactive with a bacterial hemoglobin receptor protein. In a preferred embodiment, such antibodies are raised against a bacterial hemoglobin receptor protein isolated from bacteria of Neisseria species. In a particularly preferred embodiment, such antibodies are specific for the hemoglobin receptor protein isolated from *Neisseria meningitidis*, serotypes A, B or C. In additional particularly preferred embodiments, such antibodies are specific for the hemoglobin receptor protein isolated from *Neisseria gonorrhoeae*.

In yet another embodiment of this aspect of the invention are provided diagnostic reagents and methods for using such reagents wherein said reagents are nucleic acid hybridization probes comprising a bacterial hemoglobin receptor gene. In a preferred embodiment, the bacterial hemoglobin receptor protein gene is isolated from bacteria of Neisseria species. In a particularly preferred embodiment, the hemoglobin receptor protein gene is isolated from *Neisseria meningitidis*. In particular examples of this embodiment of the invention, the nucleic acid probes comprise a specifically-hybridizing fragment of a 3.3 kilobase (kb) BamHI/HindIII fragment of *N. meningitidis*, serotype C genomic DNA. In this embodiment, the nucleotide sequence comprises all or a specifically-hybridizing fragment of an open reading frame of 2376 nucleotides of *N. meningitidis*, serotype C genomic DNA encoding 792 amino acids comprising the hemoglobin receptor gene. In this embodiment of the invention, the nucleotide sequence of the *N. meningitidis*, serotype C hemoglobin receptor gene is the sequence depicted in FIGS. 2A–2H (SEQ ID No:1). In another example of this embodiment of the invention, the nucleic acid probes comprise a specifically-hybridizing fragment of a 2376 bp, polymerase chain reaction-amplified fragment of *N. meningitidis*, serotype A genomic DNA. In this embodiment, the nucleotide sequence comprises all or a specifically-hybridizing fragment of an open reading frame of 2373 nucleotides of *N. meningitidis*, serotype B genomic DNA encoding 791 amino acids comprising the hemoglobin receptor gene. In this embodiment of the invention, the nucleotide sequence of the *N. meningitidis*, serotype A hemoglobin receptor gene is the sequence depicted in FIGS. 7A–7I (SEQ ID No:3). In yet another example of this embodiment of the invention, the nucleic acid probes comprise a specifically-hybridizing fragment of a 2373 bp, polymerase chain reaction-amplified fragment of *N. meningitidis*, serotype A genomic DNA. In this embodiment, the nucleotide sequence comprises all or a specifically-hybridizing fragment of an open reading frame of 2370 nucleotides of *N. meningitidis*, serotype A genomic DNA encoding 790 amino acids comprising the hemoglobin receptor gene. In this embodiment of the invention, the nucleotide sequence of the *N. meningitidis*, serotype A hemoglobin receptor gene is the sequence depicted in FIGS. 8A–8I (SEQ ID No:5). The invention also provides nucleic acid hybridization probes comprising a bacterial hemoglobin receptor gene isolated from *N. gonorrhoeae*. In a preferred embodiment of this aspect of the invention, the nucleic acid probes comprise a specifically-hybridizing fragment of a 2378 bp, polymerase chain reaction-amplified fragment of *N. gonorrhoeae* genomic DNA. In this embodiment, the nucleotide sequence comprises all or a specifically-hybridizing fragment of an open reading frame of 2370 nucleotides of *N. gonorrhoeae* genomic DNA encoding 790 amino acids comprising the hemoglobin receptor gene. In this embodiment of the invention, the nucleotide sequence of the *N. gonorrhoeae* hemoglobin receptor gene is the sequence depicted in FIGS. 9A–9I (SEQ ID No:7). It will be understood that the term "specifically-hybridizing" when used to describe a fragment of a nucleic acid encoding a bacterial hemoglobin receptor gene is intended to mean that nucleic acid hybridization of such a fragment is stable under high stringency conditions of hybridization and washing as the term "high stringency" would be understood by those having skill in the molecular biological arts.

Also provided by the invention are therapeutic agents and methods for using such agents for treating the an infection in a human, with bacteria of a Neisseria species. In preferred embodiments, such agents comprise antibodies that are immunologically reactive with a bacterial hemoglobin receptor protein. In a preferred embodiment, such antibodies are raised against a bacterial hemoglobin receptor protein isolated from bacteria of Neisseria species. In a particularly preferred embodiment, such antibodies are specific for the hemoglobin receptor protein isolated from *Neisseria meningitidis*, serotypes A, B or C. In additional preferred embodiments, such antibodies are specific for the hemoglobin receptor protein isolated from *Neissena gonorrhoeae*. Therapeutic agents provided in this aspect of the invention comprise such antibodies in a pharmaceutically-acceptable carrier, along with appropriate adjuvants and the like. In additional embodiments, such antibodies are covalently conjugated to a bactericidal or bacteriostatic agent effective against bacteria of Neisseria species, preferably *N. meningitidis* and *N. gonorrhoeae*.

In yet another embodiment of this aspect of the invention are provided therapeutic reagents and methods for using such reagents wherein said reagents comprise recombinant expression constructs of the invention, or a homologue thereof that expresses the nucleic acid encoding a hemoglobin receptor in an antisense orientation. In a preferred embodiment, the bacterial hemoglobin receptor protein gene is isolated from bacteria of Neisseria species. In a particularly preferred embodiment, the hemoglobin receptor protein gene is isolated from *Neisseria meningitidis*. In particular examples of this embodiment of the invention, the nucleic acids comprise a specifically-hybridizing fragment of a 3.3 kilobase (kb) BamHI/HindIII fragment of *N. meningitidis*, serotype C genomic DNA. In this embodiment, the nucleotide sequence comprises all or a specifically-hybridizing fragment of an open reading frame of 2376 nucleotides of *N. meningitidis*, serotype C genomic DNA encoding 792 amino acids comprising the hemoglobin receptor gene. In this embodiment of the invention, the nucleotide sequence of the *N. meningitidis*, serotype C hemoglobin receptor gene is the sequence depicted in FIGS. 2A–2H (SEQ ID No:1). In another example of this embodiment of the invention, the nucleic acid probes comprise a specifically-hybridizing fragment of a 2376 bp, polymerase chain reaction-amplified fragment of *N. meningitidis*, serotype B genomic DNA. In this embodiment, the nucleotide sequence comprises all or a specifically-hybridizing fragment of an open reading frame of 2373 nucleotides of *N. meningitidis*, serotype B genomic DNA encoding 791 amino acids comprising the hemoglobin receptor gene. In this embodiment of the invention, the nucleotide sequence of the *N. meningitidis*, serotype B hemoglobin receptor gene is the sequence depicted in FIGS. 7A–7I (SEQ ID No:3). In yet another example of this embodiment of the invention, the nucleic acid probes comprise a specifically-hybridizing fragment of a 2373 bp, polymerase chain reaction-amplified fragment of N. meningitidis, serotype A genomic DNA. In this embodiment, the nucleotide sequence comprises all or a specifically-hybridizing fragment of an open reading frame of 2370 nucleotides of N. meningitidis, serotype A genomic DNA encoding 790 amino acids comprising the hemoglobin receptor gene. In this embodiment of the invention, the nucleotide sequence of the N. meningitidis, serotype A hemoglobin receptor gene is the sequence depicted in FIGS. 8A–8I (SEQ ID No:5). The invention also provides recombinant expression constructs of the invention, or a homologue thereof that expresses the nucleic acid encoding a hemoglobin receptor in an antisense orientation, wherein the nucleic acid encodes a bacterial hemoglobin receptor gene isolated from N. gonorrhoeae. In a preferred embodiment of this aspect of the invention, the nucleic acid probes comprise a specifically-hybridizing fragment of a 2378 bp, polymerase chain reaction-amplified fragment of N. gonorrhoeae genomic DNA. In this embodiment, the nucleotide sequence comprises all or a specifically-hybridizing fragment of an open reading frame of 2370 nucleotides of N. gonorrhoeae genomic DNA encoding 790 amino acids comprising the hemoglobin receptor gene. In this embodiment of the invention, the nucleotide sequence of the N. gonorrhoeae hemoglobin receptor gene is the sequence depicted in FIGS. 9A–9I (SEQ ID No:7).

The invention also provides a method for screening compounds for their ability to inhibit, facilitate or modulate the biochemical activity of a bacterial hemoglobin receptor protein of the invention, for use in the in vitro screening of novel agonist and antagonist compounds and novel bactericidal and bacteriostatic agents specific for the hemoglobin receptor protein. In preferred embodiments, cells transformed with a recombinant expression construct of the invention are contacted with such a compound, and the binding capacity of the compounds, as well as the effect of the compound on binding of other, known hemoglobin receptor agonists such as hemoglobin and hemin, and antagonists, is assayed. Additional preferred embodiments comprise quantitative analyses of such effects.

The present invention is also useful for the detection of bactericidal and/or bacteriostatic analogues, agonists or antagonists, known or unknown, of a bacterial hemoglobin receptor protein, preferably derived from bacteria of Neisseria species, most preferably isolated from N. meningitidis, wherein such compounds are either naturally occurring or embodied as a drug.

The invention also provides vaccines for immunizing a human against infection with pathogenic bacteria of Neisseria species, the vaccines comprising the hemoglobin binding proteins of the invention or antigenic fragments thereof. In a preferred embodiment, the vaccines of the invention comprise cells expressing a hemoglobin receptor binding protein of the invention, or an antigenic fragment thereof, preferably wherein said cells are attenuated varieties of cells adapted for growth in humans, i.e., wherein such cells are non-pathogenic and do not cause bactermia, endotoxemia or sepsis. Examples of such attenuated varieties of cells include attenuated strains of Salmonella species, for example Salmonella typhi and Salmonella typhimurium, as well as other attenuated bacterial species. Also provided by the invention are recombinant expression constructs as disclosed herein useful per se as vaccines, for introduction into an animal and production of an immunologic response to bacterial hemoglobin receptor protein antigens encoded therein.

Specific preferred embodiments of the present invention will become evident from the following more detailed description of certain preferred embodiments and the claims.

DESCRIPTION OF THE DRAWINGS

The foregoing and other objects of the present invention, the various features thereof, as well as the invention itself may be more fully understood from the following description, when read together with the accompanying drawings in which:

FIGS. 2A–2H illustrates the nucleotide (SEQ ID No.:1) and deduced amino acid (SEQ ID No.:2) sequences of the N. meningitidis hemoglobin receptor protein encoded in a 3.3 kb BamHI/HindIII DNA fragment.

FIGS. 4A–4C presents an amino acid sequence comparison between portions of the N. meningitidis transferrin receptor Tbp1 (SEQ ID No.:9), the N. meningitdis lactoferrin receptor LbpA (SEQ ID No.:10), and N. meningitidis hemoglobin receptor HmbR (SEQ ID No.:2).

FIG. 5 illustrates Southern hybridization analysis of chromosomal DNA from N. meningitidis 8013 and the MC8013hmbR mutant using a BamHI-SalI fragment of the hmb gene as probe labeled using a DIG nonradioactive DNA labelling and detection kit (Boehringer Mannheim Biochemicals, Indianapolis, Ind.). Lane 1 contains DNA from N. meningitidis strain MC8013, digested with ClaI; lane 2 is MC803hmbR DNA digested with ClaI; lane 3, is MC8013 DNA digested with BamHI and SalI; and lane 4 is MC8013hmbR DNA digested with BamHI and SalI.

FIGS. 7A–7I illustrates the nucleotide (SEQ ID No.:3) and deduced amino acid (SEQ ID No.:4) sequences of the N. meningitidis, serotype B hemoglobin receptor protein encoded on a 2376 bp polymerase chain reaction-amplified DNA fragment.

FIGS. 8A–8I illustrates the nucleotide (SEQ ID No.:5) and deduced amino acid (SEQ ID No.:6) sequences of the N. meningitidis, serotype A hemoglobin receptor protein encoded on a 2373 bp polymerase chain reaction-amplified DNA fragment.

FIGS. 9A–9I illustrates the nucleotide (SEQ ID No.:7) and deduced amino acid (SEQ ID No.:8) sequences of the N. gonorrhoeae hemoglobin receptor protein encoded on a 2376 bp polymerase chain reaction-amplified DNA fragment.

FIGS. 11A–11D presents an amino acid sequence comparison between the hemoglobin receptor proteins derived from N. meningitidis, serotypes B (SEQ ID No.:4), serotype A (SEQ ID No.:6) and serotype C (SEQ ID No.:2) and from N. gonorrhoeae (SEQ ID No.:8).

DETAILED DESCRIPTION OF THE PREFERRED EMBODIMENTS

Figure 1:
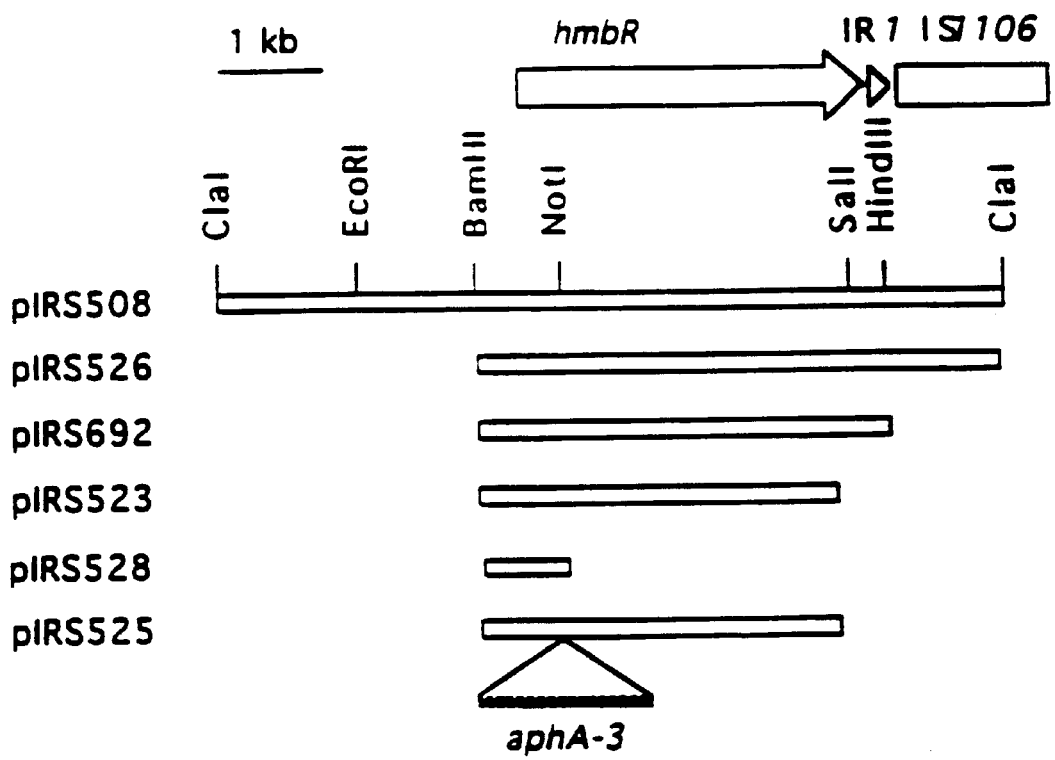
FIG. 1 is a schematic drawing of the restriction enzyme digestion map of a N. meningitidis cosmid clone and subclones thereof derived as described in Example 2.

The term "bacterial hemoglobin receptor" as used herein refers to bacterial proteins comprising the outer membrane of Gram negative bacteria, which specifically mediate transit of hemoglobin-derived hemin, as well as hemin from other sources, through the outer membrane of such bacteria and into the periplasmic space. The bacterial hemoglobin receptor proteins of the invention are characterized by, first, an amino acid sequence that is essentially the sequence depicted in FIGS. 2A–2H (SEQ ID No.:2), FIGS. 7A–7I (SEQ ID No.:4), FIGS. 8A–8I (SEQ ID No.:6) and FIGS. 9A–9I (SEQ ID No.:8). The bacterial hemoglobin receptor proteins of the invention are further characterized by having substantially the same biological activity as a protein having the amino acid sequence depicted in FIGS. 2A–2H (SEQ ID No.:2), FIGS. 7A–7I (SEQ ID No.:4), FIGS. 8A–8I (SEQ ID No.:6) and FIGS. 9A–9I (SEQ ID No.:8). This definition is intended to encompass naturally-occurring variants and mutant proteins, as well as genetically engineered variants made by man.

Cloned, isolated and purified nucleic acid provided by the present invention may encode a bacterial hemoglobin receptor protein of any Neisseria species of origin, including, most preferably, N. meningitidis species and serotypes thereof and Neisseria gonorhoeae species.

The nucleic acid hybridization probes provided by the invention comprise DNA or RNA having all or a specifically-hybridizing fragment of the nucleotide sequence of the hemoglobin receptor protein as depicted in FIGS. 2A–2H (SEQ ID No.:1), FIGS. 7A–7I (SEQ ID No.:3), FIGS. 8A–8I (SEQ ID No.:5) and FIGS. 9A–9I (SEQ ID No.:7), or any portion thereof effective in nucleic acid hybridization. Mixtures of such nucleic acid hybridization probes are also within the scope of this embodiment of the invention. Nucleic acid probes as provided herein are useful for detecting the presence of a bacteria, inter alia, in a human as the result of an infection, in contaminated biological samples and specimens, in foodstuffs and water supplies, or in any substance that may come in to contact with the human. Specific hybridization will be understood to mean that the nucleic acid probes of the invention are capable of forming stable, specific hybridization to bacterially-derived DNA or RNA under conditions of high stringency, as the term "high stringency" would be understood by those with skill in the art (see, for example, Sambrook et al., 1989, Molecular Cloning: A Laboratory Manual, Cold Spring Harbor Laboratory Press, Cold Spring Harbor, N.Y. and Hames and Higgins, eds., 1985, Nucleic Acid Hybridization, IRL Press, Oxford, U.K.). Hybridization will be understood to be accomplished using well-established techniques, including but not limited to Southern blot hybridization, Northern blot hybridization, in situ hybridization and Southern hybridization to polymerase chain reaction product DNAs. The invention will thus be understood to provide oligonucleotides, specifically, pairs of oligonucleotides, for use as primers in support of in vitro amplification of bacterial hemoglobin receptor genes and mRNA transcripts.

The production of proteins such as bacterial hemoglobin receptor proteins from cloned genes by genetic engineering means is well known in this art. The discussion which follows is accordingly intended as an overview of this field, and is not intended to reflect the full state of the art. It will be understood from the following discussion that the hemoglobin receptor protein genes of this invention are particularly advantageous, since expression of such proteins by bacteria, including non-Neisseria species of bacteria, can complement certain auxotrophic mutants of said transformed bacteria otherwise unable to subsist absent supplementation of the growth media with iron (E).

DNA encoding a bacterial hemoglobin receptor protein, in view of the instant disclosure, by chemical synthesis, by screening reverse transcripts of mRNA from appropriate cells, by screening genomic libraries from appropriate cells, or by combinations of these procedures, as illustrated below. Screening of mRNA or genomic DNA may be carried out with oligonucleotide probes generated from the nucleic acid sequence information from the bacterial hemoglobin receptor protein disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, bacterial hemoglobin receptor protein-encoding nucleic acids may be obtained by use of the polymerase chain reaction (PCR) procedure, using appropriate pairs of PCR oligonucleotide primers corresponding to nucleic acid sequence information derived from a bacterial hemoglobin receptor protein as provided herein. See U.S. Pat. No. 4,683,195 to Mullis et al. and U.S. Pat. No. 4,683,202 to Mullis, as specifically disclosed herein in Example 9 below. In another alternative, such bacterial hemoglobin receptor protein-encoding nucleic acids may be isolated from auxotrophic cells transformed with a bacterial hemoglobin receptor protein gene, thereby relieved of the nutritional requirement for uncomplexed iron (III).

Any bacterial hemoglobin receptor protein of the invention may be synthesized in host cells transformed with a recombinant expression construct comprising a nucleic acid encoding the bacterial hemoglobin receptor protein. Such recombinant expression constructs can also be comprised of a vector that is a replicable DNA construct. Vectors are used herein either to amplify DNA encoding a bacterial hemoglobin receptor protein and/or to express DNA encoding a bacterial hemoglobin receptor protein. For the purposes of this invention, a recombinant expression construct is a replicable DNA construct in which a nucleic acid encoding a bacterial hemoglobin receptor protein is operably linked to suitable control sequences capable of effecting the expression of the bacterial hemoglobin receptor protein in a suitable host cell.

The need for such control sequences will vary depending upon the host cell selected and the transformation method chosen. Generally, bacterial control sequences include a transcriptional promoter, an optional operator sequence to control transcription, a sequence encoding suitable mRNA ribosomal binding sites (the Shine-Delgarno sequence), and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1989, ibid.

Vectors useful for practicing the present invention include plasmids and virus-derived constructs, including phage and particularly bacteriophage, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pLAFR2 (see Riboli et al., 1991, *Microb. Pathogen.* 10: 393–403).

Transformed host cells are cells which have been transformed or transfected with recombinant expression constructs made using recombinant DNA techniques and comprising nucleic acid encoding a bacterial hemoglobin receptor protein. Preferred host cells are cells of Neisseria species, particularly *N. meningitidis*, as well as *Salmonella typhi* and *Salmonella typhimurium* species, and *Escherichia coli* auxotrophic mutant cells (hemA aroB). Transformed host cells may express the bacterial hemoglobin receptor protein, but host cells transformed for purposes of cloning or amplifying nucleic acid hybridization probe DNA need not express the receptor protein. When expressed, the bacterial hemoglobin receptor protein of the invention will typically be located in the host cell outer membrane. See, Sambrook et al., ibid.

Cultures of bacterial cells, particularly cells of Neisseria species, and certain *E. coli* mutants, are a desirable host for recombinant bacterial hemoglobin receptor protein synthesis. In principal, any bacterial cell auxotrophic for uncomplexed iron (III) is useful for selectively growing bacterial hemoglobin receptor protein-transformed cells. However, for this purpose, well-characterized auxotrophs, such as *E. coli* hemA aroB mutants are preferred.

The invention provides homogeneous compositions of a bacterial hemoglobin receptor protein produced by transformed cells as provided herein. Each such homogeneous composition is intended to be comprised of a bacterial hemoglobin receptor protein that comprises at least 90% of the protein in such a homogenous composition. The invention also provides membrane preparations from cells expressing a bacterial hemoglobin receptor protein as the result of transformation with a recombinant expression construct of the invention, as described herein.

Bacterial hemoglobin receptor proteins, peptide fragments thereof and membranes derived from cells expressing such proteins in accordance with the present invention may be used for the production of vaccines effective against bacterial infections in a human, with pathogenic microorganisms expressing such bacterial hemoglobin receptor proteins. Such vaccines preferably would be effective in raising an immunological response against bacteria of Neisseria species, most preferably *N. meningitidis* and *N. gonorhoeae*. Also encompassed within the vaccines provided by the invention are recombinant expression constructs as disclosed herein useful per se as vaccines, for introduction into an animal and production of an immunologic response to bacterial hemoglobin receptor protein antigens encoded therein.

Preparation of vaccines which contain polypeptide or polynucleotide sequences as active ingredients is well understood in the art. Typically, such vaccines are prepared as injectables, either as liquid solutions or suspensions. However, solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1 to 2%. Oral formulations include such normally employed excipients as, for example, pharmaceutical grades of manitol, lactose, starch, magnesium stearate, sodium saccharine, cellulose, magnesium carbonate and the like. These compositions take the form of solutions, suspensions, tablets, pills, capsules, sustained release formulations or powders and contain 10% to 95 % of active ingredient, preferably 25 to70%.

The polypeptides of the invention may be formulated into the vaccine as neutral or salt forms. Pharmaceutically acceptable salts, include the acid additional salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, such vaccines are provided wherein the bacterial hemoglobin receptor proteins or peptide fragments thereof are present in the intact cell membranes of cells expressing such proteins in accordance with the present invention. In preferred embodiments, cells useful in these embodiments include attenuated varieties of cells adapted to growth in humans. Most preferably, said cells are attenuated varieties of cells adapted for growth in humans, i.e., wherein such cells do not cause frank disease or other pathological conditions, such as bactermia, endotoxemia or sepsis. For the purposes of this invention, "attenuated" cells will be understood to encompass prokaryotic and eukaryotic cells that do not cause infection, disease, septicemia, endotoxic shock, pyrogenic shock, or other serious and adverse reactions to administration of vaccines to an animal, most preferably a human, when such cells are introduced into the animal, whether such cells are viable, living, heat-, chemically- or genetically attenuated or inactivated, or dead. It will be appreciated by those with skill in this art that certain minor side-effects of vaccination, such as short-term fever, muscle discomfort, general malaise, and other well-known reactions to vaccination using a variety of different types of vaccines, can be anticipated as accompanying vaccination of an animal, preferably a human, using the vaccines of the invention. Such acute, short-term and non-life-threatening side effects are encompassed in the instant definition of the vaccines of the invention, and vaccines causing such side-effects fall within the definition of "attenuated" presented herein. Preferred examples of such attenuated cells include attenutated varieties of Salmonella species, preferably *Salmonella typhi* and *Salmonella typhimurium*, as well as other attenuated bacterial species. It will be specifically understood that these embodiments of the vaccines of the invention encompass so-called "live" attenuated cell preparations as well as heat- or chemically-inactivated cell preparations.

In other embodiments of the invention are provided vaccines that are DNA vaccines, comprising the nucleic acids of the invention in recombinant expression constructs competant to direct expression of hemoglobin receptor proteins when introduced into an animal. In preferred embodiments, such DNA vaccines comprise recombinant expression constructs wherein the hemoglobin receptor-encoding nucleic acids of the invention are operably linked to promoter elements, most preferably the early gene promoter of cytomegalovirus or the early gene promoter of simian virus 40. DNA vaccines of the invention are preferably administered by intramuscular injection, but any appropriate route of administration, including oral, transdermal, rectal, nasal, aerosol administration into lung, or any other clinically-acceptable route of administration can be used by those with skill in the art.

In general, the vaccines of the invention are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of several hundred micrograms active ingredient per individual. Suitable regimes for initial administration and booster shots are also variable, but are typified by an initial administration followed in one or two week intervals by a subsequent injection or other administration.

The recombinant expression constructs of the present invention are also useful in molecular biology to transform bacterial cells which do not ordinarily express a hemoglobin receptor protein to thereafter express this receptor. Such cells are useful, inter alia, as intermediates for making cell membrane preparations useful for receptor binding activity assays, vaccine production, and the like, and in certain embodiments may themselves be used, inter alia, as vaccines or components of vaccines, as described above. The recombinant expression constructs of the present invention thus provide a method for screening potentially useful bactericidal and bacteriostatic drugs at advantageously lower cost than conventional screening protocols. While not completely eliminating the need for ultimate in vivo activity and toxicology assays, the constructs and cultures of the invention provide an important first screening step for the vast number of potentially useful bactericidal and bacteriostatic drugs synthesized, discovered or extracted from natural sources each year. In addition, such bactericidal or bacteriostatic drugs would be selected to utilize a nutritional pathway associated with infectious virulence in these types of bacteria, as disclosed in more detail below, thus selectively targeting bacteria associated with the development of serious infections in vivo.

Also, the invention provides both functional bacterial hemoglobin receptor proteins, membranes comprising such proteins, cells expressing such proteins, and the amino acid sequences of such proteins. This invention thereby provides sufficient structural and functional activity information to enable rational drug design of novel therapeutically-active antibacterial drugs using currently-available techniques (see Walters, "Computer-Assisted Modeling of Drugs", in Klegerman & Groves, eds., 1993, *Pharmaceutical Biotechnology*, Interpharm Press: Buffalo Grove, Ill., pp. 165–174).

Nucleic acids and oligonucleotides of the present invention are useful as diagnostic tools for detecting the existence of a bacterial infection in a human, caused by a hemoglobin receptor protein-expressing pathological organism of Neisseria species. Such diagnostic reagents comprise nucleic acid hybridization probes of the invention and encompass paired oligonucleotide PCR primers, as described above. Methods provided by the invention include blot hybridization, in situ hybridization and in vitro amplification techniques for detecting the presence of pathogenic bacteria in a biological sample. Appropriate biological samples advantageously screened using the methods described herein include plasma, serum, lymph, cerebrospinal fluid, seminal fluid, mucosal tissue samples, biopsy samples, and other potential sites of bacterial infection. It is also envisioned that the methods of the invention may be used to screen water, foodstuffs, pharmaceuticals, and other potential sources of infection.

The invention also provides antibodies that are immunologically reactive to a bacterial hemoglobin receptor protein or epitopes thereof provided by the invention. The antibodies provided by the invention may be raised, using methods well known in the art, in animals by inoculation with cells that express a bacterial hemoglobin receptor protein or epitopes thereof, cell membranes from such cells, whether crude membrane preparations or membranes purified using methods well known in the art, or purified preparations of proteins, including fusion proteins, particularly fusion proteins comprising epitopes of a bacterial hemoglobin receptor protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell that naturally expresses a bacterial hemoglobin receptor protein as provided by the invention, or any cell or cell line that expresses a bacterial hemoglobin receptor protein of the invention, or any epitope thereof, as a result of molecular or genetic engineering, or that has been treated to increase the expression of an endogenous or heterologous bacterial hemoglobin receptor protein by physical, biochemical or genetic means. Preferred cells are *E. coli* auxotrophic mutant hemA aroB cells transformed with a recombinant expression construct of the invention and grown in media supplemented with hemin or hemoglobin as the sole iron (III) source, and cells of Neisseria species.

The present invention also provides monoclonal antibodies that are immunologically reactive with an epitope of a bacterial hemoglobin receptor protein of the invention, or fragment thereof, present on the surface of such cells, preferably *E. coli* cells. Such antibodies are made using methods and techniques well known to those of skill in the art. Monoclonal antibodies provided by the present invention are produced by hybridoma cell lines, that are also provided by the invention and that are made by methods well known in the art (see Harlow and Lane, 1988, *Antibodies: A Laboratory Manual*, Cold Spring Harbor Laboratory Press, Cold Spring Harbor, N.Y.).

Hybridoma cell lines are made by fusing individual cells of a myeloma cell line with spleen cells derived from animals immunized with a homogeneous preparation of a bacterial hemoglobin receptor protein, membranes comprised thereof, cells expressing such protein, or epitopes of a bacterial hemoglobin receptor protein, used per se or comprising a heterologous or fusion protein construct, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a bacterial hemoglobin receptor protein of the invention. The present invention also encompasses fragments, including but not limited to F(ab) and F(ab)'$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of a bacterial hemoglobin receptor protein, made by methods known to those of skill in the art.

The antibodies and fragments used herein can be labeled preferably with radioactive labels, by a variety of techniques. For example, the biologically active molecules can also be labeled with a radionucleotide via conjugation with the cyclic anhydride of diethylenetriamine penta-acetic acid (DPTA) or bromoacetyl aminobenzyl ethylamine diamine tetra-acidic acid (BABE). See Hnatowich et al. (1983, *Science* 220: 613–615) and Meares et al. (1984, *Anal. Biochem.* 142: 68–78, both references incorporated by reference) for further description of labeling techniques.

The present invention also encompasses an epitope of a bacterial hemoglobin receptor protein of the invention, comprised of sequences and/or a conformation of sequences present in the receptor molecule. This epitope may be naturally occurring, or may be the result of proteolytic cleavage of a receptor molecule and isolation of an epitope-containing peptide or may be obtained by synthesis of an epitope-containing peptide using methods well known to those of skill in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to a bacterial hemoglobin receptor protein-derived epitope. The chimeric antibodies embodied in the present invention include those that are derived from naturally occurring antibodies as well as chimeric antibodies made by means of genetic engineering technology well known to those of skill in the art.

Also provided by the present invention are diagnostic and therapeutic methods of detecting and treating an infection in a human, by a pathogenic organisms expressing a bacterial hemoglobin receptor protein. Diagnostic reagents for use in such methods include the antibodies, most preferably monoclonal antibodies, of the invention. Such antibodies are used in conventional immunological techniques, including but not limited to enzyme-linked immunosorbent assay (ELISA), radioimmune assay (RIA), Western blot assay, immunological titration assays, immunological diffusion assays (such as the Ouchterlony assay), and others known to those of skill in the art. Also provided are epitopes derived from a bacterial hemoglobin receptor protein of the invention and immunologically cross-reactive to said antibodies, for use in any of the immunological techniques described herein.

Additional diagnostic assays include nucleic acid hybridization assays, using the nucleic acids of the invention or specifically-hybridizing fragments thereof, for sensitive detection of bacterial genomic DNA and/or mRNA. Such assays include various blot assays, such as Southern blots, Northern blots, dot blots, slot blots and the like, as well as in vitro amplification assays, such as the polymerase chain reaction assay (PCR), reverse transcriptase-polymerase chain reaction assay (RT-PCR), ligase chain reaction assay (LCR), and others known to those skilled in the art. Specific restriction endonuclease digestion of diagnostic fragments detected using any of the methods of the invention, analogous to restriction fragment linked polymorphism assays (RFLP) are also within the scope of this invention.

The invention also provides therapeutic methods and reagents for use in treating infections in a human, cause by a microorganism expressing a bacterial hemoglobin receptor protein of the invention, most preferably a bacteria of Neisseria species. Therapeutic reagents for use in such methods include the antibodies, most preferably monoclonal antibodies, of the invention, either per se or conjugated to bactericidal or bacteriostatic drugs or other antibiotic compounds effective against the infectious microorganism. In such embodiments, the antibodies of the invention comprise pharmaceutical compositions, additionally comprising appropriate pharmaceutically-acceptable carriers and adjuvants or other ancillary components where necessary. Suitable carriers are, for example, water, saline, dextrose, glycerol, ethanol, or the like and combinations thereof. In addition, if desired, the pharmaceutical formulation may contain minor amounts of auxiliary substances such as wetting or emulsifying agents, pH buffering agents, or other compounds which enhance the effectiveness of the antibody. In these embodiments, it will be understood that the therapeutic agents of the invention serve to target the infectious bacteria, either by immunologically "tagging" the bacteria with an antibody of the invention for recognition by cytotoxic cells of a human's immune system, or by specifically delivering an antimicrobial drug to the infectious microorganism via the bacterial hemoglobin receptor protein.

Additional therapeutic reagents include the nucleic acids of the invention or fragments thereof, specifically antisense embodiments of such nucleic acids. Such antisense nucleic acids may be used themselves or embodied in a recombinant expression construct specific for antisense expression, wherein said construct is genetically engineered to co-opt a portion of the genome of a bacterial virus, preferably a bacteriophage, infectious for the bacterial pathogen responsible for the infection. In these embodiments, introduction of the antisense nucleic acids of the invention into the bacterial cell inhibits, attenuates or abolishes expression of the bacterial hemoglobin receptor, thereby reducing the virulence of the bacterial infection and enabling more effective antibacterial interventions. In additional embodiments, bacteriophage are provided bearing "knockout" copies of a bacterial hemoglobin receptor gene, whereby the phage achieves genetic mutation of the endogenous hemoglobin receptor gene in the infectious bacteria via, for example, homologous recombination of the exogenous knockout copy of the bacterial hemoglobin receptor gene with the endogenous hemoglobin receptor gene in the infectious microorganism.

The Examples which follow are illustrative of specific embodiments of the invention, and various uses thereof. They set forth for explanatory purposes only, and are not to be taken as limiting the invention.

EXAMPLE 1

Plasmids, Bacteria, and Media

Plasmids and bacteria used herein are listed on Table 1. *E. coli* strains were routinely grown in Luria-Bertani (LB) broth supplemented with 5-aminolevulinic acid and 50 mg/L hemin chloride as necessary. *N. meningitidis* 8013 is a serogroup C clinical isolate (Nassif et al., 1993, *Mol. Microbiol.* 8: 719–725). The meningococci were routinely grown on GCB agar (Difco) supplemented as described by Kellogg et al. (1963, *J. Bacteriol* 85: 1274–1279), and incubated at 37° C. under a 5% $CO_2$ atmosphere. Transformation of meningococci was performed as described by Nassif et al. (1992, *Mol. Microbiol.* 6: 591–597). When necessary, the following antibiotics were used with *E. coli*: rifampicin, 100 mg/L; tetracycline, 15 mg/L; kanamycin, 30 mg/L; chloramphenicol, 20 mg/L; carbenicillin, 100 mg/L. For Neisseriae, kanamycin at 100 mg/L was used when needed.

EXAMPLE 2

Auxotroph Complementation Cloning of a Hemoglobin Receptor Gene from *Neisseria meningitidis*

In order to identify *N. meningitidis* outer membrane receptor(s) involved in the uptake of hemin and/or hemoglobin iron, an auxotroph complementation cloning strategy was used, similar to the approach previously taken to identify the *Y. enterocolitica* and *V. cholerae* hemin receptors (see Stojiljkovic and Hantke, 1992*, EMBO J*. 11: 43594367; Henderson and Payne, 1994*, J. Bacteriol*. 176: 3269–3277). This strategy is based on the fact that the outer membrane of Gram-negative bacteria is impermeable to hemin (McConville and Charles, 1979*, J. Microbiol*. 113:165–168) and therefore *E. coli* porphyrin biosynthesis mutants cannot grow on exogenously supplied hemin. If provided with the *N. meningitidis* outer membrane hemin receptor gene, the *E. coli* porphyrin mutant would be able to use exogenously supplied hemin as its porphyrin source.

A cosmid bank of *N. meningitidis* 8013 clone 6 DNA was prepared using conventional cosmid cloning methodologies (Sambrook et al., 1989, ibid.). *N. meningitidis* bacterial DNA was partially digested by MboI, size fractionated on sucrose gradients and cloned into the BamHI site of the cosmid vector pLAFR2 (Riboli et al., 1991*, Microb. Pathogen*. 10: 393403). This cosmid bank was mobilized into the *E. coli* hemA aroB $Rif^r$ recipient strain by triparental matings using a conjugal plasmid pRK2013::Tn9. The mating mixture was plated on selective plates containing hemin chloride (50 mg/L), 0.1 mM 2,2'-dypyridil and rifampicin (100 mg/L). Several clones growing on exogenously supplied haemin were isolated after an overnight incubation.

TABLE I

| STRAIN | GENOTYPE |
|---|---|
| *E. coli* K12 | |
| EB53 | hemA, aroB, rpoB |
| KP1041 | MC4100tonB::$Km^r$ |
| H1388 | exbB::Tn10 Δlac pro |
| TSM348 | endA, hsdR, pro, supF, pRK2013::Tn9 |
| IR754 | EB53, tonB::$Km^r$ |
| IR736 | EB53, exbB::Tn10 |
| DH5α | recA, gyrB |
| *N. meningitidis* | |
| ATCC 13077 | Serotype A |
| — | Serotype B* |
| MC8013 | clone 6, wild type |
| MChmbR | hmbR::aphA-3 |
| *N. gonorrhoeae* MS11A | |
| PLASMIDS | |
| pSUSK | pA15 replicon, $chloramphenicol^r$ |
| pHEM22 | pLAFR2, hemoglobin-utilizing cosmid |
| pHEM44 | pLAFR2, hemin-utilizing cosmid |
| pIRS508 | 6kb ClaI, pSUSK |
| pIRS523 | 3kb BamHI/SalI, pUC19 |
| pIRS525 | 1.2kb aphA-3, in NotI site of pIRS523 |
| pIRS527 | 4kb BamHI/ClaI, pBluescript |
| pIRS528 | 0.7kb NotI/BamHI, pBluescript |
| pIRS692 | 3.3kb BamHI/HindIII, SU(SK) |

*Laboratory collection

The hemin utilization phenotype of these transformants was tested by re-introduction of the cosmids into naive *E. coli* hemA aroB cells and by monitoring the growth on hemin-supplemented plates. The ability of *E. coli* strains to utilize heme or hemoglobin as the sole iron source was tested as previously described (Stojiljkovic and Hantke, 1992, ibid.). Cells were grown on LB agar supplemented with 50 μM deferoxamine mesylate (an iron chelating agent, obtained from Sigma Chemical Co., St. Louis, Mo.). Filter discs (¼ inches, Schleichner & Schuell, Inc., Keene, N.H.) impregnated with the test compounds (20 μL of 5 mg/ml stock solutions unless otherwise stated) were placed on these plates. After overnight growth at 37° C. with 5 % $CO_2$, zones of growth around the discs were monitored. The iron-bound proteins tested in this assay (all obtained from Sigma Chemical Co.) were hemoglobin from human, baboon, bovine and mouse sources, bovine hemin, human lactoferrin (90% iron saturated), and human transferrin (90 % iron saturated, obtained from Boehringer Mannheim Biochemicals, Indianapolis, Ind.). A total of six hemin utilization positive cosmids were obtained using this protocol. Results using such assays are shown in Table II.

EXAMPLE 3

Restriction Enzyme Digestion Mapping of Hemin Utilization Positive Cosmids

Cosmid DNA from six hemin-utilization positive cosmids obtained as described in Example 2 were digested with ClaI, and the resulting fragments were cloned into ClaI-digested pSU(SK) vector (obtained from Stratagene, LaJolla, Calif.). One subclone, containing a 6 kb ClaI fragment from cosmid cos22 (the resultant plasmid was designated pIRS508), was determined to allow utilization of hemin and hemoglobin by E. coli hemA aroB assayed as described in Example 2. Another such clone, containing an 11 kb ClaI fragment from cos44 was also determined to allow hemin utilization in these auxotrophic mutant cells. Restriction analysis and Southern hybridization indicated that the DNA fragments originating from cos22 and cos44 are unrelated.

The deduced restriction enzyme digestion map of cosmid clone pIRS508 is shown in FIG. 1. Plasmid pIRS508 enabled E. coli hemA aroB to use both hemin and bovine hemoglobin as iron sources although growth on hemoglobin was somewhat weaker than on hemin (Table II). Further subcloning localized the hemin/hemoglobin utilization locus to the BamHI/HindIII fragment of the insert. In addition to sequences encoding the hemoglobin receptor gene (designated hmbR), sequences for a Neisseria insertion element (IS1106) and a portion of a Neisseria small repetitive element (IR1) are also represented in the FIG.

EXAMPLE 4

Nucleotide Sequence Analysis of a Cosmid Clone Encoding a Neisseria Hemoglobin Receptor Gene The nucleotide sequence of the 3.3 kb BamHI-HindIII DNA fragment carrying the hmbR gene and its promoter region was determined using the dideoxy chain termination method using a Sequenase 2.0 kit (obtained from U.S. Biochemicals, Cleveland, Ohio) and analyzed using a Bio-Rad electrophoresis system, an AutoRead kit (obtained from Pharmacia, Uppsala, SE) and an ALF-370 automatic sequenator (Pharmacia, Uppsala, Sweden). Plasmid subclones for sequencing were produced by a nested deletion approach using Erase-a-Base kit (obtained from Promega Biotech, Madison, Wis.) using different restriction sites in the hmbR gene. The nucleotide and predicted amino acid sequences of the hmbR gene are shown in FIGS. 2A–2H An open reading frame (ORF) encoding the N. meningitidis, serotype C hemoglobin receptor protein begins at position 470 of the sequence and encodes a protein having an amino acid sequence of 792 amino acids, with a calculated molecular weight of 85.5 kDa. A Shine-Delgarno sequence (SD) is found at position 460. The HmbR receptor protein contains a signal peptidase I recognition sequence at residues 22 to 24 of the protein (underlined), consistent with the fact that it is an outer membrane protein.

A typical Fur binding nucleotide sequence (designated "Fur box") was found in the promoter region of the hmbR gene (FIGS. 2A–2H). Like hemin utilization in Yersiniae and Vibrio, hemin and hemoglobin utilization in Neisseria are known to be iron-inducible phenotypes (West and Sparling, 1985, Infect. Immun. 47: 388–394; Dyer et al., 1987, Infect. Immun. 55: 2171–2175). In Gram-negative bacteria, conditional expression of many iron utilization genes is regulated by the Fur

TABLE II

| STRAIN | φ-TYPE | HEMIN IRON | PORPHYRIN | Hb IRON |
|---|---|---|---|---|
| N. meningitidis | | | | |
| MC8013 | wild type | +++ | N.T. | +++ |
| MChmbR | Hb$^R$ mutant | +++ | N.T. | − |
| E. coli | | | | |
| EB53 | iron utilization$^-$ | − | − | − |
| EB53 (pIRS508) | tonB$^+$, exbB$^+$, hmbR$^+$ | +++ | +++ | + |

TABLE II-continued

| STRAIN | φ-TYPE | HEMIN IRON | PORPHYRIN | Hb IRON |
|---|---|---|---|---|
| IR754 (pIRS508) | tonB$^-$, exbB$^+$, hmbR$^+$ | − | − | − |
| IR736 (pIRS508) | tonB$^+$, exbB$^-$, hmbR$^+$ | − | − | − |

N.T.—not tested. Use of hemin/hemoglobin as a porphyrin source was tested by scoring for growth of strains around hemin (5 mg/mL) or hemoglobin (for E. coli, 10 mg/mL; for N. meningitidis, 5 mg/mL) discs on LB plates. The use of the hemin/hemoglobin as an iron source was tested similarly except NBD plates supplemented with 50 µL of 5 g/L delta-aminolevulinic acid were used (GCB plates supplemented with the 50 µM Desferal in the case of N. meningitidis).
−: indicates no growth
+: less then 100 mm of growth zone around the disc
+++: ±15 mm of growth zone around the disc.

repressor, which recognizes a 19 bp imperfect dyad repeat (Fur-box) in the promoter regions of Fur-repressed genes. Recently, a genetic screen (FURTA) for the identification of Fur-regulated genes from different Gram-negative bacteria was described (Stojiljkovic et al., 1994, J. Mol. Biol. 236: 531–545), and this assay was used to test whether hmbR expression was controlled in this way. Briefly, a plasmid carrying a Fur-box sequence is transformed into an E. coli strain (H1717) which possesses a Fur-regulated lac fusion in the chromosome. Expression of this Fur-regulated lac fusion is normally repressed. Introduction of a multicopy Fur-box sequence on the plasmid titrates the available Fur repressor thus allowing expression of the Fur-regulated lac fusion (this phenotype is termed FURTA positive). Using this screen, the smallest insert fragment from cosmid pIRS508 that produced a FURTA positive result was a 0.7 kb BamHI-NotI DNA fragment carried on plasmid pIRS528 (see FIG. 1). This result indicated that the 0.7 kb BamHI-NotI fragment carries a Fur-box and that gene expression from the hmbR promoter is controlled by a fur-type operon.

Figure 3:
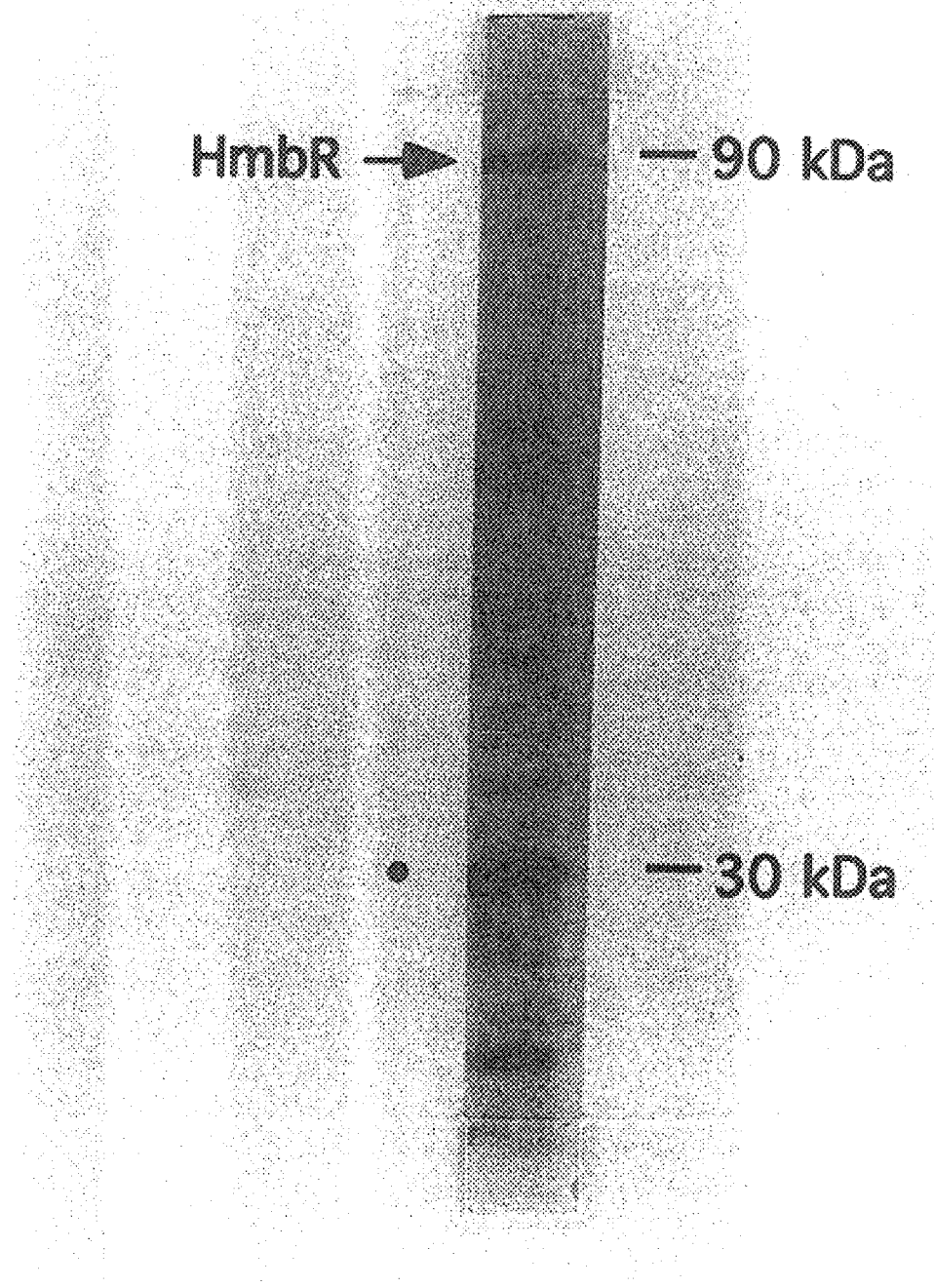
FIG. 3 presents a photograph of a stained SDS/ 10% PAGE electrophoresis gel showing the results of in vitro expression of the N. meningitides hemoglobin receptor gene product as an approximately 90 kilodalton protein, and β-lactamase protein having a molecular weight of about 30.0 kilodaltons used as a molecular weight marker.

N. meningitidis, serotype C hemoglobin receptor protein was expressed in vitro using an E. coli S30 extract system from Promega Biotech (Madison, Wis.). The 3.3 kb BamHI-HindIII fragment, expressed in vitro, encoded a 90kDa protein which corresponds in size to the predicted molecular weight of the unprocessed HmbR receptor. SDS/10% PAGE analysis showing the observed M$_r$ of 90K is shown in FIG. 3.

Immediately downstream of the hmbR gene (at positions 2955 to 3000 bp in FIGS. 2A–2H) was found a short nucleotide sequence that is 99 % identical to the flanking sequence of the PIII gene of N. gonorrhoeae (Gotschlich et al., 1987, J. Exp. Med. 165: 471482). The first 26 bp of this sequence represents one half of the inverted repeat (IR1) of the N. gonorrhoeae small repetitive element. This element is found in approximately 20 copies in both N. gonorrhoeae and N. meningitidis (Correia et al., 1988, J. Biol. Chem. 263: 12194–12198). The analysis of the nucleotide sequence from position 3027 to the ClaI (3984) restriction site (only the nucleotide sequence from BamHI (1) to HindIII (3370) is shown in FIGS. 2A–2H) indicated the presence of an IS1106 element (Knight et al., 1992, Mol. Microbiol. 6: 1565–1573). Interestingly, no nucleotide sequence similar to the IS1106 inverted repeat was found between the IRI element and the beginning of the homology to IS1106.

These results were consistent with the cloning and identification of a novel hemoglobin receptor protein gene from N. meningitidis, embodied in a 3.3 kb BamHI/HindIII fragment of N. meningitidis genomic DNA.

EXAMPLE 5

Amino Acid Sequence Comparison of the *N. meningitdis* Hemoglobin Receptor Protein and Neisseria Lactoferrin and Transferrin Receptor Proteins A comparison of the transferrin (Thp1; Legrain et al., 1993, *Gene* 130: 81–90), lactoferrin (LbpA; Pettersson et al., 1993, *Infect. Immun.* 61: 4724–4733, and 1994, *J. Bacteriol.* 176: 1764–1766) and hemoglobin receptors (HmbR) from *N. meningitidis* is shown in FIGS. 4A–4C. The comparison was done with the CLASTAL program from the PC/GENE program package (Intelligenetics, Palo Alto, Calif.). Only the amino-terminal and carboxyl terminal segments of the proteins are shown. An asterisk indicates identity and a point indicates similarity at the amino acid level. Lactoferrin and transferrin receptors were found to share 44.4% identity in amino acid sequence. In contrast, homology between these proteins and the hemoglobin receptor disclosed herein was found to be significantly weaker (22% amino acid sequence identity with lactoferrin and 21 % with transferrin receptor).

EXAMPLE 6

TonB/ExbBD-Dependence of Hemin Transport by the *N. meningitidis* Hemoglobin Receptor It was known that the transport of iron-containing siderophores, some colicins and vitamin B12 across the outer membrane of *E. coli* depends on three cytoplasmic membrane proteins: TonB, ExbB and ExbD (Postle 1990, *Mol. Microbiol.* 133: 891–898; Braun and Hantke, 1991, in Winkelmann, (ed.), *Handbook of Microbial Iron Chelates*, CRC Press, Boca Raton, Fla., pp. 107–138). In Yersinia and Hemophilus, hemin uptake was shown to be a TonB-dependent process (Stojiljkovic and Hantke, 1992, ibid.; Jarosik et al., 1994, *Infect. Immun.* 62: 2470–2477). Through direct interaction between the outer membrane receptors and the TonB cytoplasmic machinery, the substrate bound to the receptor is internalized into the periplasm (Heller et al., 1988, *Gene* 64: 147–153; Schoffler and Braun, 1989, *Molec. Gen. Genet.* 217: 378–383). This direct interaction has been associated with a particular amino acid sequence in membrane proteins associated with the TonB machinery.

All TonB-dependent receptors in Gram-negative bacteria contain several regions of high homology in their primary structures (Lundrigan and Kadner, 1986, *J. Biol. Chem.* 261: 10797–10801). In the amino acid sequence comparison described in Example 5, putative TonB-boxes of all three proteins are underlined. The carboxyl terminal end of the HmbR receptor contains the highly conserved terminal phenylalanine and position 782 arginine residues thought to be part of an outer membrane localization signal (Struyve et al., 1991, *J. Mol. Biol.* 218: 141–148; Koebnik, 1993, *Trends Microbiol.* 1: 201). At residue 6 of the mature HmbR protein, an amino acid sequence—ETTPVKA(SEQ ID NO.15)—is similar in sequence to the so called TonB-boxes of several Gram-negative receptors (Heller et al., 1988, ibid.). Interestingly, the putative TonB-box of HmbR has more homology to the TonB-box of the *N. gonorrhoeae* transferrin receptor (Cornelissen et al., 1992, *J. Bacteriol.* 174: 5788–5797) than to the TonB-boxes of *E. coli* siderophore receptors. When the sequence of the HmbR receptor was compared with other TonB-dependent receptors, the highest similarity was found with *Y. enterocolitica* HemR receptor although the similarity was not as high as to the Neisseria receptors.

In order to prove the TonB-dependent nature of the *N. meningitidis*, serotype C hemoglobin receptor, hmbR was introduced into exbB and tonB mutants of *E. coli* EB53, and the ability of the strains to utilize hemin and hemoglobin as porphyrin and iron sources was assessed. In these assays, both mutants of *E. coli* EB53 were unable to use hemin either as a porphyrin source or as an iron source in the presence of a functional hmbR (Table 2). The usage of hemoglobin as an iron source was also affected (Table 2). These results are consistent with the notion that the hmbR gene product, the *N. meningitidis* hemoglobin receptor protein of the invention, is TonB-dependent, since expression of this gene in TonB wild type *E. coli* supported the use of hemin and hemoglobin as sole iron source in the experiments disclosed in Example 2.

EXAMPLE 7

Functional Demonstration that the hmbR Gene Product is the Hemoglobin Receptor Protein in *N. meninitdis*

Figure 5:
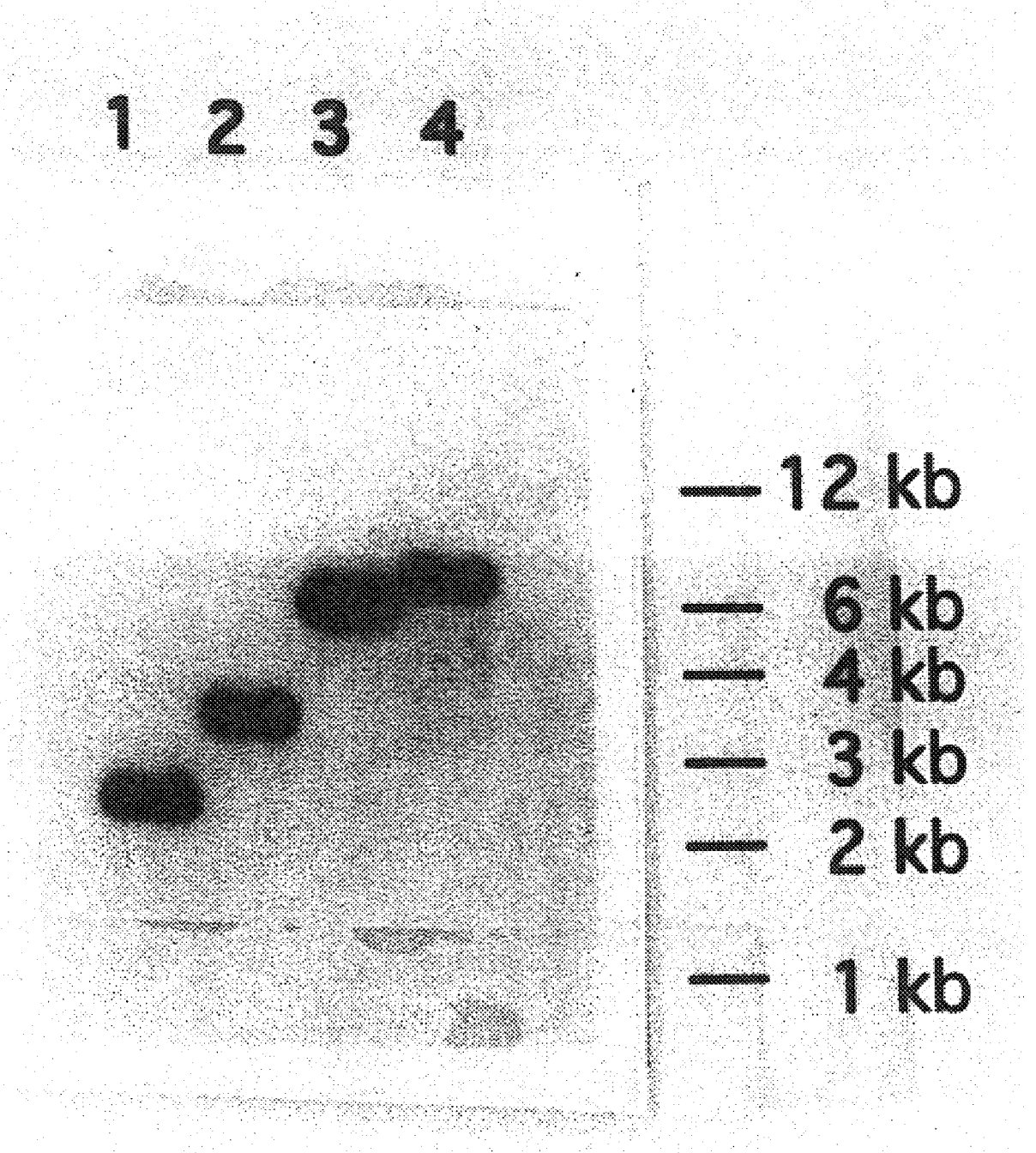

As shown in the data presented in Table II, hmbR mediated both hemin and hemoglobin utilization when expressed in *E. coli*, but hemoglobin utilization was less vigorous than hemin utilization. To determine if the HmbR receptor has the same specificity in *N. meningitidis*, hmbR was inactivated with a 1.2 kb kanamycin cassette (aphA-3; Nassif et al., 1991, ibid.) and transformed into wild-type *N. meningitidis* 8013 clone 6 (serotype C) cells. The inactivation of the chromosomal hmbR copy of the Km-resistant transformants was confirmed by Southern hybridization, as shown in FIG. 5. As can be seen from FIG. 5, wild-type *N. meningitidis* genomic DNA contains only one copy of the hmbR gene (lanes 1 and 3). In the $Km^r$ transformants, the size of the DNA fragments containing the wild-type gene has increased by 1.2 kb, which is the size of the Kan cassette (FIG. 5, lanes 2 and 4). When tested for its ability to utilize different iron-containing compounds, these mutant cells were found to be unable to use hemoglobin-bound iron, regardless of the source (human, bovine, baboon, mouse). The ability of the mutant to utilize hemoglobin-haptoglobin was not tested because the wild-type *N. meningitidis* strain is unable to use haptoglobin-haemoglobin complex as an iron source. However, the mutant was still able to use hemin iron, lactoferrin- and transferrin-bound iron as well as citrate-iron (Table II). As the iron-containing component of hemoglobin is hemin, a hemoglobin receptor would be expected to be capable of transporting hemin into the periplasm. Indeed, the cloning strategy disclosed herein depended on the ability of the cloned meningococcal receptor to transport hemin into the periplasm of *E. coli*. These results strongly suggest that *N. meningitidis* has at least two functional receptors that are involved in the internalization of hemin-containing compounds. One is the hemoglobin receptor described herein, which allows the utilization of both hemin and hemoglobin as iron sources. The other putative receptor in *N. meningitidis* is a hemin receptor which allows utilization of only hemin. This schema is also consistent with the isolation of several cosmid clones that allow *E. coli* EB53 to utilize hemin. DNAs from these cosmids do not hybridize with our hmbR probe, indicating that these clones encode a structurally-distinct receptor protein capable of transporting hemin into the periplasm of *N. meningitidis* cells.

EXAMPLE 8

Attenuation of Virulence in hmbR Mutant *N. meningitidis* Cells In Vivo

In order to test the importance of hemoglobin and hemin scavenging systems of *N. meningitidis* in vivo, the hmbR-mutant and the wild type strain of *N. meningitidis*, serotype C were inoculated into 5 day old infant rats and the numbers of bacteria recovered from blood and cerebrospinal fluid were followed. In these experiments, the method for the assessing *N. meningitidis*, serotype C virulence potential was essentially the same as described by Nassif et al. (1992, ibid.) using infant inbred Lewis rats (Charles River, Saint Aubin les Elbeufs, France). Inbred rats were used to minimize individual variations. Briefly, the 8013 strain was reactivated by 3 animal passages. After the third passage, bacteria were kept frozen in aliquots at −80° C. To avoid the possibility that modifications in the course of infection could result from selection of one spontaneous avirulent variant, one aliquot from the animal-passed frozen stock of 8013 was transformed with chromosomal DNA from the hmbR mutant, the resultant $Kan^r$ transformants were pooled without further purification and kept frozen at −80° C. For each experiment, all infant rats were from the same litter. *N. meningitidis* 8013 was grown overnight and $2\times10^6$ bacteria injected intraperitoneally into the infant rat. Three rats were used for each meningococcal strain. The course of infection was followed over a 24 hours time period with blood collected at the indicated times. At the 24 h time period, the rats were sacrificed, the cerebrospinal fluid (CSF) collected and the number of colony-forming units (CFU) determined. Each experiment was performed in replicate; similar results were obtained both times.

Figure 6:
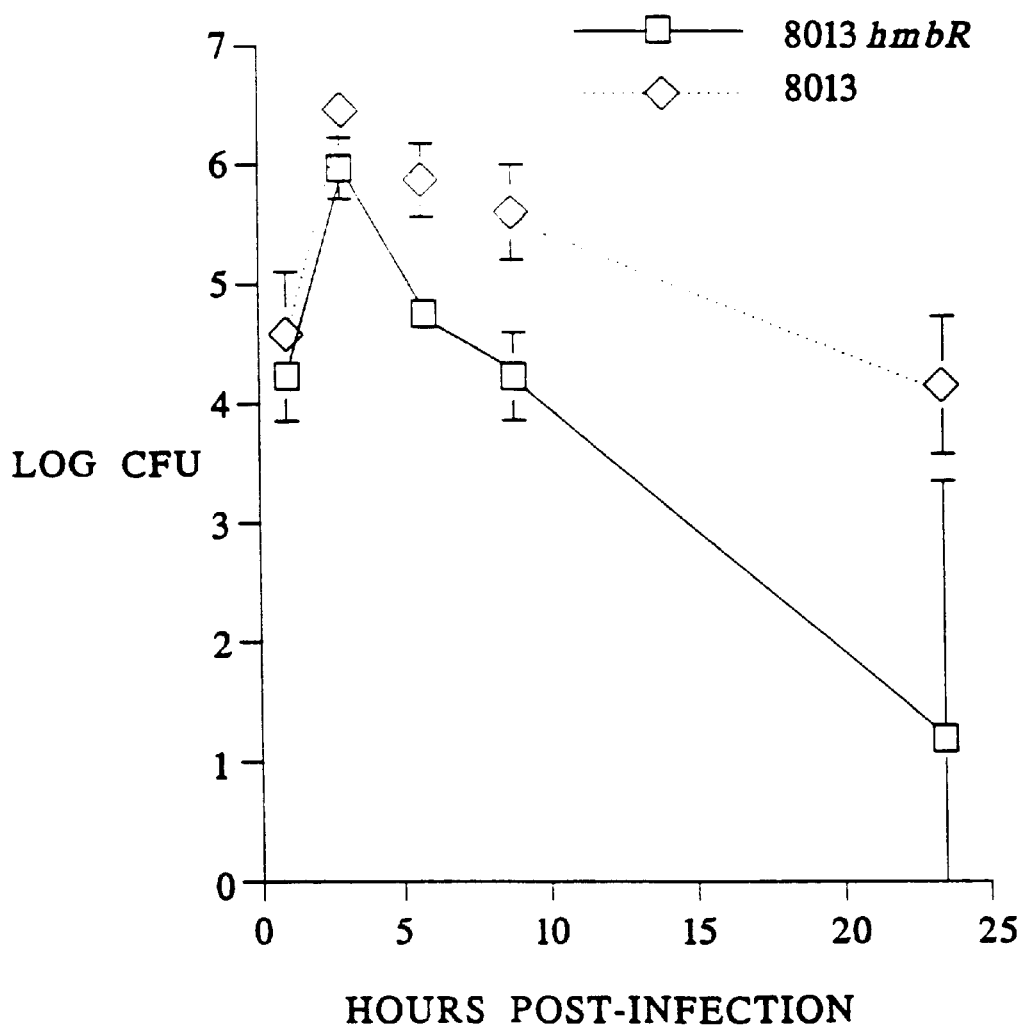
FIG. 6 is a graph describing the course of infection using N. meningitidis wild type (MC8013) and hmbR mutant strains in an in vivo rat infant infection model. Each strain was injected intraperitoneally ($2 \times 10^6$ CFU) into three infant inbred Lewis rats. The results represent the average of two similarly-performed experiments.
Figure 10:
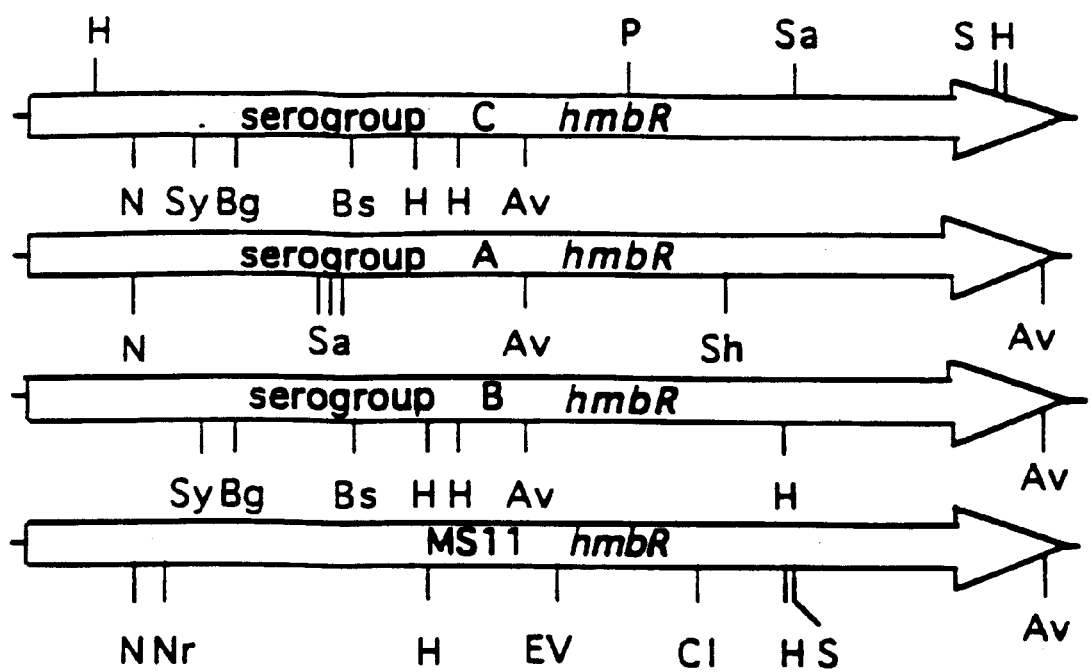
FIG. 10 represents a schematic of a nucleic acid sequence comparison between the hemoglobin receptor proteins derived from N. meningitidis, serotype B (SEQ ID No.:3), serotype A (SEQ ID No.:5) and serotype C (SEQ ID No.:1) and from N. gonorrhoeae (SEQ ID No.:7), wherein the direction of trascription of the genes is in the direction of the arrow, and the following abbreviations refer to restriction endonuclease sites: H represents HindIII; N represents NotI; Bg represents BglI; Bs represents BssHI; Nr represents NruI; Cl represents ClaI; P represents PstI; Sa represents SacI; Av represents AvaI; B represents BamHI; S represents SalI; EV represents EcoRV; Sh represents SphI; and Sy represents StyI.

The results of these experiments are shown in FIG. 6. The $hmbR^-$ strain, which is unable to use hemoglobin as an iron source, was recovered from the blood of infected animals in significantly lower numbers when compared with the wild type strain. Both the mutant and the wild type strain were still able to cross the blood-brain barrier as indicated by the isolation of bacteria from the cerebrospinal fluid. These results indicate that hemoglobin represents an important iron source for *N. meningitidis* during growth in vivo.

EXAMPLE 9

Polymerase Chain Reaction Amplification of Hemoglobin Receptor Genes from *N. menintztidis* Serotypes and *N. gonorrhoeae*

From the nucleotide sequence of the 3.3 kb BamHI-HindIII DNA fragment carrying the hmbR gene and its promoter region was determined specific oligonucleotide promers for in vitro amplification of the homologous hemoglobin receptor protein genes from *N. meningitidis* serotypes A and B and *N. gonorrhoeae* MS11A as follows.

The following oligonucleotide primers were developed for in vitro amplificaiton reactions using the polymerase chain reaction (PCR; Saiki et al., 1988, *Science* 230: 1350–1354):

5'-AAACAGGTCTCGGCATAG-3' (sense primer) (SEQ ID No.:11)

5'-CGCGAATTCAAACAGGTCTCGGCATAG-3' (antisense primer) (SEQ ID No.:12)

for amplifying the hemoglobin receptor protein from *N. meningitidis*, serotype A;

5'-CGCGAATTCAAAAACTTCCATTCCAGCGATACG-3' (sense primer) (SEQ ID No.:13)

5'-TAAAACTTCCATTCCAGCGATACG-3' (antisense primer) (SEQ ID No.:14)

for amplifying the hemoglobin receptor protein from *N. meningitidis*, serotype B;

5'-AAACAGGTCTCGGCATAG-3' (sense primer) (SEQ ID No.:15) or

5'-CGCGAATTCAAACAGGTCTCGGCATAG-3' (sense primer) (SEQ ID No.:16) and

5'-CGCGAATTCAAAAACTTCCATTCCAGCGATACG-3' (antisense primer) (SEQ ID No.:17) or

5'-TAAAACTTCCATTCCAGCGATACG-3' (antisense primer) (SEQ ID No.:18)

for amplifying the hemoglobin receptor protein from *N. gonorrhoeae* MS11A.

Genomic DNA from *N. meningitidis* serotype A or B or *N. gonorrhoeae* species was prepared using standard techniques (see Sambrook, et al., ibid.), including enzymatic degradation of bacterial cell walls, protoplast lysis, protease and RNase digestion, extraction with organic solvents such as phenol and/or chloroform, and ethanol precipitation. Crude DNA preparations were also used. An amount (typically, about 0.1 μg) of genomic DNA was used for each amplification reaction. A PCR amplification reaction consisted of Tic polymerase (Stratagene, LaJolla, Calif.) and/or Taq polymerase (Boehringer Mannheim, Germany) in the appropriate buffer including about 20picomoles of each amplificaiton primer and 200 nanomoles of each deoxynucleoside triphosphate. Amplification reactions were performed according to the following scheme:

| | |
|---|---|
| First cycle | 5 min at 95° C. |
| | 2 min at 51° C. |
| | 6 min at 72° C. |
| Cycles 2–13 | 45 sec at 95° C. |
| | 35 sec at 49° C. |
| | 10 min at 72° C. |
| Cycles 14–30 | 25 sec at 95° C. |
| | 35 sec at 47° C. |
| | 10 min at 72° C. |

Upon completion of the amplification reaction, DNA fragments were cloned either blunt-ended or, after EcoRI digestion, into EcoRI digested pSUKS or pWKS30 vectors and transformed into bacteria. Positively-selected clones were then analyzed for the presence of recombinant inserts, which were sequenced as described above in Example 4.

As a result of these experiments, three clones encoding the hemoglobin receptor genes from *N. meningitidis* serotypes A and B and *N. gonorrhoeae* MS11A were cloned and the sequence of these genes determined. The nucleic acid sequence for each of these genes are shown in FIGS. 7A–7I (*N. meningitidis*, serotype B), FIGS. 8A–8I (*N. meningitidis*, serotype B) and FIGS. 9A–9I (*N. gonorrhoeae* MS11A).

The degree of homology between the cloned hemoglobin receptors from the different *N. meningitidis* serotypes and *N. gonorrhoeae* MS11A was assessed by nucleic acid and amino acid sequence comparison, as described in Example 5 above. The results of these comparisons are shown in FIG. 10 and FIGS. 11A–11D, respectively. Hemoglobin receptor genes from the three *N. meningitidis* serotypes and *N. gonorrhoeae* MS11A were found to be from 86.5% to 93.4% homologous; the most homologous nucleic acids were *N. meningitidis* serotypes B and C, and the most divergent nucleic acids were *N. meningitidis* serotype B and *N. gonorrhoeae* MS11A (FIG. 10 and Table III). Homoglobin receptor proteins from all four Neisseria species showed a high degree of homology to the other members of the group, ranging from 87% homology between the hemoglobin receptor proteins from *N. gonorrhoeae* MS11A and *N. meningitidis* serotype B to 93% homology between hemoglobin receptor proteins from *N. meningitidis* serotypes A and B (FIGS. 11A–11D). In this comparison, all four receptors were found to share 84.7% amino acid sequence identity, and up to 11.6% sequence similarity (i.e., chemically-related amino acid residues at homologous sites within the amino acid sequence). The non-conserved amino acids were found clustered in the regions of the amino acid sequence corresponding to the external loops in the predicted topographical structure of the hemoglobin receptor proteins.

It should be understood that the foregoing disclosure emphasizes certain specific embodiments of the invention and that all modifications or alternatives equivalent thereto are within the spirit and scope of the invention as set forth in the appended claims.

TABLE III

| * | A | B | C | MS11 |
|---|---|---|---|------|
| A | X | 92.2% | 93.0% | 90.4% |
| B | 93.3% | X | 93.4% | 86.5% |
| C | 93.2% | 93% | X | 90.4% |
| MS11 | 91.1% | 86.8% | 91.4% | X |

*The numbers in the upper quadrant of the Table (in boldface) represent nucleic acid sequence homology between the different hemoglobin receptor genes of the invention, while the numbers in the lower quadrant of the Table represent amino acid sequence homology between the different hemoglobin receptor proteins

---

What we claim is:

1. A homogeneous preparation of an isolated hemoglobin receptor protein from a Neisseria species having a molecular weight of about 90 kilodaltons as determined by SDS-polyacrylamide gel electrophoresis.

2. The isolated hemoglobin receptor protein of claim 1, wherein the protein has an amino acid sequence that is the amino acid sequence depicted as SEQ ID NO:2.

3. The isolated hemoglobin receptor protein of claim 1, wherein the protein has an amino acid sequence that is the amino acid sequence depicted as SEQ ID NO:4.

4. The isolated hemoglobin receptor protein of claim 1, wherein the protein has an amino acid sequence that is the amino acid sequence depicted as SEQ ID NO:6.

5. The isolated hemoglobin receptor protein of claim 1, wherein the protein has an amino acid sequence that is the amino acid sequence depicted as SEQ ID NO:8.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 3318 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: CDS
      (B) LOCATION: 470..2845

(xi) SEQUENCE DESCRIPTION: SEQ ID NO: 1:

```
AGAACTAGTG GATCCAATTT GGGCGCGGCG TTTTTGTTCA AACACGCCCA AAAACTCGAT      60

TACAACGGCG AACACGGCGC GCGCCACCTC GCTCCGCATC CCGACGGGCC GCGGCAAACA     120

CTGGCGCGCC TTCGTCGAGC ATCTGAACGC TTTGAACCTG ACTCCCGAAG CCGAAGCGGA     180

AGCCATTCAA GGCGCGCGCG AAGCCTTTGC ATTCTACAAA GTCGTGTTGC GCGAAAACCTT    240

CGGCTTGGCA GCCGATGCCG AAGCCCCCGA AGGTATGATG CCGCACAGGC ACTAAAAAAT    300

AATCGAACCA AATAAACAAG GTCTCGGCAT AGCTGTTTGC AGGGACCTTT AATTACACGG    360

CGCGGCTTTG TTTACATGGA TTACTGTCTT ATTAAATATT AATGATTATC ATAAAATCTA    420

TTATTCGCTA ACCGATGGAT GAACAATCCA TACATCTTGA GTTGATAAT ATG AAA        475
                                                      Met Lys
                                                       1

CCA TTA CAA ATG CTC CCT ATC GCC GCG CTG GTC GGC AGT ATT TTC GGC      523
Pro Leu Gln Met Leu Pro Ile Ala Ala Leu Val Gly Ser Ile Phe Gly
         5                  10                  15

AAT CCG GTC TTT GCG GCA GAT GAA GCT GCA ACT GAA ACC ACA CCC GTT      571
Asn Pro Val Phe Ala Ala Asp Glu Ala Ala Thr Glu Thr Thr Pro Val
    20                  25                  30

AAG GCA GAG GTA AAA GCA GTG CGC GTT AAA GGC CAG CGC AAT GCG CCT      619
Lys Ala Glu Val Lys Ala Val Arg Val Lys Gly Gln Arg Asn Ala Pro
35                  40                  45                  50
```

-continued

| | |
|---|---|
| GCG GCT GTG GAA CGC GTC AAC CTT AAC CGT ATC AAA CAA GAA ATG ATA<br>Ala Ala Val Glu Arg Val Asn Leu Asn Arg Ile Lys Gln Glu Met Ile<br>                 55                             60                        65 | 667 |
| CGC GAC AAC AAA GAC TTG GTG CGC TAT TCC ACC GAT GTC GGC TTG AGC<br>Arg Asp Asn Lys Asp Leu Val Arg Tyr Ser Thr Asp Val Gly Leu Ser<br>                 70                             75                        80 | 715 |
| GAC AGC GGC CGC CAT CAA AAA GGC TTT GCT GTT CGC GGC GTG GAA GGC<br>Asp Ser Gly Arg His Gln Lys Gly Phe Ala Val Arg Gly Val Glu Gly<br>                 85                             90                        95 | 763 |
| AAC CGT GTC GGC GTG AGC ATA GAC GGC GTA AAC CTG CCT GAT TCC GAA<br>Asn Arg Val Gly Val Ser Ile Asp Gly Val Asn Leu Pro Asp Ser Glu<br>                100                          105                      110 | 811 |
| GAA AAC TCG CTG TAC GCC CGT TAT GGC AAC TTC AAC AGC TCG CGT CTG<br>Glu Asn Ser Leu Tyr Ala Arg Tyr Gly Asn Phe Asn Ser Ser Arg Leu<br>115                        120                        125                      130 | 859 |
| TCT ATC GAC CCC GAA CTC GTG CGC AAC ATC GAC ATC GTA AAA GGG GCG<br>Ser Ile Asp Pro Glu Leu Val Arg Asn Ile Asp Ile Val Lys Gly Ala<br>                                135                        140                      145 | 907 |
| GAC TCT TTC AAT ACC GGC AGC GGC GCC TTG GGC GGC GGT GTG AAT TAC<br>Asp Ser Phe Asn Thr Gly Ser Gly Ala Leu Gly Gly Gly Val Asn Tyr<br>                150                          155                      160 | 955 |
| CAA ACC CTG CAA GGA CGT GAC TTA CTG TTG CCT GAA CGG CAG TTC GGC<br>Gln Thr Leu Gln Gly Arg Asp Leu Leu Leu Pro Glu Arg Gln Phe Gly<br>                  165                        170                      175 | 1003 |
| GTG ATG ATG AAA AAC GGT TAC AGC ACG CGT AAC CGT GAA TGG ACA AAT<br>Val Met Met Lys Asn Gly Tyr Ser Thr Arg Asn Arg Glu Trp Thr Asn<br>180                        185                        190 | 1051 |
| ACC CTC GGT TTC GGC GTG AGC AAC GAC CGC GTG GAT GCC GCT TTG CTG<br>Thr Leu Gly Phe Gly Val Ser Asn Asp Arg Val Asp Ala Ala Leu Leu<br>195                        200                        205                      210 | 1099 |
| TAT TCG CAA CGG CGC GGC CAT GAA ACT GAA AGC GCG GGC AAG CGT GGT<br>Tyr Ser Gln Arg Arg Gly His Glu Thr Glu Ser Ala Gly Lys Arg Gly<br>                  215                        220                      225 | 1147 |
| TAT CCG GTA GAG GGT GCT GGT AGC GGA GCG AAT ATC CGT GGT TCT GCG<br>Tyr Pro Val Glu Gly Ala Gly Ser Gly Ala Asn Ile Arg Gly Ser Ala<br>                    230                        235                      240 | 1195 |
| CGC GGT ATT CCT GAT CCG TCC CAA CAC AAA TAC CAC AGC TTC TTG GGT<br>Arg Gly Ile Pro Asp Pro Ser Gln His Lys Tyr His Ser Phe Leu Gly<br>                245                          250                      255 | 1243 |
| AAG ATT GCT TAT CAA ATC AAC GAC AAC CAC CGC ATC GGC GCA TCG CTC<br>Lys Ile Ala Tyr Gln Ile Asn Asp Asn His Arg Ile Gly Ala Ser Leu<br>260                        265                        270 | 1291 |
| AAC GGT CAG CAG GGG CAT AAT TAC ACG GTT GAA GAG TCT TAC AAC CTG<br>Asn Gly Gln Gln Gly His Asn Tyr Thr Val Glu Glu Ser Tyr Asn Leu<br>275                        280                        285                      290 | 1339 |
| CTT GCT TCT TAT TGG CGT GAA GCT GAC GAT GTC AAC AGA CGG CGT AAC<br>Leu Ala Ser Tyr Trp Arg Glu Ala Asp Asp Val Asn Arg Arg Arg Asn<br>                  295                        300                      305 | 1387 |
| ACC AAC CTC TTT TAC GAA TGG ACG CCG GAA TCC GAC CGG TTG TCT ATG<br>Thr Asn Leu Phe Tyr Glu Trp Thr Pro Glu Ser Asp Arg Leu Ser Met<br>                  310                        315                      320 | 1435 |
| GTA AAA GCG GAT GTC GAT TAT CAA AAA ACC AAA GTA TCT GCG GTC AAC<br>Val Lys Ala Asp Val Asp Tyr Gln Lys Thr Lys Val Ser Ala Val Asn<br>325                        330                        335 | 1483 |
| TAC AAA GGT TCG TTC CCG ATA GAG GAT TCT TCC ACC TTG ACA CGT AAC<br>Tyr Lys Gly Ser Phe Pro Ile Glu Asp Ser Ser Thr Leu Thr Arg Asn<br>340                        345                        350 | 1531 |
| TAC AAT CAA AAG GAC TTG GAT GAA ATC TAC AAC CGC AGT ATG GAT ACC<br>Tyr Asn Gln Lys Asp Leu Asp Glu Ile Tyr Asn Arg Ser Met Asp Thr<br>355                        360                        365                      370 | 1579 |

```
CGC TTC AAA CGC ATT ACC CTG CGT TTG GAC AGC CAT CCG TTG CAA CTC    1627
Arg Phe Lys Arg Ile Thr Leu Arg Leu Asp Ser His Pro Leu Gln Leu
            375                 380                 385

GGG GGG GGG CGA CAC CGC CTG TCG TTT AAA ACT TTC GCC AGC CGC CGT    1675
Gly Gly Gly Arg His Arg Leu Ser Phe Lys Thr Phe Ala Ser Arg Arg
            390                 395                 400

GAT TTT GAA AAC CTA AAC CGC GAC GAT TAT TAC TTC AGC GGC CGT GTT    1723
Asp Phe Glu Asn Leu Asn Arg Asp Asp Tyr Tyr Phe Ser Gly Arg Val
            405                 410                 415

GTT CGA ACC ACC AGC AGT ATC CAG CAT CCG GTG AAA ACC ACC AAC TAC    1771
Val Arg Thr Thr Ser Ser Ile Gln His Pro Val Lys Thr Thr Asn Tyr
            420                 425                 430

GGT TTC TCA CTG TCT GAC CAA ATT CAA TGG AAC GAC GTG TTC AGT AGC    1819
Gly Phe Ser Leu Ser Asp Gln Ile Gln Trp Asn Asp Val Phe Ser Ser
435                 440                 445                 450

CGC GCA GGT ATC CGT TAC GAT CAT ACC AAA ATG ACG CCT CAG GAA TTG    1867
Arg Ala Gly Ile Arg Tyr Asp His Thr Lys Met Thr Pro Gln Glu Leu
            455                 460                 465

AAT GCC GAG TGT CAT GCT TGT GAC AAA ACA CCG CCT GCA GCC AAC ACT    1915
Asn Ala Glu Cys His Ala Cys Asp Lys Thr Pro Pro Ala Ala Asn Thr
            470                 475                 480

TAT AAA GGC TGG AGC GGT TTT GTC GGC TTG GCG GCG CAA CTG AAT CAG    1963
Tyr Lys Gly Trp Ser Gly Phe Val Gly Leu Ala Ala Gln Leu Asn Gln
            485                 490                 495

GCT TGG CGT GTC GGT TAC GAC ATT ACT TCC GGC TAC CGT GTC CCC AAT    2011
Ala Trp Arg Val Gly Tyr Asp Ile Thr Ser Gly Tyr Arg Val Pro Asn
500                 505                 510

GCG TCC GAA GTG TAT TTC ACT TAC AAC CAC GGT TCG GGT AAT TGG CTG    2059
Ala Ser Glu Val Tyr Phe Thr Tyr Asn His Gly Ser Gly Asn Trp Leu
515                 520                 525                 530

CCC AAT CCC AAC CTG AAA GCC GAG CGC ACG ACC ACC CAC ACC CTC TCT    2107
Pro Asn Pro Asn Leu Lys Ala Glu Arg Thr Thr Thr His Thr Leu Ser
            535                 540                 545

CTG CAA GGC CGC AGC GAA AAA GGT ACT TTG GAT GCC AAC CTG TAT CAA    2155
Leu Gln Gly Arg Ser Glu Lys Gly Thr Leu Asp Ala Asn Leu Tyr Gln
            550                 555                 560

AGC AAT TAC CGC AAT TTC CTG TCT GAA GAG CAG AAG CTG ACC ACC AGC    2203
Ser Asn Tyr Arg Asn Phe Leu Ser Glu Glu Gln Lys Leu Thr Thr Ser
            565                 570                 575

GGC GAT GTC AGC TGT ACT CAG ATG AAT TAC TAC TAC GGT ATG TGT AGC    2251
Gly Asp Val Ser Cys Thr Gln Met Asn Tyr Tyr Tyr Gly Met Cys Ser
            580                 585                 590

AAT CCT TAT TCC GAA AAA CTG GAA TGG CAG ATG CAA AAT ATC GAC AAG    2299
Asn Pro Tyr Ser Glu Lys Leu Glu Trp Gln Met Gln Asn Ile Asp Lys
595                 600                 605                 610

GCC AGA ATC CGC GGT CTC GAG CTG ACG GGC CGT CTG AAT GTG GAC AAA    2347
Ala Arg Ile Arg Gly Leu Glu Leu Thr Gly Arg Leu Asn Val Asp Lys
            615                 620                 625

GTA GCG TCT TTT GTT CCT GAG GGC TGG AAA CTG TTC GGC TCG CTG GGT    2395
Val Ala Ser Phe Val Pro Glu Gly Trp Lys Leu Phe Gly Ser Leu Gly
            630                 635                 640

TAT GCG AAA AGC AAA CTG TCG GGC GAC AAC AGC CTG CTG TCC ACC CAG    2443
Tyr Ala Lys Ser Lys Leu Ser Gly Asp Asn Ser Leu Leu Ser Thr Gln
            645                 650                 655

CCG TTG AAA GTG ATT GCC GGT ATC GAC TAT GAA AGT CCG AGC GAA AAA    2491
Pro Leu Lys Val Ile Ala Gly Ile Asp Tyr Glu Ser Pro Ser Glu Lys
            660                 665                 670
```

-continued

```
TGG GGC GTG TTC TCC CGC CTG ACC TAT CTG GGC GCG AAA AAG GTC AAA      2539
Trp Gly Val Phe Ser Arg Leu Thr Tyr Leu Gly Ala Lys Lys Val Lys
675                 680                 685                 690

GAC GCG CAA TAC ACC GTT TAT GAA AAC AAG GGC TGG GGT ACG CCT TTG      2587
Asp Ala Gln Tyr Thr Val Tyr Glu Asn Lys Gly Trp Gly Thr Pro Leu
                695                 700                 705

CAG AAA AAG GTA AAA GAT TAC CCG TGG CTG AAC AAG TCG GCT TAT GTG      2635
Gln Lys Lys Val Lys Asp Tyr Pro Trp Leu Asn Lys Ser Ala Tyr Val
            710                 715                 720

TTC GAT ATG TAC GGC TTC TAC AAA CCG GTG AAA AAC CTG ACT TTG CGT      2683
Phe Asp Met Tyr Gly Phe Tyr Lys Pro Val Lys Asn Leu Thr Leu Arg
        725                 730                 735

GCA GGC GTA TAT AAT GTG TTC AAC CGC AAA TAC ACC ACT TGG GAT TCC      2731
Ala Gly Val Tyr Asn Val Phe Asn Arg Lys Tyr Thr Thr Trp Asp Ser
    740                 745                 750

CTG CGC GGC CTG TAT AGC TAC AGC ACC ACC AAC TCG GTC GAC CGC GAT      2779
Leu Arg Gly Leu Tyr Ser Tyr Ser Thr Thr Asn Ser Val Asp Arg Asp
755                 760                 765                 770

GGC AAA GGC TTA GAC CGC TAC CGC GCC CCA AGC CGT AAT TAC GCC GTA      2827
Gly Lys Gly Leu Asp Arg Tyr Arg Ala Pro Ser Arg Asn Tyr Ala Val
                775                 780                 785

TCG CTG GAA TGG AAG TTT TAATCTGGTA TTATTGAATT AATCGCCTTG             2875
Ser Leu Glu Trp Lys Phe
            790

TTGAAAATTA AAGCCGTCCG AATTGTGTTC AAGAACTCAT TCGGACGGTT TTTACCGAAT    2935

CTGTGTGTGG GTTTATAGTG GATTAACAAA AATCAGGACA AGGCGACGAA GCCGCAGACA    2995

GTACAGATAG TACGGAACCG ATTCACTTGG TGAGACCTTT GCAAAATTCC TTTCCCTCCC    3055

GACAGCCGAA ACCCAAACAC AGGTTTTCGG CTGTTTTCGC CCCAAATACC TCCTAATTCT    3115

ACCCAAATAC CCCCTTAATC CTCCCCGATA CCCGATAATC AGGCATCCGG CGCCTTTAGG    3175

CGGCAGCGGG CGCACTTAAC CTGTTTGGCG GCTTCAAAAG GTTCAAACAC ATCGCCTTCA    3235

GGTGGCTTTG CGCACTCACT TTAATCAGTC CGAAATAGGC CGCCCGCGCA TAGCAGAACT    3295

TACGGTGCAG CGTACCGAAC TTT                                            3318
```

(2) INFORMATION FOR SEQ ID NO: 2:

(i) SEQUENCE CHARACTERISTICS:
        (A) LENGTH: 792 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Pro Leu Gln Met Leu Pro Ile Ala Ala Leu Val Gly Ser Ile
1               5                   10                  15

Phe Gly Asn Pro Val Phe Ala Ala Asp Glu Ala Ala Thr Glu Thr Thr
            20                  25                  30

Pro Val Lys Ala Glu Val Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95
```

-continued

```
Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Asp Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Pro Glu Arg Gln
            165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Lys
    210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr His Ser Phe
            245                 250                 255

Leu Gly Lys Ile Ala Tyr Gln Ile Asn Asp Asn His Arg Ile Gly Ala
            260                 265                 270

Ser Leu Asn Gly Gln Gln Gly His Asn Tyr Thr Val Glu Glu Ser Tyr
        275                 280                 285

Asn Leu Leu Ala Ser Tyr Trp Arg Glu Ala Asp Asp Val Asn Arg Arg
    290                 295                 300

Arg Asn Thr Asn Leu Phe Tyr Glu Trp Thr Pro Glu Ser Asp Arg Leu
305                 310                 315                 320

Ser Met Val Lys Ala Asp Val Asp Tyr Gln Lys Thr Lys Val Ser Ala
            325                 330                 335

Val Asn Tyr Lys Gly Ser Phe Pro Ile Glu Asp Ser Ser Thr Leu Thr
            340                 345                 350

Arg Asn Tyr Asn Gln Lys Asp Leu Asp Glu Ile Tyr Asn Arg Ser Met
        355                 360                 365

Asp Thr Arg Phe Lys Arg Ile Thr Leu Arg Leu Asp Ser His Pro Leu
    370                 375                 380

Gln Leu Gly Gly Gly Arg His Arg Leu Ser Phe Lys Thr Phe Ala Ser
385                 390                 395                 400

Arg Arg Asp Phe Glu Asn Leu Asn Arg Asp Asp Tyr Tyr Phe Ser Gly
            405                 410                 415

Arg Val Val Arg Thr Thr Ser Ser Ile Gln His Pro Val Lys Thr Thr
            420                 425                 430

Asn Tyr Gly Phe Ser Leu Ser Asp Gln Ile Gln Trp Asn Asp Val Phe
        435                 440                 445

Ser Ser Arg Ala Gly Ile Arg Tyr Asp His Thr Lys Met Thr Pro Gln
    450                 455                 460

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
            485                 490                 495

Asn Gln Ala Trp Arg Val Gly Tyr Asp Ile Thr Ser Gly Tyr Arg Val
            500                 505                 510
```

```
Pro Asn Ala Ser Glu Val Tyr Phe Thr Tyr Asn His Gly Ser Gly Asn
        515                 520                 525

Trp Leu Pro Asn Pro Asn Leu Lys Ala Glu Arg Thr Thr His Thr
530                 535                 540

Leu Ser Leu Gln Gly Arg Ser Glu Lys Gly Thr Leu Asp Ala Asn Leu
545                 550                 555                 560

Tyr Gln Ser Asn Tyr Arg Asn Phe Leu Ser Glu Glu Lys Leu Thr
                565                 570                 575

Thr Ser Gly Asp Val Ser Cys Thr Gln Met Asn Tyr Tyr Gly Met
                580                 585                 590

Cys Ser Asn Pro Tyr Ser Glu Lys Leu Glu Trp Gln Met Gln Asn Ile
        595                 600                 605

Asp Lys Ala Arg Ile Arg Gly Leu Glu Leu Thr Gly Arg Leu Asn Val
610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
                660                 665                 670

Glu Lys Trp Gly Val Phe Ser Arg Leu Thr Tyr Leu Gly Ala Lys Lys
                675                 680                 685

Val Lys Asp Ala Gln Tyr Thr Val Tyr Glu Asn Lys Gly Trp Gly Thr
690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Val Lys Asn Leu Thr
                725                 730                 735

Leu Arg Ala Gly Val Tyr Asn Val Phe Asn Arg Lys Tyr Thr Thr Trp
                740                 745                 750

Asp Ser Leu Arg Gly Leu Tyr Ser Tyr Ser Thr Thr Asn Ser Val Asp
        755                 760                 765

Arg Asp Gly Lys Gly Leu Asp Arg Tyr Arg Ala Pro Ser Arg Asn Tyr
770                 775                 780

Ala Val Ser Leu Glu Trp Lys Phe
785                 790

(2) INFORMATION FOR SEQ ID NO: 3:

(i) SEQUENCE CHARACTERISTICS:
        (A) LENGTH: 2376 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2373

(xi) SEQUENCE DESCRIPTION: SEQ ID NO: 3:

ATG AAA CCA TTA CAA ATG CCC CCT ATC GCC GCG CTG CTC GGC AGT ATT      48
Met Lys Pro Leu Gln Met Pro Pro Ile Ala Ala Leu Leu Gly Ser Ile
                5                   10                  15

TTC GGC AAT CCG GTC TTT GCG GCA GAT GAA GCT GCA ACT GAA ACC ACA      96
Phe Gly Asn Pro Val Phe Ala Ala Asp Glu Ala Ala Thr Glu Thr Thr
            20                  25                  30
```

| | |
|---|---:|
| CCC GTT AAG GCA GAG GTA AAA GCA GTG CGC GTT AAA GGT CAG CGC AAT<br>Pro Val Lys Ala Glu Val Lys Ala Val Arg Val Lys Gly Gln Arg Asn<br>      35                  40                          45 | 144 |
| GCG CCT GCG GCT GTG GAA CGC GTC AAC CTT AAC CGT ATC AAA CAA GAA<br>Ala Pro Ala Ala Val Glu Arg Val Asn Leu Asn Arg Ile Lys Gln Glu<br>50                    55                      60 | 192 |
| ATG ATA CGC GAC AAT AAA GAC TTG GTG CGC TAT TCC ACC GAT GTC GGC<br>Met Ile Arg Asp Asn Lys Asp Leu Val Arg Tyr Ser Thr Asp Val Gly<br>65                    70                      75                      80 | 240 |
| TTG AGC GAC AGG AGC CGT CAT CAA AAA GGC TTT GCC ATT CGC GGC GTG<br>Leu Ser Asp Arg Ser Arg His Gln Lys Gly Phe Ala Ile Arg Gly Val<br>                  85                      90                      95 | 288 |
| GAA GGC GAC CGT GTC GGC GTT AGT ATT GAC GGC GTA AAC CTG CCT GAT<br>Glu Gly Asp Arg Val Gly Val Ser Ile Asp Gly Val Asn Leu Pro Asp<br>             100                     105                    110 | 336 |
| TCC GAA GAA AAC TCG CTG TAC GCC CGT TAT GGC AAC TTC AAC AGC TCG<br>Ser Glu Glu Asn Ser Leu Tyr Ala Arg Tyr Gly Asn Phe Asn Ser Ser<br>             115                     120                    125 | 384 |
| CGT CTG TCT ATC GAC CCC GAA CTC GTG CGC AAC ATC GAC ATC GTA AAA<br>Arg Leu Ser Ile Asp Pro Glu Leu Val Arg Asn Ile Asp Ile Val Lys<br>      130                     135                     140 | 432 |
| GGG GCG GAC TCT TTC AAT ACC GGC AGC GGC GCC TTG GGC GGC GGT GTG<br>Gly Ala Asp Ser Phe Asn Thr Gly Ser Gly Ala Leu Gly Gly Gly Val<br>145                   150                     155                    160 | 480 |
| AAT TAC CAA ACC CTG CAA GGA CGT GAC TTA CTG TTG CCT GAA CGG CAG<br>Asn Tyr Gln Thr Leu Gln Gly Arg Asp Leu Leu Leu Pro Glu Arg Gln<br>                  165                     170                    175 | 528 |
| TTC GGC GTG ATG ATG AAA AAC GGT TAC AGC ACG CGT AAC CGT GAA TGG<br>Phe Gly Val Met Met Lys Asn Gly Tyr Ser Thr Arg Asn Arg Glu Trp<br>                  180                     185                    190 | 576 |
| ACA AAT ACC CTC GGT TTC GGC GTG AGC AAC GAC CGC GTG GAT GCC GCT<br>Thr Asn Thr Leu Gly Phe Gly Val Ser Asn Asp Arg Val Asp Ala Ala<br>             195                     200                    205 | 624 |
| TTG CTG TAT TCG CAA CGG CGC GGC CAT GAA ACT GAA AGC GCG GGC AAG<br>Leu Leu Tyr Ser Gln Arg Arg Gly His Glu Thr Glu Ser Ala Gly Lys<br>      210                     215                     220 | 672 |
| CGT GGT TAT CCG GTA GAG GGT GCT GGT AGC GGA GCG AAT ATC CGT GGT<br>Arg Gly Tyr Pro Val Glu Gly Ala Gly Ser Gly Ala Asn Ile Arg Gly<br>225                   230                     235                    240 | 720 |
| TCT GCG CGC GGT ATT CCT GAT CCG TCC CAA CAC AAA TAC CAC AGC TTC<br>Ser Ala Arg Gly Ile Pro Asp Pro Ser Gln His Lys Tyr His Ser Phe<br>                  245                     250                    255 | 768 |
| TTG GGT AAG ATT GCT TAT CAA ATC AAC GAC AAC CAC CGC ATC GGC GCA<br>Leu Gly Lys Ile Ala Tyr Gln Ile Asn Asp Asn His Arg Ile Gly Ala<br>             260                     265                    270 | 816 |
| TCG CTC AAC GGT CAG CAG GGG CAT AAT TAC ACG GTT GAA GAG TCT TAC<br>Ser Leu Asn Gly Gln Gln Gly His Asn Tyr Thr Val Glu Glu Ser Tyr<br>      275                     280                    285 | 864 |
| AAC CTG CTT GCT TCT TAT TGG CGT GAA GCT GAC GAT GTC AAC AGA CGG<br>Asn Leu Leu Ala Ser Tyr Trp Arg Glu Ala Asp Asp Val Asn Arg Arg<br>             290                     295                    300 | 912 |
| CGT AAC ACC AAC CTC TTT TAC GAA TGG ACG CCG GAA TCC GAC CGG TTG<br>Arg Asn Thr Asn Leu Phe Tyr Glu Trp Thr Pro Glu Ser Asp Arg Leu<br>305                   310                     315                    320 | 960 |
| TCT ATG GTA AAA GCG GAT GTC GAT TAT CAA AAA ACC AAA GTA TCT GCG<br>Ser Met Val Lys Ala Asp Val Asp Tyr Gln Lys Thr Lys Val Ser Ala<br>                  325                     330                    335 | 1008 |

```
GTC AAC TAC AAA GGT TCG TTC CCG ACG AAT TAC ACC ACA TGG GAA ACC    1056
Val Asn Tyr Lys Gly Ser Phe Pro Thr Asn Tyr Thr Thr Trp Glu Thr
        340                 345                 350

GAG TAC CAT AAA AAG GAA GTT GGC GAA ATC TAT AAC CGC AGC ATG GAT    1104
Glu Tyr His Lys Lys Glu Val Gly Glu Ile Tyr Asn Arg Ser Met Asp
            355                 360                 365

ACA ACC TTC AAA CGT ATT ACG CTG CGT ATG GAC AGC CAT CCG TTG CAA    1152
Thr Thr Phe Lys Arg Ile Thr Leu Arg Met Asp Ser His Pro Leu Gln
370                 375                 380

CTC GGG GGG GGG CGA CAC CGC CTG TCG TTT AAA ACC TTT GCC GGG CAG    1200
Leu Gly Gly Gly Arg His Arg Leu Ser Phe Lys Thr Phe Ala Gly Gln
385                 390                 395                 400

CGT GAT TTT GAA AAC TTA AAC CGC GAT GAT TAC TAC TTC AGC GGC CGT    1248
Arg Asp Phe Glu Asn Leu Asn Arg Asp Asp Tyr Tyr Phe Ser Gly Arg
                405                 410                 415

GTT GTT CGA ACC ACC AAC AGT ATC CAG CAT CCG GTG AAA ACC ACC AAC    1296
Val Val Arg Thr Thr Asn Ser Ile Gln His Pro Val Lys Thr Thr Asn
            420                 425                 430

TAC GGT TTC TCG CTG TCC GAC CAA ATC CAA TGG AAC GAC GTG TTC AGT    1344
Tyr Gly Phe Ser Leu Ser Asp Gln Ile Gln Trp Asn Asp Val Phe Ser
        435                 440                 445

AGC CGC GCA GGT ATC CGT TAC GAC CAC ACC AAA ATG ACG CCT CAG GAA    1392
Ser Arg Ala Gly Ile Arg Tyr Asp His Thr Lys Met Thr Pro Gln Glu
450                 455                 460

TTG AAT GCC GAC TGT CAT GCT TGT GAC AAA ACA CCG CCT GCA GCC AAC    1440
Leu Asn Ala Asp Cys His Ala Cys Asp Lys Thr Pro Pro Ala Ala Asn
465                 470                 475                 480

ACT TAT AAA GGC TGG AGC GGA TTT GTC GGC TTG GCG GCG CAG CTG AGC    1488
Thr Tyr Lys Gly Trp Ser Gly Phe Val Gly Leu Ala Ala Gln Leu Ser
                485                 490                 495

CAA ACA TGG CGT GTG GGT TAC GAT GTG ACC TCA GGT TTC CGC GTG CCG    1536
Gln Thr Trp Arg Val Gly Tyr Asp Val Thr Ser Gly Phe Arg Val Pro
            500                 505                 510

AAT GCG TCT GAA GTG TAT TTC ACT TAC AAC CAC GGT TCG GGC ACT TGG    1584
Asn Ala Ser Glu Val Tyr Phe Thr Tyr Asn His Gly Ser Gly Thr Trp
        515                 520                 525

AAG CCT AAT CCT AAT TTG AAG GCA GAA CGC AGC ACC ACC CAC ACC CTG    1632
Lys Pro Asn Pro Asn Leu Lys Ala Glu Arg Ser Thr Thr His Thr Leu
530                 535                 540

TCC TTG CAG GGG CGC GGC GAC AAA GGG ACA CTG GAT GCC AAC CTG TAT    1680
Ser Leu Gln Gly Arg Gly Asp Lys Gly Thr Leu Asp Ala Asn Leu Tyr
545                 550                 555                 560

CAA AGC AAT TAC CGA AAC TTC CTG TCG GAA GAG CAG AAT CTG ACT GTC    1728
Gln Ser Asn Tyr Arg Asn Phe Leu Ser Glu Glu Gln Asn Leu Thr Val
                565                 570                 575

AGC GGC ACA CCC GGC TGT ACT GAG GAG GAT GCT TAC TAC TAT AGA TGC    1776
Ser Gly Thr Pro Gly Cys Thr Glu Glu Asp Ala Tyr Tyr Tyr Arg Cys
            580                 585                 590

AGC GAC CCC TAC AAA GAA AAA CTG GAT TGG CAG ATG AAA AAT ATC GAC    1824
Ser Asp Pro Tyr Lys Glu Lys Leu Asp Trp Gln Met Lys Asn Ile Asp
        595                 600                 605

AAG GCC AGA ATC CGC GGT ATC GAG TTG ACA GGC CGT CTG AAT GTG GAC    1872
Lys Ala Arg Ile Arg Gly Ile Glu Leu Thr Gly Arg Leu Asn Val Asp
610                 615                 620

AAA GTA GCG TCT TTT GTT CCT GAG GGT TGG AAA CTG TTC GGC TCG CTG    1920
Lys Val Ala Ser Phe Val Pro Glu Gly Trp Lys Leu Phe Gly Ser Leu
625                 630                 635                 640
```

```
GGT TAT GCG AAA AGC AAA CTG TCG GGC GAC AAC AGC CTG CTG TCC ACA     1968
Gly Tyr Ala Lys Ser Lys Leu Ser Gly Asp Asn Ser Leu Leu Ser Thr
            645             650                 655

CAG CCG CTG AAA GTG ATT GCC GGT ATC GAC TAT GAA AGT CCG AGC GAA     2016
Gln Pro Leu Lys Val Ile Ala Gly Ile Asp Tyr Glu Ser Pro Ser Glu
            660             665                 670

AAA TGG GGC GTA TTC TCC CGC CTG ACC TAT CTA GGC GCG AAA AAG GTC     2064
Lys Trp Gly Val Phe Ser Arg Leu Thr Tyr Leu Gly Ala Lys Lys Val
            675             680                 685

AAA GAC GCG CAA TAC ACC GTT TAT GAA AAC AAG GGC TGG GGT ACG CCT     2112
Lys Asp Ala Gln Tyr Thr Val Tyr Glu Asn Lys Gly Trp Gly Thr Pro
            690             695                 700

TTG CAG AAA AAG GTA AAA GAT TAC CCG TGG CTG AAC AAG TCG GCT TAT     2160
Leu Gln Lys Lys Val Lys Asp Tyr Pro Trp Leu Asn Lys Ser Ala Tyr
705             710             715                 720

GTG TTT GAT ATG TAC GGC TTC TAC AAA CCG GCT AAA AAC CTG ACT TTG     2208
Val Phe Asp Met Tyr Gly Phe Tyr Lys Pro Ala Lys Asn Leu Thr Leu
            725             730                 735

CGT GCA GGC GTG TAC AAC CTG TTC AAC CGC AAA TAC ACC ACT TGG GAT     2256
Arg Ala Gly Val Tyr Asn Leu Phe Asn Arg Lys Tyr Thr Thr Trp Asp
            740             745                 750

TCC CTG CGC GGT TTA TAT AGC TAC AGC ACC ACC AAT GCG GTC GAC CGC     2304
Ser Leu Arg Gly Leu Tyr Ser Tyr Ser Thr Thr Asn Ala Val Asp Arg
            755             760                 765

GAT GGC AAA GGC TTA GAC CGC TAC CGC GCC CCA GGC CGC AAT TAC GCC     2352
Asp Gly Lys Gly Leu Asp Arg Tyr Arg Ala Pro Gly Arg Asn Tyr Ala
            770             775                 780

GTA TCG CTG GAA TGG AAG TTT TAA                                     2376
Val Ser Leu Glu Trp Lys Phe
785             790
```

(2) INFORMATION FOR SEQ ID NO: 4:

(i) SEQUENCE CHARACTERISTICS:
        (A) LENGTH: 791 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Lys Pro Leu Gln Met Pro Pro Ile Ala Ala Leu Leu Gly Ser Ile
1               5                   10                  15

Phe Gly Asn Pro Val Phe Ala Ala Asp Glu Ala Ala Thr Glu Thr Thr
            20                  25                  30

Pro Val Lys Ala Glu Val Lys Ala Val Arg Val Lys Gly Gln Arg Asn
            35                  40                  45

Ala Pro Ala Ala Val Glu Arg Val Asn Leu Asn Arg Ile Lys Gln Glu
        50                  55                  60

Met Ile Arg Asp Asn Lys Asp Leu Val Arg Tyr Ser Thr Asp Val Gly
65              70                  75                  80

Leu Ser Asp Arg Ser Arg His Gln Lys Gly Phe Ala Ile Arg Gly Val
            85                  90                  95

Glu Gly Asp Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
            115                 120                 125

Arg Leu Ser Ile Asp Pro Glu Leu Val Arg Asn Ile Asp Ile Val Lys
        130                 135                 140
```

-continued

```
Gly Ala Asp Ser Phe Asn Thr Gly Ser Gly Ala Leu Gly Gly Val
145                 150                 155                 160

Asn Tyr Gln Thr Leu Gln Gly Arg Asp Leu Leu Pro Glu Arg Gln
            165                 170                 175

Phe Gly Val Met Met Lys Asn Gly Tyr Ser Thr Arg Asn Arg Glu Trp
                180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Lys
            210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr His Ser Phe
                245                 250                 255

Leu Gly Lys Ile Ala Tyr Gln Ile Asn Asp Asn His Arg Ile Gly Ala
                260                 265                 270

Ser Leu Asn Gly Gln Gln Gly His Asn Tyr Thr Val Glu Glu Ser Tyr
            275                 280                 285

Asn Leu Leu Ala Ser Tyr Trp Arg Glu Ala Asp Asp Val Asn Arg Arg
            290                 295                 300

Arg Asn Thr Asn Leu Phe Tyr Glu Trp Thr Pro Glu Ser Asp Arg Leu
305                 310                 315                 320

Ser Met Val Lys Ala Asp Val Asp Tyr Gln Lys Thr Lys Val Ser Ala
                325                 330                 335

Val Asn Tyr Lys Gly Ser Phe Pro Thr Asn Tyr Thr Thr Trp Glu Thr
                340                 345                 350

Glu Tyr His Lys Lys Glu Val Gly Glu Ile Tyr Asn Arg Ser Met Asp
            355                 360                 365

Thr Thr Phe Lys Arg Ile Thr Leu Arg Met Asp Ser His Pro Leu Gln
370                 375                 380

Leu Gly Gly Gly Arg His Arg Leu Ser Phe Lys Thr Phe Ala Gly Gln
385                 390                 395                 400

Arg Asp Phe Glu Asn Leu Asn Arg Asp Asp Tyr Tyr Phe Ser Gly Arg
                405                 410                 415

Val Val Arg Thr Thr Asn Ser Ile Gln His Pro Val Lys Thr Thr Asn
                420                 425                 430

Tyr Gly Phe Ser Leu Ser Asp Gln Ile Gln Trp Asn Asp Val Phe Ser
            435                 440                 445

Ser Arg Ala Gly Ile Arg Tyr Asp His Thr Lys Met Thr Pro Gln Glu
450                 455                 460

Leu Asn Ala Asp Cys His Ala Cys Asp Lys Thr Pro Pro Ala Ala Asn
465                 470                 475                 480

Thr Tyr Lys Gly Trp Ser Gly Phe Val Gly Leu Ala Ala Gln Leu Ser
            485                 490                 495

Gln Thr Trp Arg Val Gly Tyr Asp Val Thr Ser Gly Phe Arg Val Pro
            500                 505                 510

Asn Ala Ser Glu Val Tyr Phe Thr Tyr Asn His Gly Ser Gly Thr Trp
            515                 520                 525

Lys Pro Asn Pro Asn Leu Lys Ala Glu Arg Ser Thr Thr His Thr Leu
530                 535                 540

Ser Leu Gln Gly Arg Gly Asp Lys Gly Thr Leu Asp Ala Asn Leu Tyr
545                 550                 555                 560
```

-continued

```
Gln Ser Asn Tyr Arg Asn Phe Leu Ser Glu Glu Gln Asn Leu Thr Val
            565                 570                 575

Ser Gly Thr Pro Gly Cys Thr Glu Glu Asp Ala Tyr Tyr Arg Cys
        580                 585                 590

Ser Asp Pro Tyr Lys Glu Lys Leu Asp Trp Gln Met Lys Asn Ile Asp
        595                 600                 605

Lys Ala Arg Ile Arg Gly Ile Glu Leu Thr Gly Arg Leu Asn Val Asp
    610                 615                 620

Lys Val Ala Ser Phe Val Pro Glu Gly Trp Lys Leu Phe Gly Ser Leu
625                 630                 635                 640

Gly Tyr Ala Lys Ser Lys Leu Ser Gly Asp Asn Ser Leu Leu Ser Thr
                645                 650                 655

Gln Pro Leu Lys Val Ile Ala Gly Ile Asp Tyr Glu Ser Pro Ser Glu
            660                 665                 670

Lys Trp Gly Val Phe Ser Arg Leu Thr Tyr Leu Gly Ala Lys Lys Val
            675                 680                 685

Lys Asp Ala Gln Tyr Thr Val Tyr Glu Asn Lys Gly Trp Gly Thr Pro
    690                 695                 700

Leu Gln Lys Lys Val Lys Asp Tyr Pro Trp Leu Asn Lys Ser Ala Tyr
705                 710                 715                 720

Val Phe Asp Met Tyr Gly Phe Tyr Lys Pro Ala Lys Asn Leu Thr Leu
                725                 730                 735

Arg Ala Gly Val Tyr Asn Leu Phe Asn Arg Lys Tyr Thr Thr Trp Asp
                740                 745                 750

Ser Leu Arg Gly Leu Tyr Ser Tyr Ser Thr Thr Asn Ala Val Asp Arg
            755                 760                 765

Asp Gly Lys Gly Leu Asp Arg Tyr Arg Ala Pro Gly Arg Asn Tyr Ala
    770                 775                 780

Val Ser Leu Glu Trp Lys Phe
785                 790
```

(2) INFORMATION FOR SEQ ID NO: 5:

(i) SEQUENCE CHARACTERISTICS:
        (A) LENGTH: 2373 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2370

(xi) SEQUENCE DESCRIPTION: SEQ ID NO: 5:

```
ATG AAA CCA TTA CAA ATG CTC CCT ATC GCC GCG CTG GTC GGC AGT ATT      48
Met Lys Pro Leu Gln Met Leu Pro Ile Ala Ala Leu Val Gly Ser Ile
 1               5                  10                  15

TTC GGC AAT CCG GTC TTA GCG GCA GAT GAA GCT GCA ACT GAA ACC ACA      96
Phe Gly Asn Pro Val Leu Ala Ala Asp Glu Ala Ala Thr Glu Thr Thr
                20                  25                  30

CCC GTT AAG GCA GAG ATA AAA GCA GTG CGC GTT AAA GGC CAG CGC AAT     144
Pro Val Lys Ala Glu Ile Lys Ala Val Arg Val Lys Gly Gln Arg Asn
             35                  40                  45

GCG CCT GCG GCT GTG GAA CGC GTC AAC CTT AAC CGT ATC AAA CAA GAA     192
Ala Pro Ala Ala Val Glu Arg Val Asn Leu Asn Arg Ile Lys Gln Glu
         50                  55                  60
```

```
ATG ATA CGC GAC AAC AAA GAC TTG GTG CGC TAT TCC ACC GAT GTC GGC      240
Met Ile Arg Asp Asn Lys Asp Leu Val Arg Tyr Ser Thr Asp Val Gly
 65          70                  75                  80

TTG AGC GAC AGC GGC CGC CAT CAA AAA GGC TTT GCC GTT CGC GGC GTG      288
Leu Ser Asp Ser Gly Arg His Gln Lys Gly Phe Ala Val Arg Gly Val
             85                  90                  95

GAA GGC AAC CGT GTC GGC GTG AGC ATA GAC GGC GTA AAC CTG CCT GAT      336
Glu Gly Asn Arg Val Gly Val Ser Ile Asp Gly Val Asn Leu Pro Asp
            100                 105                 110

TCC GAA GAA AAC TCG CTG TAC GCC CGT TAT GGC AAC TTC AAC AGC TCG      384
Ser Glu Glu Asn Ser Leu Tyr Ala Arg Tyr Gly Asn Phe Asn Ser Ser
            115                 120                 125

CGT CTG TCT ATC GAC CCC GAA CTC GTG CGC AAC ATC GAA ATC GTA AAA      432
Arg Leu Ser Ile Asp Pro Glu Leu Val Arg Asn Ile Glu Ile Val Lys
130                 135                 140

GGG GCG GAC TCT TTC AAT ACC GGC AGC GGC GCC TTG GGC GGC GGT GTG      480
Gly Ala Asp Ser Phe Asn Thr Gly Ser Gly Ala Leu Gly Gly Gly Val
145                 150                 155                 160

AAT TAC CAA ACC CTG CAA GGA CGT GAC TTA CTG TTG GAT GAT CGG CAG      528
Asn Tyr Gln Thr Leu Gln Gly Arg Asp Leu Leu Leu Asp Asp Arg Gln
                165                 170                 175

TTC GGC GTG ATG ATG AAA AAC GGT TAC AGC ACG CGT AAC CGT GAA TGG      576
Phe Gly Val Met Met Lys Asn Gly Tyr Ser Thr Arg Asn Arg Glu Trp
            180                 185                 190

ACA AAT ACC CTC GGT TTC GGC GTG AGC AAC GAC CGC GTG GAT GCC GCT      624
Thr Asn Thr Leu Gly Phe Gly Val Ser Asn Asp Arg Val Asp Ala Ala
            195                 200                 205

TTG CTG TAT TCG CAA CGG CGC GGC CAT GAA ACT GAA AGC GCG GGC AAC      672
Leu Leu Tyr Ser Gln Arg Arg Gly His Glu Thr Glu Ser Ala Gly Asn
210                 215                 220

CGT GGT TAT CCG GTA GAG GGT GCT GGT AAG GAA ACG AAT ATC CGT GGT      720
Arg Gly Tyr Pro Val Glu Gly Ala Gly Lys Glu Thr Asn Ile Arg Gly
225                 230                 235                 240

TCT GCG CGC GGT ATT CCT GAT CCG TCC AAA CAC AAA TAC CAC AAC TTC      768
Ser Ala Arg Gly Ile Pro Asp Pro Ser Lys His Lys Tyr His Asn Phe
                245                 250                 255

TTG GGT AAG ATT GCT TAT CAA ATC AAC GAC AAC CAC CGC ATC GGC GCA      816
Leu Gly Lys Ile Ala Tyr Gln Ile Asn Asp Asn His Arg Ile Gly Ala
            260                 265                 270

TCG CTC AAC GGT CAG CAG GGG CAT AAT TAC ACG GTT GAA GAG TCT TAC      864
Ser Leu Asn Gly Gln Gln Gly His Asn Tyr Thr Val Glu Glu Ser Tyr
            275                 280                 285

AAC CTG ACT GCT TCT TCT TGG CGT GAA GCT GAC GAT GTC AAC AGA CGG      912
Asn Leu Thr Ala Ser Ser Trp Arg Glu Ala Asp Asp Val Asn Arg Arg
290                 295                 300

CGT AAC GCC AAC CTC TTT TAC GAA TGG ATG CCG GAA TCC AAC TGG TTG      960
Arg Asn Ala Asn Leu Phe Tyr Glu Trp Met Pro Glu Ser Asn Trp Leu
305                 310                 315                 320

TCT AGC CTA AAA GCG GAT TTC GAT TAT CAA AAA ACC AAA GTA GCT GCG     1008
Ser Ser Leu Lys Ala Asp Phe Asp Tyr Gln Lys Thr Lys Val Ala Ala
                325                 330                 335

ATC AAC AAA GGT TCG TTC CCG ACA AAT TAT ACC ACC TGG GAA ACT GAA     1056
Ile Asn Lys Gly Ser Phe Pro Thr Asn Tyr Thr Thr Trp Glu Thr Glu
            340                 345                 350

TAC CAT AAA AAG GAA GTG GGT GAA ATC TAC AAC CGC AGT ATG GAT ACC     1104
Tyr His Lys Lys Glu Val Gly Glu Ile Tyr Asn Arg Ser Met Asp Thr
            355                 360                 365
```

```
CGC TTC AAA CGT TTT ACG CTG CGT TTG GAC AGC CAT CCG TTG CAA CTC      1152
Arg Phe Lys Arg Phe Thr Leu Arg Leu Asp Ser His Pro Leu Gln Leu
    370                 375                 380

GGG GGG GGG CGA CAC CGC CTG TCG TTT AAA ACT TTC GCC AGC CGC CGT      1200
Gly Gly Gly Arg His Arg Leu Ser Phe Lys Thr Phe Ala Ser Arg Arg
385                 390                 395                 400

GAT TTT GAA AAC CTA AAC CGC GAC GAT TAC TAC TTC AGC GGC CGT GTT      1248
Asp Phe Glu Asn Leu Asn Arg Asp Asp Tyr Tyr Phe Ser Gly Arg Val
                405                 410                 415

GTT CGA ACC ACC AGC AGT ATC CAG CAT CCG GTG AAA ACC ACC AAC TAC      1296
Val Arg Thr Thr Ser Ser Ile Gln His Pro Val Lys Thr Thr Asn Tyr
            420                 425                 430

GGT TTC TCA CTG TCT GAC CAA ATT CAA TGG AAC GAC GTG TTC AGT AGC      1344
Gly Phe Ser Leu Ser Asp Gln Ile Gln Trp Asn Asp Val Phe Ser Ser
                435                 440                 445

CGC GCA GGT ATC CGT TAC GAT CAT ACC AAA ATG ACG CCT CAG GAA TTG      1392
Arg Ala Gly Ile Arg Tyr Asp His Thr Lys Met Thr Pro Gln Glu Leu
450                 455                 460

AAT GCC GAG TGT CAT GCT TGT GAC AAA ACA CCG CCT GCA GCC AAC ACT      1440
Asn Ala Glu Cys His Ala Cys Asp Lys Thr Pro Pro Ala Ala Asn Thr
465                 470                 475                 480

TAT AAA GGC TGG AGC GGT TTT GTC GGC TTG GCG GCG CAA CTG AAT CAG      1488
Tyr Lys Gly Trp Ser Gly Phe Val Gly Leu Ala Ala Gln Leu Asn Gln
                485                 490                 495

GCT TGG CGT GTC GGT TAC GAC ATT ACT TCC GGC TAC CGT GTC CCC AAT      1536
Ala Trp Arg Val Gly Tyr Asp Ile Thr Ser Gly Tyr Arg Val Pro Asn
            500                 505                 510

GCG TCC GAA GTG TAT TTC ACT TAC AAC CAC GGT TCG GGT AAT TGG CTG      1584
Ala Ser Glu Val Tyr Phe Thr Tyr Asn His Gly Ser Gly Asn Trp Leu
                515                 520                 525

CCC AAT CCC AAC CTG AAA GCC GAG CGC AGC ACC ACC CAC ACC CTC TCT      1632
Pro Asn Pro Asn Leu Lys Ala Glu Arg Ser Thr Thr His Thr Leu Ser
530                 535                 540

CTG CAA GGC CGC AGC GAA AAA GGT ATG TTG GAT GCC AAC CTG TAT CAA      1680
Leu Gln Gly Arg Ser Glu Lys Gly Met Leu Asp Ala Asn Leu Tyr Gln
545                 550                 555                 560

AGC AAT TAC CGA AAT TTC CTG TCT GAA GAG CAG AAG CTG ACC ACC AGC      1728
Ser Asn Tyr Arg Asn Phe Leu Ser Glu Glu Gln Lys Leu Thr Thr Ser
                565                 570                 575

GGC ACT CCC GGC TGT ACT GAG GAG AAT GCC TAC TAC AGT ATT TGT AGC      1776
Gly Thr Pro Gly Cys Thr Glu Glu Asn Ala Tyr Tyr Ser Ile Cys Ser
            580                 585                 590

GAT CCT TAT AAG GAA AAA CTG GAT TGG CAG ATG AAA AAT ATC GAC AAG      1824
Asp Pro Tyr Lys Glu Lys Leu Asp Trp Gln Met Lys Asn Ile Asp Lys
                595                 600                 605

GCC AGA ATC CGC GGT ATC GAG CTG ACG GGC CGT CTG AAT GTG GAC AAA      1872
Ala Arg Ile Arg Gly Ile Glu Leu Thr Gly Arg Leu Asn Val Asp Lys
610                 615                 620

GTA GCG TCT TTT GTT CCT GAG GGC TGG AAA CTG TTC GGC TCG CTG GGT      1920
Val Ala Ser Phe Val Pro Glu Gly Trp Lys Leu Phe Gly Ser Leu Gly
625                 630                 635                 640

TAT GCG AAA AGC AAA CTG TCG GGC GAC AAC AGC CTG CTG TCC ACC CAG      1968
Tyr Ala Lys Ser Lys Leu Ser Gly Asp Asn Ser Leu Leu Ser Thr Gln
                645                 650                 655

CCG TTG AAA GTG ATT GCC GGT ATC GAC TAT GAA AGT CCG AGC GAA AAA      2016
Pro Leu Lys Val Ile Ala Gly Ile Asp Tyr Glu Ser Pro Ser Glu Lys
            660                 665                 670

TGG GGC GTG TTC TCC CGC CTG ACC TAT CTG GGC GCG AAA AAG GTC AAA      2064
Trp Gly Val Phe Ser Arg Leu Thr Tyr Leu Gly Ala Lys Lys Val Lys
                675                 680                 685
```

```
GAC GCG CAA TAC ACC GTT TAT GAA AAC AAG GGC TGG GGT ACG CCT TTG      2112
Asp Ala Gln Tyr Thr Val Tyr Glu Asn Lys Gly Trp Gly Thr Pro Leu
690                 695                 700

CAG AAA AAG GTA AAA GAT TAC CCG TGG CTG AAC AAG TCG GCT TAT GTG      2160
Gln Lys Lys Val Lys Asp Tyr Pro Trp Leu Asn Lys Ser Ala Tyr Val
705                 710                 715                 720

TTC GAT ATG TAC GGC TTC TAC AAA CCG GTG AAA AAC CTG ACT TTG CGT      2208
Phe Asp Met Tyr Gly Phe Tyr Lys Pro Val Lys Asn Leu Thr Leu Arg
                725                 730                 735

GCA GGC GTA TAT AAT TTG TTC AAC CGC AAA TAC ACC ACT TGG GAT TCC      2256
Ala Gly Val Tyr Asn Leu Phe Asn Arg Lys Tyr Thr Thr Trp Asp Ser
            740                 745                 750

CTG CGC GGC CTG TAT AGC TAC AGC ACC ACC AAC GCG GTC GAC CGC GAT      2304
Leu Arg Gly Leu Tyr Ser Tyr Ser Thr Thr Asn Ala Val Asp Arg Asp
        755                 760                 765

GGC AAA GGC TTA GAC CGC TAC CGC GCC CCA GGC CGT AAT TAC GCC GTA      2352
Gly Lys Gly Leu Asp Arg Tyr Arg Ala Pro Gly Arg Asn Tyr Ala Val
    770                 775                 780

TCG CTG GAA TGG AAG TTT TAA                                          2373
Ser Leu Glu Trp Lys Phe
785                 790
```

(2) INFORMATION FOR SEQ ID NO: 6:

(i) SEQUENCE CHARACTERISTICS:
        (A) LENGTH: 790 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Asp Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205
```

-continued

```
Leu Leu Tyr Ser Gln Arg Arg Gly His Glu Thr Glu Ser Ala Gly Asn
    210                 215                 220
Arg Gly Tyr Pro Val Glu Gly Ala Gly Lys Glu Thr Asn Ile Arg Gly
225                 230                 235                 240
Ser Ala Arg Gly Ile Pro Asp Pro Ser Lys His Lys Tyr His Asn Phe
                245                 250                 255
Leu Gly Lys Ile Ala Tyr Gln Ile Asn Asp Asn His Arg Ile Gly Ala
                260                 265                 270
Ser Leu Asn Gly Gln Gln Gly His Asn Tyr Thr Val Glu Glu Ser Tyr
            275                 280                 285
Asn Leu Thr Ala Ser Ser Trp Arg Glu Ala Asp Asp Val Asn Arg Arg
    290                 295                 300
Arg Asn Ala Asn Leu Phe Tyr Glu Trp Met Pro Glu Ser Asn Trp Leu
305                 310                 315                 320
Ser Ser Leu Lys Ala Asp Phe Asp Tyr Gln Lys Thr Lys Val Ala Ala
                325                 330                 335
Ile Asn Lys Gly Ser Phe Pro Thr Asn Tyr Thr Thr Trp Glu Thr Glu
                340                 345                 350
Tyr His Lys Lys Glu Val Gly Glu Ile Tyr Asn Arg Ser Met Asp Thr
            355                 360                 365
Arg Phe Lys Arg Phe Thr Leu Arg Leu Asp Ser His Pro Leu Gln Leu
    370                 375                 380
Gly Gly Gly Arg His Arg Leu Ser Phe Lys Thr Phe Ala Ser Arg Arg
385                 390                 395                 400
Asp Phe Glu Asn Leu Asn Arg Asp Asp Tyr Tyr Phe Ser Gly Arg Val
                405                 410                 415
Val Arg Thr Thr Ser Ser Ile Gln His Pro Val Lys Thr Thr Asn Tyr
            420                 425                 430
Gly Phe Ser Leu Ser Asp Gln Ile Gln Trp Asn Asp Val Phe Ser Ser
    435                 440                 445
Arg Ala Gly Ile Arg Tyr Asp His Thr Lys Met Thr Pro Gln Glu Leu
    450                 455                 460
Asn Ala Glu Cys His Ala Cys Asp Lys Thr Pro Pro Ala Ala Asn Thr
465                 470                 475                 480
Tyr Lys Gly Trp Ser Gly Phe Val Gly Leu Ala Ala Gln Leu Asn Gln
                485                 490                 495
Ala Trp Arg Val Gly Tyr Asp Ile Thr Ser Gly Tyr Arg Val Pro Asn
                500                 505                 510
Ala Ser Glu Val Tyr Phe Thr Tyr Asn His Gly Ser Gly Asn Trp Leu
            515                 520                 525
Pro Asn Pro Asn Leu Lys Ala Glu Arg Ser Thr Thr His Thr Leu Ser
    530                 535                 540
Leu Gln Gly Arg Ser Glu Lys Gly Met Leu Asp Ala Asn Leu Tyr Gln
545                 550                 555                 560
Ser Asn Tyr Arg Asn Phe Leu Ser Glu Glu Gln Lys Leu Thr Thr Ser
                565                 570                 575
Gly Thr Pro Gly Cys Thr Glu Glu Asn Ala Tyr Tyr Ser Ile Cys Ser
                580                 585                 590
Asp Pro Tyr Lys Glu Lys Leu Asp Trp Gln Met Lys Asn Ile Asp Lys
            595                 600                 605
Ala Arg Ile Arg Gly Ile Glu Leu Thr Gly Arg Leu Asn Val Asp Lys
    610                 615                 620
```

-continued

```
Val Ala Ser Phe Val Pro Glu Gly Trp Lys Leu Phe Gly Ser Leu Gly
625                 630                 635                 640

Tyr Ala Lys Ser Lys Leu Ser Gly Asp Asn Ser Leu Leu Ser Thr Gln
                645                 650                 655

Pro Leu Lys Val Ile Ala Gly Ile Asp Tyr Glu Ser Pro Ser Glu Lys
            660                 665                 670

Trp Gly Val Phe Ser Arg Leu Thr Tyr Leu Gly Ala Lys Lys Val Lys
        675                 680                 685

Asp Ala Gln Tyr Thr Val Tyr Glu Asn Lys Gly Trp Gly Thr Pro Leu
690                 695                 700

Gln Lys Lys Val Lys Asp Tyr Pro Trp Leu Asn Lys Ser Ala Tyr Val
705                 710                 715                 720

Phe Asp Met Tyr Gly Phe Tyr Lys Pro Val Lys Asn Leu Thr Leu Arg
                725                 730                 735

Ala Gly Val Tyr Asn Leu Phe Asn Arg Lys Tyr Thr Thr Trp Asp Ser
            740                 745                 750

Leu Arg Gly Leu Tyr Ser Tyr Ser Thr Thr Asn Ala Val Asp Arg Asp
        755                 760                 765

Gly Lys Gly Leu Asp Arg Tyr Arg Ala Pro Gly Arg Asn Tyr Ala Val
770                 775                 780

Ser Leu Glu Trp Lys Phe
785                 790
```

(2) INFORMATION FOR SEQ ID NO: 7:

(i) SEQUENCE CHARACTERISTICS:
        (A) LENGTH: 2378 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2370

(xi) SEQUENCE DESCRIPTION: SEQ ID NO: 7:

```
ATG AAA CCA TTA CAC ATG CTT CCT ATT GCC GCG CTG GTC GGC AGT ATT      48
Met Lys Pro Leu His Met Leu Pro Ile Ala Ala Leu Val Gly Ser Ile
            5                   10                  15

TTC GGC AAT CCG GTC TTG GCA GCG GAT GAA GCT GCA ACC GAA ACC ACA      96
Phe Gly Asn Pro Val Leu Ala Ala Asp Glu Ala Ala Thr Glu Thr Thr
        20                  25                  30

CCC GTT AAA GCA GAG ATA AAA GAA GTG CGC GTT AAA GAC CAG CTT AAT     144
Pro Val Lys Ala Glu Ile Lys Glu Val Arg Val Lys Asp Gln Leu Asn
    35                  40                  45

GCG CCT GCA ACC GTG GAA CGT GTC AAC CTC GGC CGC ATT CAA CAG GAA     192
Ala Pro Ala Thr Val Glu Arg Val Asn Leu Gly Arg Ile Gln Gln Glu
50                  55                  60

ATG ATA CGC GAC AAC AAA GAC TTG GTG CGT TAC TCC ACC GAC GTC GGC     240
Met Ile Arg Asp Asn Lys Asp Leu Val Arg Tyr Ser Thr Asp Val Gly
65                  70                  75                  80

TTG AGC GAT AGC GGC CGC CAT CAA AAA GGC TTT GCT GTG CGC GGC GTG     288
Leu Ser Asp Ser Gly Arg His Gln Lys Gly Phe Ala Val Arg Gly Val
                85                  90                  95

GAA GGC AAC CGT GTC GGT GTC AGC ATT GAC GGC GTG AGC CTG CCT GAT     336
Glu Gly Asn Arg Val Gly Val Ser Ile Asp Gly Val Ser Leu Pro Asp
            100                 105                 110
```

```
TCG GAA GAA AAC TCA CTG TAT GCA CGT TAT GGC AAC TTC AAC AGC TCG      384
Ser Glu Glu Asn Ser Leu Tyr Ala Arg Tyr Gly Asn Phe Asn Ser Ser
            115                 120                 125

CGC CTG TCT ATC GAC CCC GAA CTC GTG CGC AAC ATC GAA ATC GCG AAG      432
Arg Leu Ser Ile Asp Pro Glu Leu Val Arg Asn Ile Glu Ile Ala Lys
            130                 135                 140

GGC GCT GAC TCT TTC AAT ACC GGT AGC GGC GCA TTG GGT GGC GGC GTG      480
Gly Ala Asp Ser Phe Asn Thr Gly Ser Gly Ala Leu Gly Gly Gly Val
145                 150                 155                 160

AAT TAC CAA ACC CTG CAA GGA CAT GAT TTG CTG TTG GAC GAC AGG CAA      528
Asn Tyr Gln Thr Leu Gln Gly His Asp Leu Leu Leu Asp Asp Arg Gln
            165                 170                 175

TTC GGC GTG ATG ATG AAA AAC GGT TAC AGC AGC CGC AAC CGC GAA TGG      576
Phe Gly Val Met Met Lys Asn Gly Tyr Ser Ser Arg Asn Arg Glu Trp
            180                 185                 190

ACA AAT ACA CTC GGT TTC GGT GTG AGC AAC GAC CGC GTG GAT GCC GCT      624
Thr Asn Thr Leu Gly Phe Gly Val Ser Asn Asp Arg Val Asp Ala Ala
            195                 200                 205

TTG CTG TAT TCG CAA CGT CGC GGT CAT GAG ACC GAA AGC GCG GGC GAG      672
Leu Leu Tyr Ser Gln Arg Arg Gly His Glu Thr Glu Ser Ala Gly Glu
            210                 215                 220

CGT GGC TAT CCG GTA GAG GGT GCT GGC AGC GGA GCA ATT ATC CGT GGT      720
Arg Gly Tyr Pro Val Glu Gly Ala Gly Ser Gly Ala Ile Ile Arg Gly
225                 230                 235                 240

TCG TCA CGC GGT ATC CCT GAT CCG TCC AAA CAC AAA TAC CAC AAC TTC      768
Ser Ser Arg Gly Ile Pro Asp Pro Ser Lys His Lys Tyr His Asn Phe
            245                 250                 255

TTG GGT AAG ATT GCT TAT CAA ATC AAC GAC AAG CAC CGC ATC GGC CCA      816
Leu Gly Lys Ile Ala Tyr Gln Ile Asn Asp Lys His Arg Ile Gly Pro
            260                 265                 270

TCG TTT AAC GGC CAG CAG GGG CAT AAT TAC ACG ATT GAA GAG TCT TAT      864
Ser Phe Asn Gly Gln Gln Gly His Asn Tyr Thr Ile Glu Glu Ser Tyr
            275                 280                 285

AAC CTG ACC GCT TCT TCC TGG CGC GAA GCC GAT GAC GTA AAC AGA CGG      912
Asn Leu Thr Ala Ser Ser Trp Arg Glu Ala Asp Asp Val Asn Arg Arg
            290                 295                 300

CGC AAT GCC AAC CTC TTT TAC GAA TGG ACG CCT GAT TCA AAT TGG CTG      960
Arg Asn Ala Asn Leu Phe Tyr Glu Trp Thr Pro Asp Ser Asn Trp Leu
305                 310                 315                 320

TCG TCT TTG AAG GCG GAT TTC GAT TAT CAG ACA ACC AAA GTG GCG GCG     1008
Ser Ser Leu Lys Ala Asp Phe Asp Tyr Gln Thr Thr Lys Val Ala Ala
            325                 330                 335

GTT AAC AAC AAA GGC TCG TTC CCG ACG GAT TAT TCC ACC TGG ACG CGC     1056
Val Asn Asn Lys Gly Ser Phe Pro Thr Asp Tyr Ser Thr Trp Thr Arg
            340                 345                 350

AAC TAT AAT CAG AAG GAT TTG GAG AAT ATA TAC AAC CGC AGC ATG GAC     1104
Asn Tyr Asn Gln Lys Asp Leu Glu Asn Ile Tyr Asn Arg Ser Met Asp
            355                 360                 365

ACC CGA TTC AAA CGT TTT ACT TTG CGT ATG GAC AGC CAA CCG TTG CAA     1152
Thr Arg Phe Lys Arg Phe Thr Leu Arg Met Asp Ser Gln Pro Leu Gln
            370                 375                 380

CTG GGC GGC CGA CAT CGC TTG TCG CTT AAA ACT TTC GCC AGT CGG CGT     1200
Leu Gly Gly Arg His Arg Leu Ser Leu Lys Thr Phe Ala Ser Arg Arg
385                 390                 395                 400

GAG TTT GAA AAC TTA AAC CGC GAC GAT TAT TAC TTC AGC GAA AGA GTA     1248
Glu Phe Glu Asn Leu Asn Arg Asp Asp Tyr Tyr Phe Ser Glu Arg Val
            405                 410                 415
```

|   |   |   |   |   |   |   |   |   |   |   |   |   |   |   |   |      |
|---|---|---|---|---|---|---|---|---|---|---|---|---|---|---|---|------|
| TCC | CGT | ACT | ACC | AGC | TCG | ATT | CAA | CAC | CCC | GTG | AAA | ACC | ACT | AAT | TAT | 1296 |
| Ser | Arg | Thr | Thr | Ser | Ser | Ile | Gln | His | Pro | Val | Lys | Thr | Thr | Asn | Tyr |      |
|     |     | 420 |     |     |     |     | 425 |     |     |     |     | 430 |     |     |     |      |
| GGT | TTC | TCA | CTG | TCT | GAT | CAA | ATC | CAA | TGG | AAC | GAC | GTG | TTC | AGC | AGC | 1344 |
| Gly | Phe | Ser | Leu | Ser | Asp | Gln | Ile | Gln | Trp | Asn | Asp | Val | Phe | Ser | Ser |      |
|     |     | 435 |     |     |     |     | 440 |     |     |     |     | 445 |     |     |     |      |
| CGT | GCA | GAT | ATC | CGT | TAC | GAT | CAT | ACC | AAA | ATG | ACG | CCT | CAG | GAA | TTG | 1392 |
| Arg | Ala | Asp | Ile | Arg | Tyr | Asp | His | Thr | Lys | Met | Thr | Pro | Gln | Glu | Leu |      |
|     | 450 |     |     |     |     | 455 |     |     |     |     | 460 |     |     |     |     |      |
| AAT | GCC | GAC | TGT | CAT | GCT | TGT | GAC | AAA | ACA | CCG | CCT | GCA | GCC | AAT | ACT | 1440 |
| Asn | Ala | Asp | Cys | His | Ala | Cys | Asp | Lys | Thr | Pro | Pro | Ala | Ala | Asn | Thr |      |
| 465 |     |     |     | 470 |     |     |     |     | 475 |     |     |     |     | 480 |     |      |
| TAT | AAA | GGC | TGG | AGC | GGA | TTT | GTC | GGT | TTG | GCG | GCG | CAA | CTG | AAT | CAG | 1488 |
| Tyr | Lys | Gly | Trp | Ser | Gly | Phe | Val | Gly | Leu | Ala | Ala | Gln | Leu | Asn | Gln |      |
|     |     |     |     | 485 |     |     |     |     | 490 |     |     |     |     | 495 |     |      |
| GCT | TGG | CAT | GTC | GGT | TAC | GAC | ATT | ACT | TCC | GGC | TAC | CGT | GTC | CCC | AAT | 1536 |
| Ala | Trp | His | Val | Gly | Tyr | Asp | Ile | Thr | Ser | Gly | Tyr | Arg | Val | Pro | Asn |      |
|     |     |     | 500 |     |     |     |     | 505 |     |     |     |     | 510 |     |     |      |
| GCG | TCC | GAA | GTG | TAT | TTC | ACT | TAC | AAC | CAC | GGT | TCG | GGT | AAT | TGG | CTG | 1584 |
| Ala | Ser | Glu | Val | Tyr | Phe | Thr | Tyr | Asn | His | Gly | Ser | Gly | Asn | Trp | Leu |      |
|     |     | 515 |     |     |     |     | 520 |     |     |     |     | 525 |     |     |     |      |
| CCC | AAT | CCC | AAC | CTG | AAA | GCC | GAG | CGC | AGC | ACC | ACC | CAC | ACC | CTG | TCT | 1632 |
| Pro | Asn | Pro | Asn | Leu | Lys | Ala | Glu | Arg | Ser | Thr | Thr | His | Thr | Leu | Ser |      |
|     | 530 |     |     |     |     | 535 |     |     |     |     | 540 |     |     |     |     |      |
| CTG | CAA | GGC | CGC | AGC | GAA | AAA | GGT | ACT | TTG | GAT | GCC | AAC | CTG | TAT | CAA | 1680 |
| Leu | Gln | Gly | Arg | Ser | Glu | Lys | Gly | Thr | Leu | Asp | Ala | Asn | Leu | Tyr | Gln |      |
| 545 |     |     |     |     | 550 |     |     |     |     | 555 |     |     |     |     | 560 |      |
| AAC | AAT | TAC | CGA | AAC | TTC | TTG | TCT | GAA | GAG | CAG | AAC | CTG | ACC | ACC | AGC | 1728 |
| Asn | Asn | Tyr | Arg | Asn | Phe | Leu | Ser | Glu | Glu | Gln | Asn | Leu | Thr | Thr | Ser |      |
|     |     |     |     | 565 |     |     |     |     | 570 |     |     |     |     | 575 |     |      |
| GGC | GAT | GTC | GGC | TGT | ACT | CAG | ATG | AAT | TAC | TAC | TAC | GGT | ATG | TGT | AGC | 1776 |
| Gly | Asp | Val | Gly | Cys | Thr | Gln | Met | Asn | Tyr | Tyr | Tyr | Gly | Met | Cys | Ser |      |
|     |     |     | 580 |     |     |     |     | 585 |     |     |     |     | 590 |     |     |      |
| AAT | CCT | TAT | TCC | GAA | AAA | CCG | GAA | TGG | CAG | ATG | CAA | AAT | ATC | GAT | AAG | 1824 |
| Asn | Pro | Tyr | Ser | Glu | Lys | Pro | Glu | Trp | Gln | Met | Gln | Asn | Ile | Asp | Lys |      |
|     |     | 595 |     |     |     |     | 600 |     |     |     |     | 605 |     |     |     |      |
| GCC | CGA | ATC | CGT | GGT | CTT | GAG | CTG | ACG | GGC | CGT | CTG | AAT | GTG | ACA | AAA | 1872 |
| Ala | Arg | Ile | Arg | Gly | Leu | Glu | Leu | Thr | Gly | Arg | Leu | Asn | Val | Thr | Lys |      |
|     | 610 |     |     |     |     | 615 |     |     |     |     | 620 |     |     |     |     |      |
| GTA | GCG | TCT | TTT | GTT | CCT | GAG | GGC | TGG | AAA | TTG | TTC | GGC | TCG | CTG | GGT | 1920 |
| Val | Ala | Ser | Phe | Val | Pro | Glu | Gly | Trp | Lys | Leu | Phe | Gly | Ser | Leu | Gly |      |
| 625 |     |     |     |     | 630 |     |     |     |     | 635 |     |     |     |     | 640 |      |
| TAT | GCG | AAA | AGC | AAA | CTG | TCG | GGC | GAC | AAC | AGC | CTG | CTG | TCC | ACA | CAG | 1968 |
| Tyr | Ala | Lys | Ser | Lys | Leu | Ser | Gly | Asp | Asn | Ser | Leu | Leu | Ser | Thr | Gln |      |
|     |     |     |     | 645 |     |     |     |     | 650 |     |     |     |     | 655 |     |      |
| CCG | CCG | AAA | GTG | ATT | GCC | GGT | ATC | GAC | TAT | GAA | AGT | CCG | AGC | GAA | AAA | 2016 |
| Pro | Pro | Lys | Val | Ile | Ala | Gly | Ile | Asp | Tyr | Glu | Ser | Pro | Ser | Glu | Lys |      |
|     |     |     | 660 |     |     |     |     | 665 |     |     |     |     | 670 |     |     |      |
| TGG | GGT | GTG | TTC | TCC | CGC | CTG | ACT | TAT | CTG | GGT | GCG | AAA | AAG | GCC | AAA | 2064 |
| Trp | Gly | Val | Phe | Ser | Arg | Leu | Thr | Tyr | Leu | Gly | Ala | Lys | Lys | Ala | Lys |      |
|     |     |     | 675 |     |     |     |     | 680 |     |     |     |     | 685 |     |     |      |
| GAC | GCG | CAA | TAC | ACC | GTT | TAT | GAA | AAC | AAG | GGC | CGG | GGT | ACG | CCT | TTG | 2112 |
| Asp | Ala | Gln | Tyr | Thr | Val | Tyr | Glu | Asn | Lys | Gly | Arg | Gly | Thr | Pro | Leu |      |
|     | 690 |     |     |     |     | 695 |     |     |     |     | 700 |     |     |     |     |      |
| CAG | AAA | AAG | GTA | AAA | GAT | TAC | CCG | TGG | CTG | AAC | AAG | TCG | GCT | TAT | GTG | 2160 |
| Gln | Lys | Lys | Val | Lys | Asp | Tyr | Pro | Trp | Leu | Asn | Lys | Ser | Ala | Tyr | Val |      |
| 705 |     |     |     | 710 |     |     |     |     | 715 |     |     |     |     | 720 |     |      |

```
TTT GAT ATG TAC GGC TTC TAC AAA CTG GCT AAA AAC CTG ACT TTG CGT     2208
Phe Asp Met Tyr Gly Phe Tyr Lys Leu Ala Lys Asn Leu Thr Leu Arg
                725                 730                 735

GCA GGC GTA TAT AAT GTG TTC AAC CGC AAA TAC ACC ACT TGG GAT TCC     2256
Ala Gly Val Tyr Asn Val Phe Asn Arg Lys Tyr Thr Thr Trp Asp Ser
            740                 745                 750

CTG CGC GGT TTG TAT AGC TAC AGC ACC ACC AAC GCG GTC GAC CGA GAT     2304
Leu Arg Gly Leu Tyr Ser Tyr Ser Thr Thr Asn Ala Val Asp Arg Asp
        755                 760                 765

GGC AAA GGC TTA GAC CGC TAC CGC GCC TCA GGC CGT AAT TAC GCC GTA     2352
Gly Lys Gly Leu Asp Arg Tyr Arg Ala Ser Gly Arg Asn Tyr Ala Val
    770                 775                 780

TCG CTG GAT TGG AAG TTT TGAATTCC                                    2378
Ser Leu Asp Trp Lys Phe
785                 790

(2) INFORMATION FOR SEQ ID NO: 8:

(i) SEQUENCE CHARACTERISTICS:
        (A) LENGTH: 790 amino acids
        (B) TYPE: amino acid
        (D) TOPOLOGY: linear (ii) MOLECULE TYPE: protein (xi) SEQUENCE DESCRIPTION: SEQ ID NO: 8:

Met Lys Pro Leu His Met Leu Pro Ile Ala Ala Leu Val Gly Ser Ile
 1               5                  10                  15

Phe Gly Asn Pro Val Leu Ala Ala Asp Glu Ala Ala Thr Glu Thr Thr
                20                  25                  30

Pro Val Lys Ala Glu Ile Lys Glu Val Arg Val Lys Asp Gln Leu Asn
            35                  40                  45

Ala Pro Ala Thr Val Glu Arg Val Asn Leu Gly Arg Ile Gln Gln Glu
        50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Ser Leu Pro Asp
                100                 105                 110

Ser Glu Glu Asn Ser Leu Tyr Ala Arg Tyr Gly Asn Phe Asn Ser Ser
            115                 120                 125

Arg Leu Ser Ile Asp Pro Glu Leu Val Arg Asn Ile Glu Ile Ala Lys
        130                 135                 140

Gly Ala Asp Ser Phe Asn Thr Gly Ser Gly Ala Leu Gly Gly Gly Val
145                 150                 155                 160

Asn Tyr Gln Thr Leu Gln Gly His Asp Leu Leu Leu Asp Asp Arg Gln
                165                 170                 175

Phe Gly Val Met Met Lys Asn Gly Tyr Ser Ser Arg Asn Arg Glu Trp
                180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Glu
        210                 215                 220

Arg Gly Tyr Pro Val Glu Gly Ala Gly Ser Gly Ala Ile Ile Arg Gly
225                 230                 235                 240
```

-continued

```
Ser Ser Arg Gly Ile Pro Asp Pro Ser Lys His Lys Tyr His Asn Phe
            245                 250                 255
Leu Gly Lys Ile Ala Tyr Gln Ile Asn Asp Lys His Arg Ile Gly Pro
            260                 265                 270
Ser Phe Asn Gly Gln Gln Gly His Asn Tyr Thr Ile Glu Glu Ser Tyr
            275                 280                 285
Asn Leu Thr Ala Ser Ser Trp Arg Glu Ala Asp Asp Val Asn Arg Arg
            290                 295                 300
Arg Asn Ala Asn Leu Phe Tyr Glu Trp Thr Pro Asp Ser Asn Trp Leu
305                 310                 315                 320
Ser Ser Leu Lys Ala Asp Phe Asp Tyr Gln Thr Thr Lys Val Ala Ala
            325                 330                 335
Val Asn Asn Lys Gly Ser Phe Pro Thr Asp Tyr Ser Thr Trp Thr Arg
            340                 345                 350
Asn Tyr Asn Gln Lys Asp Leu Glu Asn Ile Tyr Asn Arg Ser Met Asp
            355                 360                 365
Thr Arg Phe Lys Arg Phe Thr Leu Arg Met Asp Ser Gln Pro Leu Gln
            370                 375                 380
Leu Gly Gly Arg His Arg Leu Ser Leu Lys Thr Phe Ala Ser Arg Arg
385                 390                 395                 400
Glu Phe Glu Asn Leu Asn Arg Asp Asp Tyr Tyr Phe Ser Glu Arg Val
            405                 410                 415
Ser Arg Thr Thr Ser Ser Ile Gln His Pro Val Lys Thr Thr Asn Tyr
            420                 425                 430
Gly Phe Ser Leu Ser Asp Gln Ile Gln Trp Asn Asp Val Phe Ser Ser
            435                 440                 445
Arg Ala Asp Ile Arg Tyr Asp His Thr Lys Met Thr Pro Gln Glu Leu
            450                 455                 460
Asn Ala Asp Cys His Ala Cys Asp Lys Thr Pro Pro Ala Ala Asn Thr
465                 470                 475                 480
Tyr Lys Gly Trp Ser Gly Phe Val Gly Leu Ala Ala Gln Leu Asn Gln
            485                 490                 495
Ala Trp His Val Gly Tyr Asp Ile Thr Ser Gly Tyr Arg Val Pro Asn
            500                 505                 510
Ala Ser Glu Val Tyr Phe Thr Tyr Asn His Gly Ser Gly Asn Trp Leu
            515                 520                 525
Pro Asn Pro Asn Leu Lys Ala Glu Arg Ser Thr Thr His Thr Leu Ser
530                 535                 540
Leu Gln Gly Arg Ser Glu Lys Gly Thr Leu Asp Ala Asn Leu Tyr Gln
545                 550                 555                 560
Asn Asn Tyr Arg Asn Phe Leu Ser Glu Glu Gln Asn Leu Thr Thr Ser
            565                 570                 575
Gly Asp Val Gly Cys Thr Gln Met Asn Tyr Tyr Gly Met Cys Ser
            580                 585                 590
Asn Pro Tyr Ser Glu Lys Pro Glu Trp Gln Met Gln Asn Ile Asp Lys
            595                 600                 605
Ala Arg Ile Arg Gly Leu Glu Leu Thr Gly Arg Leu Asn Val Thr Lys
            610                 615                 620
Val Ala Ser Phe Val Pro Glu Gly Trp Lys Leu Phe Gly Ser Leu Gly
625                 630                 635                 640
Tyr Ala Lys Ser Lys Leu Ser Gly Asp Asn Ser Leu Leu Ser Thr Gln
            645                 650                 655
```

```
Pro Pro Lys Val Ile Ala Gly Ile Asp Tyr Glu Ser Pro Ser Glu Lys
        660                 665                 670

Trp Gly Val Phe Ser Arg Leu Thr Tyr Leu Gly Ala Lys Lys Ala Lys
        675                 680                 685

Asp Ala Gln Tyr Thr Val Tyr Glu Asn Lys Gly Arg Gly Thr Pro Leu
    690                 695                 700

Gln Lys Lys Val Lys Asp Tyr Pro Trp Leu Asn Lys Ser Ala Tyr Val
705                 710                 715                 720

Phe Asp Met Tyr Gly Phe Tyr Lys Leu Ala Lys Asn Leu Thr Leu Arg
                725                 730                 735

Ala Gly Val Tyr Asn Val Phe Asn Arg Lys Tyr Thr Thr Trp Asp Ser
            740                 745                 750

Leu Arg Gly Leu Tyr Ser Tyr Ser Thr Thr Asn Ala Val Asp Arg Asp
            755                 760                 765

Gly Lys Gly Leu Asp Arg Tyr Arg Ala Ser Gly Arg Asn Tyr Ala Val
770                 775                 780

Ser Leu Asp Trp Lys Phe
785                 790
```

(2) INFORMATION FOR SEQ ID NO: 9:

(i) SEQUENCE CHARACTERISTICS:
        (A) LENGTH: 602 amino acids
        (B) TYPE: amino acid
        (D) TOPOLOGY: linear (ii) MOLECULE TYPE: protein (xi) SEQUENCE DESCRIPTION: SEQ ID NO: 9:

```
Met Gln Gln Gln His Leu Phe Arg Leu Asn Ile Leu Cys Leu Ser Leu
  1                 5                  10                  15

Met Thr Ala Leu Pro Val Tyr Ala Glu Asn Val Gln Ala Glu Gln Ala
                20                  25                  30

Gln Glu Lys Gln Leu Asp Thr Ile Gln Val Lys Ala Lys Lys Gln Lys
            35                  40                  45

Thr Arg Arg Asp Asn Glu Val Thr Gly Leu Gly Lys Leu Val Lys Ser
 50                  55                  60

Ser Asp Thr Leu Ser Lys Glu Gln Val Leu Asn Ile Arg Asp Leu Thr
 65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
                100                 105                 110

Val Asp Gly Val Ser Gln Ile Gln Ser Tyr Thr Ala Gln Ala Ala Leu
            115                 120                 125

Gly Gly Thr Arg Thr Ala Gly Ser Ser Gly Ala Ile Asn Glu Ile Glu
        130                 135                 140

Tyr Glu Asn Val Lys Ala Val Glu Ile Ser Lys Gly Ser Asn Ser Ser
145                 150                 155                 160

Glu Tyr Gly Asn Gly Ala Leu Ala Gly Ser Val Ala Phe Gln Thr Lys
                165                 170                 175

Thr Ala Ala Asp Ile Ile Gly Glu Gly Lys Gln Trp Gly Ile Gln Ser
            180                 185                 190

Lys Thr Ala Tyr Ser Gly Lys Asp His Ala Leu Thr Gln Ser Leu Ala
        195                 200                 205
```

```
Leu Ala Gly Arg Ser Gly Gly Ala Glu Ala Leu Leu Ile Tyr Thr Lys
    210                 215                 220
Arg Arg Gly Arg Glu Ile His Ala His Lys Asp Ala Gly Lys Gly Val
225                 230                 235                 240
Gln Ser Phe Asn Arg Leu Pro Ile Cys Arg Phe Gly Asn Asn Thr Tyr
                245                 250                 255
Thr Asp Cys Thr Pro Arg Asn Ile Gly Gly Asn Gly Tyr Tyr Ala Ala
            260                 265                 270
Val Gln Asp Asn Val Arg Leu Gly Arg Trp Ala Asp Val Gly Ala Gly
        275                 280                 285
Ile Arg Tyr Asp Tyr Arg Ser Thr His Ser Glu Asp Lys Ser Val Ser
    290                 295                 300
Thr Gly Thr His Arg Asn Leu Ser Trp Asn Ala Gly Val Val Leu Lys
305                 310                 315                 320
Pro Phe Thr Trp Met Asp Leu Thr Tyr Arg Ala Ser Thr Gly Phe Arg
                325                 330                 335
Leu Pro Ser Phe Ala Glu Met Tyr Gly Trp Arg Ala Gly Glu Ser Leu
            340                 345                 350
Lys Thr Leu Asp Leu Lys Pro Glu Lys Ser Phe Asn Arg Glu Ala Gly
        355                 360                 365
Ile Val Phe Lys Gly Asp Phe Gly Asn Leu Glu Ala Ser Tyr Phe Asn
    370                 375                 380
Asn Ala Tyr Arg Asp Leu Ile Ala Phe Gly Tyr Glu Thr Arg Thr Gln
385                 390                 395                 400
Asn Gly Gln Thr Ser Ala Ser Gly Asp Pro Gly Tyr Arg Asn Ala Gln
                405                 410                 415
Asn Ala Arg Ile Ala Gly Ile Asn Ile Leu Gly Lys Ile Asp Trp His
            420                 425                 430
Gly Val Trp Gly Gly Leu Pro Asp Gly Leu Tyr Ser Thr Leu Ala Tyr
        435                 440                 445
Asn Arg Ile Lys Val Lys Asp Ala Asp Ile Arg Ala Asp Arg Thr Phe
    450                 455                 460
Val Thr Ser Tyr Leu Phe Asp Ala Val Gln Pro Ser Arg Tyr Val Leu
465                 470                 475                 480
Gly Leu Gly Tyr Asp His Pro Asp Gly Ile Trp Gly Ile Asn Thr Met
                485                 490                 495
Phe Thr Tyr Ser Lys Ala Lys Ser Val Asp Glu Leu Leu Gly Ser Gln
            500                 505                 510
Ala Leu Leu Asn Gly Asn Ala Asn Ala Lys Lys Ala Ala Ser Arg Arg
        515                 520                 525
Thr Arg Pro Trp Tyr Val Thr Asp Val Ser Gly Tyr Tyr Asn Ile Lys
    530                 535                 540
Lys His Leu Thr Leu Arg Ala Gly Val Tyr Asn Leu Leu Asn Tyr Arg
545                 550                 555                 560
Tyr Val Thr Trp Glu Asn Val Arg Gln Thr Ala Gly Gly Ala Val Asn
                565                 570                 575
Gln His Lys Asn Val Gly Val Tyr Asn Arg Tyr Ala Ala Pro Gly Arg
            580                 585                 590
Asn Tyr Thr Phe Ser Leu Glu Met Lys Phe
    595                 600
```

(2) INFORMATION FOR SEQ ID NO: 10:

(i) SEQUENCE CHARACTERISTICS:
    (A) LENGTH: 607 amino acids
    (B) TYPE: amino acid
    (D) TOPOLOGY: linear (ii) MOLECULE TYPE: protein (xi) SEQUENCE DESCRIPTION: SEQ ID NO: 10:

```
Met Asn Lys Lys His Gly Phe Gln Leu Thr Leu Thr Ala Leu Ala Val
 1               5                  10                  15

Ala Ala Ala Phe Pro Ser Tyr Ala Ala Asn Pro Glu Thr Ala Ala Pro
            20                  25                  30

Asp Ala Ala Gln Thr Gln Ser Leu Lys Glu Val Thr Val Arg Ala Ala
            35                  40                  45

Lys Val Gly Arg Arg Ser Lys Glu Ala Thr Gly Leu Gly Lys Ile Ala
 50                  55                  60

Lys Thr Ser Glu Thr Leu Asn Lys Glu Gln Val Leu Gly Ile Arg Asp
 65                  70                  75                  80

Leu Thr Arg Tyr Asp Pro Gly Val Ala Val Glu Gln Gly Asn Gly
                85                  90                  95

Ala Ser Gly Gly Tyr Ser Ile Arg Gly Val Asp Lys Asn Arg Val Ala
            100                 105                 110

Val Ser Val Asp Gly Val Ala Gln Ile Gln Ala Phe Thr Val Gln Gly
            115                 120                 125

Ser Leu Ser Gly Tyr Gly Gly Arg Gly Gly Ser Gly Ala Ile Asn Glu
            130                 135                 140

Ile Glu Tyr Glu Asn Ile Ser Thr Val Glu Ile Asp Lys Gly Ala Gly
145                 150                 155                 160

Ser Ser Asp His Gly Ser Gly Ala Leu Gly Gly Ala Val Ala Phe Arg
                165                 170                 175

Thr Lys Glu Ala Ala Asp Leu Ile Ser Asp Gly Lys Ser Trp Gly Ile
                180                 185                 190

Gln Ala Lys Thr Ala Tyr Gly Ser Lys Asn Arg Gln Phe Met Lys Ser
            195                 200                 205

Leu Gly Ala Gly Phe Ser Lys Asp Gly Trp Glu Gly Leu Leu Ile Arg
            210                 215                 220

Thr Glu Arg Gln Gly Arg Glu Thr His Pro His Gly Asp Ile Ala Asp
225                 230                 235                 240

Gly Val Ala Tyr Gly Ile Asn Arg Leu Ser Val Cys Gly Tyr Ile Glu
                245                 250                 255

Thr Leu Arg Ser Arg Lys Cys Val Pro Arg Lys Ile Asn Gly Ser Asn
            260                 265                 270

Ile His Ile Ser Leu Asn Asp Arg Phe Ser Ile Gly Lys Tyr Phe Asp
            275                 280                 285

Phe Ser Leu Gly Gly Arg Tyr Asp Arg Lys Asn Phe Thr Thr Ser Glu
            290                 295                 300

Glu Leu Val Arg Ser Gly Arg Tyr Val Asp Arg Ser Trp Asn Ser Gly
305                 310                 315                 320

Ile Val Phe Lys Pro Asn Arg His Phe Ser Leu Ser Tyr Arg Ala Ser
                325                 330                 335

Ser Gly Phe Arg Thr Pro Ser Phe Gln Glu Leu Phe Gly Ile Asp Ile
            340                 345                 350
```

-continued

```
Tyr His Asp Tyr Pro Lys Gly Trp Gln Arg Pro Ala Leu Lys Ser Glu
        355                 360                 365

Lys Ala Ala Asn Arg Glu Ile Gly Leu Gln Trp Lys Gly Asp Phe Gly
370                 375                 380

Phe Leu Glu Ile Ser Ser Phe Arg Asn Arg Tyr Thr Asp Met Ile Ala
385                 390                 395                 400

Val Ala Asp His Lys Thr Lys Leu Pro Asn Gln Ala Gly Gln Leu Thr
                405                 410                 415

Glu Ile Asp Ile Arg Asp Tyr Tyr Asn Ala Gln Asn Met Ser Leu Gln
                420                 425                 430

Gly Val Asn Ile Leu Gly Lys Ile Asp Trp Asn Gly Val Tyr Gly Lys
                435                 440                 445

Leu Pro Glu Gly Leu Tyr Thr Thr Leu Ala Tyr Asn Arg Ile Lys Pro
450                 455                 460

Lys Ser Val Ser Asn Arg Pro Gly Leu Ser Leu Arg Ser Tyr Ala Leu
465                 470                 475                 480

Asp Ala Val Gln Pro Ser Arg Tyr Val Leu Gly Phe Gly Tyr Asp Gln
                485                 490                 495

Pro Glu Gly Lys Trp Gly Ala Asn Ile Met Leu Thr Tyr Ser Lys Gly
                500                 505                 510

Lys Asn Pro Asp Glu Leu Ala Tyr Leu Ala Gly Asp Gln Lys Arg Tyr
                515                 520                 525

Ser Thr Lys Arg Ala Ser Ser Ser Trp Ser Thr Ala Asp Val Ser Ala
                530                 535                 540

Tyr Leu Asn Leu Lys Lys Arg Leu Thr Leu Arg Ala Ala Ile Tyr Asn
545                 550                 555                 560

Ile Gly Asn Tyr Arg Tyr Val Thr Trp Glu Ser Leu Arg Gln Thr Ala
                565                 570                 575

Glu Ser Thr Ala Asn Arg His Gly Gly Asp Ser Asn Tyr Gly Arg Tyr
                580                 585                 590

Ala Ala Pro Gly Arg Asn Phe Ser Leu Ala Leu Glu Met Lys Phe
                595                 600                 605
```

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

AAACAGGTCT CGGCATAG        18

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CGCGAATTCA AACAGGTCTC GGCATAG        27

(2) INFORMATION FOR SEQ ID NO: 13:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 13:

CGCGAATTCA AAAACTTCCA TTCCAGCGAT ACG                33

(2) INFORMATION FOR SEQ ID NO: 14:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO: 14:

TAAAACTTCC ATTCCAGCGA TACG                          24

(2) INFORMATION FOR SEQ ID NO: 15:

(i) SEQUENCE CHARACTERISTICS:
       (A) LENGTH: 7 amino acids
       (B) TYPE:AMINO
       (B) TYPE:AMINO
       (D) TOPOLOGY: linear (ii) MOLECULE TYPE: peptide (xi) SEQUENCE DESCRIPTION: SEQ ID NO: 15:

Glu Thr Thr Pro Val Lys Ala